US012643932B2

(12) United States Patent (10) Patent No.: US 12,643,932 B2
Stauss et al. (45) Date of Patent: Jun. 2, 2026

---

(54) ENGINEERED REGULATORY T CELL

(71) Applicant: UCL Business Ltd, London (GB)

(72) Inventors: Hans Stauss, London (GB); Sharyn Thomas, London (GB); Olivier Preham, London (GB)

(73) Assignee: UCL Business Ltd, London (GB)

( * ) Notice: Subject to any disclaimer, the term of this patent is extended or adjusted under 35 U.S.C. 154(b) by 1059 days.

(21) Appl. No.: 17/771,466

(22) PCT Filed: Oct. 22, 2020

(86) PCT No.: PCT/GB2020/052659
§ 371 (c)(1),
(2) Date: Apr. 23, 2022

(87) PCT Pub. No.: WO2021/079122
PCT Pub. Date: Apr. 29, 2021

(65) Prior Publication Data
US 2022/0364057 A1 Nov. 17, 2022

(30) Foreign Application Priority Data

| | | |
|---|---|---|
| Oct. 23, 2019 | (GB) | 1915341 |
| Oct. 23, 2019 | (GB) | 1915344 |
| Oct. 23, 2019 | (GB) | 1915347 |
| Oct. 23, 2019 | (GB) | 1915348 |
| Oct. 23, 2019 | (GB) | 1915351 |
| Oct. 23, 2019 | (GB) | 1915354 |
| Oct. 23, 2019 | (GB) | 1915357 |
| Oct. 23, 2019 | (GB) | 1915360 |
| Oct. 23, 2019 | (GB) | 1915362 |
| Oct. 23, 2019 | (GB) | 1915366 |

(51) Int. Cl.

| | |
|---|---|
| *C07K 14/725* | (2006.01) |
| *A61K 40/11* | (2025.01) |
| *A61K 40/22* | (2025.01) |
| *A61K 40/32* | (2025.01) |
| *A61K 40/40* | (2025.01) |
| *C07K 14/47* | (2006.01) |
| *C07K 14/705* | (2006.01) |
| *C12N 5/0783* | (2010.01) |

(52) U.S. Cl.
CPC .......... *C07K 14/7051* (2013.01); *A61K 40/11* (2025.01); *A61K 40/22* (2025.01); *A61K 40/32* (2025.01); *A61K 40/40* (2025.01); *C07K 14/4702* (2013.01); *C12N 5/0637* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 7,131,958 | B2 | 11/2006 | Deverre |
| 7,147,626 | B2 | 12/2006 | Goodman et al. |
| 2014/0004133 | A1 | 1/2014 | Bykovskaia et al. |
| 2016/0194605 | A1 | 7/2016 | Scott et al. |
| 2019/0203174 | A1 | 7/2019 | Scott et al. |

FOREIGN PATENT DOCUMENTS

| | | | | |
|---|---|---|---|---|
| WO | WO-2009050283 A1 | 4/2009 | | |
| WO | WO-2014145970 A1 | 9/2014 | | |
| WO | WO-2014183056 A1 * | 11/2014 | ............ | A61K 35/17 |
| WO | WO-2016133779 A1 | 8/2016 | | |
| WO | 2016174461 A1 | 11/2016 | | |
| WO | WO-2017062035 A1 | 4/2017 | | |
| WO | 2019202323 A1 | 10/2019 | | |
| WO | WO-2019202322 A1 | 10/2019 | | |
| WO | 2021079120 A1 | 4/2021 | | |

OTHER PUBLICATIONS

Nguyen et al. (Biochem. Soc. Trans. Nov. 1, 2021; 49 (5): 2319-31) (Year: 2021).*
Dall'Era et al., Arthritis & Rheumatology 71.3 (2019): 431-440. (Year: 2019).*
Frantz et al., Frontiers in immunology 9 (2018): 2356. (Year: 2018).*
Romano et al., Frontiers in immunology 10 (2019): 43. (Year: 2019).*
Walker et al. (J. Clin. Invest. Nov. 1, 2003; 112 (9): 1437-43) (Year: 2003).*
Yagi et al. (Int. Immunol. Nov. 2004; 16 (11):1643-56) (Year: 2004).*
Bell et al. (J. Biol. Chem. Sep. 9, 1994; 269 (36): 22758-63) (Year: 1994).*
Lisa M. Bell, et al., "Cytoplasmic tail deletion of T cell receptor (TCR) B-chain results in its . . . ," Journal of Biological Chemistry, 1994, pp. 22758-22763, vol. 269, No. 36.
Roy A. Mariuzza, et al., "The structural basis of T-cell receptor (TCR) activation: an enduring enigma," Journal of Biological Chemistry, 2020, pp. 914-925, vol. 295, No. 4.
Ho-Keun Kwon, et al., "FoxP3 scanning mutagenesis reveals functional variegation and mild mutations with atypical autoimmune . . . ," PNAS, 2018, pp. E253-E262, vol. 115, No. 2.
Reiner K. W. Mailer, "Alternative splicing of FOXP3—virtue and vice," Frontiers in Immunology, 2018, art. 530, vol. 9.
Haruhiko Yagi, et al., "Crucial role of FOXP3 in the development and function of human CD25+CD4+ . . . ," International Immunology, 2004, pp. 1643-1656, vol. 16, No. 11.

(Continued)

*Primary Examiner* — Maria G Leavitt
*Assistant Examiner* — Brendan Thomas Tinsley
(74) *Attorney, Agent, or Firm* — Grimes & Yvon LLP

(57) ABSTRACT

The present invention relates to an engineered regulatory T cell (Treg) comprising a T cell receptor (TCR) which is capable of specifically binding to a myelin basic protein (MBP) peptide or variant or fragment thereof when the peptide is presented by a major histocompatibility complex (MHC) molecule. The present invention further relates to methods for providing an engineered Treg and to methods and uses of said engineered Treg and vectors and kits of vectors encoding said Treg.

9 Claims, 24 Drawing Sheets

Specification includes a Sequence Listing.

(56)            References Cited

OTHER PUBLICATIONS

Lin Chen, et al., "A humanized TCR retaining authentic specificity and affinity conferred potent anti-tumour cytotoxicity," Immunology, 2018, pp. 121-136, vol. 155.

E. Meinl & R. Hohlfeld, "Immunopathogenesis of multiple sclerosis: MBP and beyond," Clinical and Experimental Immunology, 2002, pp. 395-397, vol. 128, No. 3.

Peter Georgiev, et al., "Regulatory T cells: the many faces of Foxp3," Journal of Clinical Immunology, 2019, pp. 623-640, vol. 39, No. 7.

Andrea T. Nguyen, et al., "The pockets guide to HLA class I molecules," Biochemical Society Transactions, 2021, pp. 2319-2331, vol. 49.

Mindi R. Walker, et al., "Induction of FoxP3 and acquisition of T regulatory activity . . .," Journal of Clinical Investigation, 2003, pp. 1437-1443, vol. 12, No. 9.

Kim Young Chan, et al., Engineered MBP-specific human Tregs ameliorate MOG-induced EAE through IL-2-triggered inhibition of effector T cells, Journal of Autoimmunity, May 30, 2018, vol. 92, pp. 77-86.

Leigh A. Stevens, et al., Curing CNS autoimmune disease with myelin-reactive Foxp3+ Treg, European Journal of Immunology, Apr. 1, 2009, vol. 39, No. 4, pp. 1108-1117.

Divya J. Mekala & Terrence L. Geiger, Immunotherapy of autoimmune encephalomyelitis with redirected CD4+ CD25+ T lymphocytes, Blood, Mar. 1, 2005, vol. 105, No. 5, pp. 2090-2092.

Patrick R. Adair, et al., Human Tregs made antigen specific by gene modification: the power to treat autoimmunity and antidrug antibodies with precision, Frontiers in Immunology, Sep. 21, 2017, vol. 8, pp. 1117-1.

Alla L. Zozulya & Heinz Wiendl, The role of regulatory T cells in multiple sclerosis, Nature Clincal Practice Neurology, Jun. 24, 2008, vol. 4, No. 7, pp. 384-398.

Patrick R. Adair, et al., "Human Tregs made antigen specific by gene modification: the power to treat autoimmunity and antidrug . . . ", Front. Immunol., 2017, vol. 8, p. 1117.

Stephen F. Altschul, et al., "Basic local alignment search tool", J. Mol. Biol., 1990, vol. 215, pp. 403-410.

Frederick M. Ausubel, et al., "Short protocols in molecular biology", 1999, 4th edition, chapter 18.

Frederick M. Ausubel, et al., "Short protocols in molecular biology", 1999, 4th edition, pp. 7-58 to 7-60.

Ute Bank, et al., "Inhibition of alanyl-aminopeptidase on CD4+ CD25+ regulatory T-cells enhances expression of FoxP3 . . .", Int. J. Mol. Med., 2007, vol. 20, pp. 483-492.

John M. Coffin, et al., "Retroviruses", 1997, Cold Spring Harbour Laboratory Press Eds:, pp. 758-763.

Cyrille J. Cohen, et al., "Enhanced antitumor activity of T cells engineered to express T-cell receptors with a second . . .", Cancer Res., 2007, vol. 67, pp. 3898-3903.

Nicholas A. J. Dawson, et al., "Engineered tolerance: tailoring development, function and antigen-specificity of regulatory T cells," Front. Immunol., 2017, vol. 8, p. 1460.

John Devereux, et al., "A comprehensive set of sequence analysis programs for the VAX", Nucl. Acid Res., 1984, vol. 12, pp. 387-395.

Michelle L. L., Donnelly, et al., "The 'cleavage' activities of foot-and-mouth disease virus 2A site-directed mutants and . . .", J. Gen, Virol., 2001, vol. 82, pp. 1027-1041.

Geraldine Folch & Marie-Paule Lefranc, "The human T cell receptor beta variable (TRBV) genes", Exp. Clin. Immunogenet, 2000, vol. 17, pp. 42-54.

GenPept Accession No. 3O6 F_C, Chain C, and T-cell Receptor Alpha Chain Cregion, uploaded Sep. 7, 2011; Retrieved Feb. 13, 2023; URL: https://www.ncbi.nlm.nih.gov/protein . . .

GenPept Accession No. 3O6 F_D, Chain D, and T-cell Receiptor Beta-1 Chain C Region, uploaded Sep. 7, 2011. Retrieved Feb. 13, 2023; URL: https://www.ncbi.nlm.nih.gov/protein . . .

E. Hodges, et al., "Diagnostic role of tests for T cell receptor (TCR) genes", J. Clin. Pathol., 2003, vol. 56, pp. 1-11.

Jianbing Huang, et al., "Histone/protein deacetylase 11 targeting promotes Foxp3+ Treg function", Sci. Rep., 2017, vol. 7, p. 8626.

Jaebong Huh, et al., "Limited repertoire of HLA-DRB1*0401-restricted MBP111-129-specific T cells in HLA-DRB1*0401 Tg mice . . .", J. Neuroimmunol., 2004, vol. 151, pp. 94-102.

Yong Chan Kim et al., "Engineered myelin basic protein (MBP)-specific human T regulatory cells ameliorate myelin oligodendrocyte . . ." J. Immunol., 2017, vol. 198, p. 15.

Ben F. Koop, et al., "The human T-cell receptor TCRAC/TCRDC (Cα/Cδ) region: organization, sequence and evolution of 97.6 kb of DNA", Genomics, 1994, vol. 19, pp. 478-493.

Jürgen Kuball, et al., "Facilitating matched pairing and expression of TCR chains introduced into human T cells", Blood, 2007, vol. 109, pp. 2331-2338.

Marie-Paule Lefranc, et al., "IMGT unique numbering for immunoglobulin and T cell receptor variable domains and Ig . . .", Dev. Comp. Immunol., 2003, vol. 27, pp. 55-77.

Paul Lewis, et al., "Human immunodeficiency virus infection of cells arrested in the cell cycle", EMBO J., 1992, vol. 11, pp. 3053-3058.

Yunjie Lu, et al., "Rapamycin regulates iTreg function through CD39 and runx1 pathways", J. Immunol. Res., 2014, vol. 2014, p. 989434.

Stefan Lüth, et al., "Ectopic expression of neural autoantigen in mouse liver suppresses experimental autoimmune . . .", J. Clin. Invest., 2008, vol. 118, pp. 3403-3410.

Ydivya J. Mekala, et al., "IL-10-dependent infectious tolerance after the treatment of experimental allergic . . .", Proc. Natl. Acad. Sci. USA, 2005, vol. 102, pp. 11817-11822.

MMDB, 3O6F: Crystal Structure of a Numan Autominnune Tor Ms2-3c8 bound to Mhc class liSelf-ligand Mbp/hla-dr4, Sep. 2011; Retrieved Feb. 13, 2023; URL: https://www.ncbi.nlm.nih . . .

Paolo A. Muraro, et al., "Immunodominance of a low-affinity major histocompatibility complex-binding myelin basic . . .", J. Clin. Invest., 1997, vol. 100, pp. 339-349.

Carol Papworth, et al., "Highly efficient double-stranded site-directed mutagenesis with the Chameleon kit", Strategies Mol. Biol., 1996, vol. 7, pp. 38-40.

Jiangzhou Peng, et al., "The effect of foxp3-overexpressing Treg cells on non-small cell lung cancer cells", Mol. Med. Rep., 2018, vol. 17, pp. 5860-5868.

Victoria Riddell, "Generating ag-specific human regulatory T-cells by TCR gene transfer for the treatment of rheumatoid arthritis", (Thesis), 2019, Ediburgh Napier Univeristy.

Dominique Scaviner & Marie-Paule Lefranc, "The human T cell receptor alpha variable (TRAV) genes", Exp. Clin. Immunogenet., 2000, vol. 17, pp. 83-96.

Moa Fransson, et al., "CAR/FoxP3-engineered T regulatory cells target the CNS and suppress EAE upon intranasal delivery", J. Neuroinflammation, 2012, vol. 9, p. 112.

V. K. Tuohy, et al., "Preemptive targeting of the epitope spreading cascade with genetically modified regulatory T cells induces Tr1 . . .", FASEB J., 2001, vol. 15, p. A1212.

Graham P. Wright, et al., "Adoptive therapy with redirected primary regulatory T cells results in . . .", Proc. Natl. Acad. Sci., 2009, vol. 106, pp. 19078-19083.

Yiyuan Yin, et al., "Structure of a TCR with high affinity for sef-antigen reveals basis for escape from negative selection", EMBO J., 2011, vol. 30, pp. 1137-1148.

Guang-Ju Zhao, et al., "Growth arrest-specific 6 enhances the suppressive function of CD4+CD25+ regulatory T cells . . .", Mediators Inflamm., 2017, vol. 2017, p. 6848430.

Dun Zhou, et al., "High throughput analysis of TCR-β rearrangement and gene expression in single T cells", Lab. Invest., 2006, vol. 86, pp. 314-321.

Luming Zhou, et al., "Rare allele enrichment and detection by allele-specific PCR, competitive probe blocking, and melting analysis", BioTechniques, 2011, vol. 50, pp. 311-318.

Jacqueline A. Quandt, et al., "Unique clinical and pathological features in HLA-DRB1*0401-restricted MBP 111-129-specific . . .", J. Exp. Med., 2004, vol. 200, pp. 223-234.

(56)  References Cited

OTHER PUBLICATIONS

Kailash Singh, et al., "Concomitant analysis of Helios and Neuroilin-1 as a marker to detect thymic derived regulatory T cells in . . .", Sci. Rep., 2015, vol. 75, p. 7767.

Victoria Riddell, "Generating Ag-specific human regulatory T-cell by TCR gene transfer for the treatment of rheumatoid arthritis", Thesis Edinburgh Napier University, 2018.

Rafal Pacholczyk & Joanna Kern, "The T-Cell Receptor Repertoire of Regulatory T Cells", Immunology, 2008, pp. 450-458, vol. 125, No. 4.

UniProtKB Accession P02686-5, Myelin Basic Protein Human, uploaded Jul. 21, 1986; Retrieved Dec. 13, 2024; URL: https://www.uniprot.org/uniprotkb/P02686/entry.

Lee Rowen, et al., "The Complete 685-Kilobase DNA Sequence of the Human Beta T Cell Receptor Locus", Science, 1996, pp. 1755-1762, vol. 272, No. 5269.

CAS Registry No. 1637420-83-7, TCR $\alpha\beta$ (receptor), anti-(human myelin basic protein) (synthetic human single-chain), uploaded Nov. 26, 2014.

Zenichiro Kato, et al., "Positioning of Autoimmune TCR-Ob.2F3 and . . .", Proceedings of the National Academy Science of the USA, 2008, pp. 15523-15528, vol. 105, No. 40.

Zenichiro Kato, et al., "The Autoimmune TCR-Ob.2F3 Can Bind to MBP85-99/HLA-DR2 Having an Unconventional . . .", Molecular Immunology, 2010, pp. 314-320, vol. 48, No. 1-3.

Database Geneseq Accession No. BBP99214, Human Myelin Basic Protein (MBP), SEQ2, uploaded Jan. 1, 2015, XP093218717.

Lucienne Chatenoud, "Natural and Induced T CD4+CD25+ FOXP3+ Regulatory T Cells", Methods in Molecular Biology, 2011, pp. 3-13, vol. 677.

Jenny Mcgovern, et al., "Forced Fox-P3 Expression Can Improve the Safety and Antigen-Specific Function of Engineered Regulatory T Cells", Journal of Autoimmunity, 2022, Article 102888, pp. 1-7, vol. 132.

Martha S. Jordan, et al., "Thymic Selection of CD4+CD25+ Regulatory T Cells Induced by an Agonist Self-Peptide", Nature Immunology, 2001, pp. 301-306, vol. 2, No. 4.

Kaitlyn A. Lagattuta, et al., "Repertoire Analyses Reveal T Cell Antigen Receptor Sequence Features that Influence T Cell Fate", Nature Immunology, 2022, pp. 446-457, vol. 23, No. 3.

Jian Peng, et al., "Converting Antigen-Specific Diabetogenic CD4 and CD8 T Cells to TGF-Beta Producing Non-Pathogenic Regulatory Cells Following FoxP3 Transduction", Journal of Autoimmunity, 2007, pp. 188-200, vol. 28, No. 4.

Alexander Y. Rudensky, "Regulatory T Cells and Foxp3", Immunological Reviews, 2011, pp. 260-268, vol. 241, No. 1.

Masahiko Akamatsu, et al., "Conversion of Antigen-Specific Effector/Memory T Cells into Foxp3-Expressing Treg Cells by Inhibition of CDK8/19", Science Immunology, 2019, p. eaaw2707, vol. 4, No. 40.

Craig Hall, et al. "Requirements for Cell Surface Expression of the Human TCR/CD3 Complex in Non-T cells", International Immunology, 1991, pp. 359-368, vol. 3, No. 4.

Laura Jardine, et al., "Rapid Detection of Dendritic Cell and Monocyte Disorders Using CD4 as a Lineage Marker of the Human Peripheral Blood Antigen-Presenting Cell Compartment", Frontiers in Immunology, 2013, article 495, pp. 1-8, vol. 4.

Zhiyuan Li, et al., "FOXP3+ Regulatory T Cells and their Functional Regulation", Cellular & Molecular Immunology, 2015, pp. 558-565, vol. 12, No. 4.

Ming O. Li & Alexander Y. Rudensky, "T Cell Receptor Signalling in the Control of Regulatory T Cell Differentiation and Function", Nature Reviews Immunology, 2016, pp. 220-233, vol. 16, No. 4.

* cited by examiner a

| Variable α | Con. α | P2A | Variable β | Con. β | T2A | tmCD19 |

(cloned into pMP71 vector)

| Variable α | Con. α | P2A | Variable β | Con. β | T2A | tmCD19 |

(cloned into pMP71 vector)

c d a

| Variable α | Con. α | P2A | Variable β | Con. β | T2A | tmCD19 |

(cloned into pMP71 vector)

b a

| Variable α | Con. α | P2A | Variable β | Con. β | T2A | tmCD19 |

(cloned into pMP71 vector)

b a

| Variable α | Con. α | P2A | Variable β | Con. β | T2A | tmCD19 |

(cloned into pMP71 vector)

a

| Variable α | Con. α | P2A | Variable β | Con. β | T2A | tmCD19 |

(cloned into pMP71 vector)

b a

| Variable α | Con. α | P2A | Variable β | Con. β | T2A | tmCD19 |

(cloned into pMP71 vector)

b a

| Variable α | Con. α | P2A | Variable β | Con. β | T2A | tmCD19 |

(cloned into pMP71 vector)

b a

| Variable α | Con. α | P2A | Variable β | Con. β | T2A | tmCD19 |

(cloned into pMP71 vector)

SEQUENCE LISTING

```
<160> NUMBER OF SEQ ID NOS: 97

<210> SEQ ID NO 1
<211> LENGTH: 12
<212> TYPE: PRT
<213> ORGANISM: Artificial Sequence
<220> FEATURE:
<223> OTHER INFORMATION: T cell receptor (TCR) alpha chain
      complementarity determining region (CDR), CDR3alpha

<400> SEQUENCE: 1

Ala Thr Asp Thr Thr Ser Gly Thr Tyr Lys Tyr Ile
1               5                   10

<210> SEQ ID NO 2
<211> LENGTH: 14
<212> TYPE: PRT
<213> ORGANISM: Artificial Sequence
<220> FEATURE:
<223> OTHER INFORMATION: TCR beta chain CDR, CDR3beta

<400> SEQUENCE: 2

Ser Ala Arg Asp Leu Thr Ser Gly Ala Asn Asn Glu Gln Phe
1               5                   10
```

```
<210> SEQ ID NO 3
<211> LENGTH: 5
<212> TYPE: PRT
<213> ORGANISM: Artificial Sequence
<220> FEATURE:
<223> OTHER INFORMATION: TCR alpha chain CDR, CDR1alpha

<400> SEQUENCE: 3

Thr Ser Ile Asn Asn
1               5

<210> SEQ ID NO 4
<211> LENGTH: 7
<212> TYPE: PRT
<213> ORGANISM: Artificial Sequence
<220> FEATURE:
<223> OTHER INFORMATION: TCR alpha chain CDR, CDR2alpha

<400> SEQUENCE: 4

Ile Arg Ser Asn Glu Arg Glu
1               5

<210> SEQ ID NO 5
<211> LENGTH: 6
<212> TYPE: PRT
<213> ORGANISM: Artificial Sequence
<220> FEATURE:
<223> OTHER INFORMATION: TCR beta chain CDR, CDR1beta

<400> SEQUENCE: 5

Asp Phe Gln Ala Thr Thr
1               5

<210> SEQ ID NO 6
<211> LENGTH: 7
<212> TYPE: PRT
<213> ORGANISM: Artificial Sequence
<220> FEATURE:
<223> OTHER INFORMATION: TCR beta chain CDR, CDR2beta

<400> SEQUENCE: 6

Ser Asn Glu Gly Ser Lys Ala
1               5

<210> SEQ ID NO 7
<211> LENGTH: 113
<212> TYPE: PRT
<213> ORGANISM: Artificial Sequence
<220> FEATURE:
<223> OTHER INFORMATION: illustrative TCR alpha chain variable region

<400> SEQUENCE: 7

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
                20                  25                  30

Gln Trp Tyr Arg Gln Asn Ser Gly Arg Gly Leu Val His Leu Ile Leu
            35                  40                  45

Ile Arg Ser Asn Glu Arg Glu Lys His Ser Gly Arg Leu Arg Val Thr
        50                  55                  60

Leu Asp Thr Ser Lys Lys Ser Ser Ser Leu Leu Ile Thr Ala Ser Arg
65                  70                  75                  80

Ala Ala Asp Thr Ala Ser Tyr Phe Cys Ala Thr Asp Thr Thr Ser Gly
```

-continued

```
                         85                    90                    95

Thr Tyr Lys Tyr Ile Phe Gly Thr Gly Thr Arg Leu Lys Val Leu Ala
                100                   105                   110

Asn

<210> SEQ ID NO 8
<211> LENGTH: 118
<212> TYPE: PRT
<213> ORGANISM: Artificial Sequence
<220> FEATURE:
<223> OTHER INFORMATION: illustrative TCR beta chain variable region

<400> SEQUENCE: 8

Gly Ala Val Val Ser Gln His Pro Ser Trp Val Ile Cys Lys Ser Gly
1               5                    10                    15

Thr Ser Val Lys Ile Glu Cys Arg Ser Leu Asp Phe Gln Ala Thr Thr
                20                    25                    30

Met Phe Trp Tyr Arg Gln Phe Pro Lys Gln Ser Leu Met Leu Met Ala
            35                    40                    45

Thr Ser Asn Glu Gly Ser Lys Ala Thr Tyr Glu Gln Gly Val Glu Lys
        50                    55                    60

Asp Lys Phe Leu Ile Asn His Ala Ser Leu Thr Leu Ser Thr Leu Thr
65                    70                    75                    80

Val Thr Ser Ala His Pro Glu Asp Ser Ser Phe Tyr Ile Cys Ser Ala
                85                    90                    95

Arg Asp Leu Thr Ser Gly Ala Asn Asn Glu Gln Phe Phe Gly Pro Gly
                100                   105                   110

Thr Arg Leu Thr Val Leu
        115

<210> SEQ ID NO 9
<211> LENGTH: 253
<212> TYPE: PRT
<213> ORGANISM: Artificial Sequence
<220> FEATURE:
<223> OTHER INFORMATION: illustrative TCR alpha chain

<400> SEQUENCE: 9

Ser Gln Gln Gly Glu Glu Asp Pro Gln Ala Leu Ser Ile Gln Glu Gly
1               5                    10                    15

Glu Asn Ala Thr Met Asn Cys Ser Tyr Lys Thr Ser Ile Asn Asn Leu
                20                    25                    30

Gln Trp Tyr Arg Gln Asn Ser Gly Arg Gly Leu Val His Leu Ile Leu
            35                    40                    45

Ile Arg Ser Asn Glu Arg Glu Lys His Ser Gly Arg Leu Arg Val Thr
        50                    55                    60

Leu Asp Thr Ser Lys Lys Ser Ser Ser Leu Leu Ile Thr Ala Ser Arg
65                    70                    75                    80

Ala Ala Asp Thr Ala Ser Tyr Phe Cys Ala Thr Asp Thr Thr Ser Gly
                85                    90                    95

Thr Tyr Lys Tyr Ile Phe Gly Thr Gly Thr Arg Leu Lys Val Leu Ala
                100                   105                   110

Asn Ile Gln Asn Pro Asp Pro Ala Val Tyr Gln Leu Arg Asp Ser Lys
            115                   120                   125

Ser Ser Asp Lys Ser Val Cys Leu Phe Thr Asp Phe Asp Ser Gln Thr
        130                   135                   140

Asn Val Ser Gln Ser Lys Asp Ser Asp Val Tyr Ile Thr Asp Lys Thr
```

-continued

```
145                 150                 155                 160

Val Leu Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
            180                 185                 190

Ile Ile Pro Glu Asp Thr Phe Phe Pro Ser Pro Glu Ser Ser Cys Asp
            195                 200                 205

Val Lys Leu Val Glu Lys Ser Phe Glu Thr Asp Thr Asn Leu Asn Phe
            210                 215                 220

Gln Asn Leu Ser Val Ile Gly Phe Arg Ile Leu Leu Leu Lys Val Ala
225                 230                 235                 240

Gly Phe Asn Leu Leu Met Thr Leu Arg Leu Trp Ser Ser
                245                 250

<210> SEQ ID NO 10
<211> LENGTH: 297
<212> TYPE: PRT
<213> ORGANISM: Artificial Sequence
<220> FEATURE:
<223> OTHER INFORMATION: illustrative TCR beta chain

<400> SEQUENCE: 10

Gly Ala Val Val Ser Gln His Pro Ser Trp Val Ile Cys Lys Ser Gly
1               5                   10                  15

Thr Ser Val Lys Ile Glu Cys Arg Ser Leu Asp Phe Gln Ala Thr Thr
            20                  25                  30

Met Phe Trp Tyr Arg Gln Phe Pro Lys Gln Ser Leu Met Leu Met Ala
        35                  40                  45

Thr Ser Asn Glu Gly Ser Lys Ala Thr Tyr Glu Gln Gly Val Glu Lys
        50                  55                  60

Asp Lys Phe Leu Ile Asn His Ala Ser Leu Thr Leu Ser Thr Leu Thr
65                  70                  75                  80

Val Thr Ser Ala His Pro Glu Asp Ser Ser Phe Tyr Ile Cys Ser Ala
                85                  90                  95

Arg Asp Leu Thr Ser Gly Ala Asn Asn Glu Gln Phe Phe Gly Pro Gly
            100                 105                 110

Thr Arg Leu Thr Val Leu Glu Asp Leu Lys Asn Val Phe Pro Pro Glu
            115                 120                 125

Val Ala Val Phe Glu Pro Ser Glu Ala Glu Ile Ser His Thr Gln Lys
            130                 135                 140

Ala Thr Leu Val Cys Leu Ala Thr Gly Phe Tyr Pro Asp His Val Glu
145                 150                 155                 160

Leu Ser Trp Trp Val Asn Gly Lys Glu Val His Ser Gly Val Ser Thr
                165                 170                 175

Asp Pro Gln Pro Leu Lys Glu Gln Pro Ala Leu Asn Asp Ser Arg Tyr
            180                 185                 190

Cys Leu Ser Ser Arg Leu Arg Val Ser Ala Thr Phe Trp Gln Asn Pro
            195                 200                 205

Arg Asn His Phe Arg Cys Gln Val Gln Phe Tyr Gly Leu Ser Glu Asn
            210                 215                 220

Asp Glu Trp Thr Gln Asp Arg Ala Lys Pro Val Thr Gln Ile Val Ser
225                 230                 235                 240

Ala Glu Ala Trp Gly Arg Ala Asp Cys Gly Phe Thr Ser Glu Ser Tyr
                245                 250                 255

Gln Gln Gly Val Leu Ser Ala Thr Ile Leu Tyr Glu Ile Leu Leu Gly
```

```
                260             265             270
Lys Ala Thr Leu Tyr Ala Val Leu Val Ser Ala Leu Val Leu Met Ala
            275             280             285

Met Val Lys Arg Lys Asp Ser Arg Gly
    290             295

<210> SEQ ID NO 11
<211> LENGTH: 304
<212> TYPE: PRT
<213> ORGANISM: Homo sapiens

<400> SEQUENCE: 11

Met Gly Asn His Ala Gly Lys Arg Glu Leu Asn Ala Glu Lys Ala Ser
1               5               10              15

Thr Asn Ser Glu Thr Asn Arg Gly Glu Ser Glu Lys Lys Arg Asn Leu
            20              25              30

Gly Glu Leu Ser Arg Thr Thr Ser Glu Asp Asn Glu Val Phe Gly Glu
        35              40              45

Ala Asp Ala Asn Gln Asn Asn Gly Thr Ser Ser Gln Asp Thr Ala Val
    50              55              60

Thr Asp Ser Lys Arg Thr Ala Asp Pro Lys Asn Ala Trp Gln Asp Ala
65              70              75              80

His Pro Ala Asp Pro Gly Ser Arg Pro His Leu Ile Arg Leu Phe Ser
            85              90              95

Arg Asp Ala Pro Gly Arg Glu Asp Asn Thr Phe Lys Asp Arg Pro Ser
            100             105             110

Glu Ser Asp Glu Leu Gln Thr Ile Gln Glu Asp Ser Ala Ala Thr Ser
        115             120             125

Glu Ser Leu Asp Val Met Ala Ser Gln Lys Arg Pro Ser Gln Arg His
    130             135             140

Gly Ser Lys Tyr Leu Ala Thr Ala Ser Thr Met Asp His Ala Arg His
145             150             155             160

Gly Phe Leu Pro Arg His Arg Asp Thr Gly Ile Leu Asp Ser Ile Gly
            165             170             175

Arg Phe Phe Gly Gly Asp Arg Gly Ala Pro Lys Arg Gly Ser Gly Lys
            180             185             190

Asp Ser His His Pro Ala Arg Thr Ala His Tyr Gly Ser Leu Pro Gln
            195             200             205

Lys Ser His Gly Arg Thr Gln Asp Glu Asn Pro Val Val His Phe Phe
    210             215             220

Lys Asn Ile Val Thr Pro Arg Thr Pro Pro Pro Ser Gln Gly Lys Gly
225             230             235             240

Arg Gly Leu Ser Leu Ser Arg Phe Ser Trp Gly Ala Glu Gly Gln Arg
            245             250             255

Pro Gly Phe Gly Tyr Gly Gly Arg Ala Ser Asp Tyr Lys Ser Ala His
            260             265             270

Lys Gly Phe Lys Gly Val Asp Ala Gln Gly Thr Leu Ser Lys Ile Phe
    275             280             285

Lys Leu Gly Gly Arg Asp Ser Arg Ser Gly Ser Pro Met Ala Arg Arg
    290             295             300

<210> SEQ ID NO 12
<211> LENGTH: 21
<212> TYPE: PRT
<213> ORGANISM: Homo sapiens
```

-continued

```
<400> SEQUENCE: 12

Asp Glu Asn Pro Val Val His Phe Phe Lys Asn Ile Val Thr Pro Arg
1               5                   10                  15

Thr Pro Pro Pro Ser
            20

<210> SEQ ID NO 13
<211> LENGTH: 171
<212> TYPE: PRT
<213> ORGANISM: Homo sapiens

<400> SEQUENCE: 13

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Asp Ser His His Pro
    50                  55                  60

Ala Arg Thr Ala His Tyr Gly Ser Leu Pro Gln Lys Ser His Gly Arg
65                  70                  75                  80

Thr Gln Asp Glu Asn Pro Val Val His Phe Phe Lys Asn Ile Val Thr
                85                  90                  95

Pro Arg Thr Pro Pro Ser Gln Gly Lys Gly Arg Gly Leu Ser Leu
            100                 105                 110

Ser Arg Phe Ser Trp Gly Ala Glu Gly Gln Arg Pro Gly Phe Gly Tyr
            115                 120                 125

Gly Gly Arg Ala Ser Asp Tyr Lys Ser Ala His Lys Gly Phe Lys Gly
        130                 135                 140

Val Asp Ala Gln Gly Thr Leu Ser Lys Ile Phe Lys Leu Gly Gly Arg
145                 150                 155                 160

Asp Ser Arg Ser Gly Ser Pro Met Ala Arg Arg
                165                 170

<210> SEQ ID NO 14
<211> LENGTH: 339
<212> TYPE: DNA
<213> ORGANISM: Artificial Sequence
<220> FEATURE:
<223> OTHER INFORMATION: sequence encoding TCR alpha chain variable
      region

<400> SEQUENCE: 14
agccagcagg gcgaagagga tccccaggct ctgtctattc aagagggcga gaacgccacc      60
atgaactgca gctacaagac cagcatcaac aacctgcagt ggtacagaca gaacagcggc     120
agaggactgg tgcacctgat cctgatcaga agcaacgaga gagagaagca ctccggcaga     180
ctgagagtga ccctggacac cagcaagaag tccagcagcc tgctgatcac agccagcaga     240
gccgccgata ccgccagcta cttttgtgcc accgatacca cctccggcac ctacaagtac     300
atcttcggca ccggcaccag actgaaggtg ctggccaac                           339

<210> SEQ ID NO 15
<211> LENGTH: 354
<212> TYPE: DNA
<213> ORGANISM: Artificial Sequence
<220> FEATURE:
<223> OTHER INFORMATION: sequence encoding TCR beta chain variable
``` region

<400> SEQUENCE: 15
ggagctgtgg tgtctcagca cccctcttgg gtcatctgca agagcggcac cagcgtgaag      60
atcgagtgca gaagcctgga cttccaggcc accaccatgt tttggtacag gcagttcccc     120
aagcagagcc tgatgctgat ggccacctct aacgagggca gcaaggccac atatgagcag     180
ggcgtcgaga aggacaagtt cctgatcaac cacgccagcc tgacactgag caccctgaca     240
gtgacaagcg cccatcctga ggacagcagc ttctacatct gcagcgccag ggatctgaca     300
agcggcgcca caacgagca gttctttggc cctggcacca ggctgacagt gctc            354

<210> SEQ ID NO 16
<211> LENGTH: 759
<212> TYPE: DNA
<213> ORGANISM: Artificial Sequence
<220> FEATURE:
<223> OTHER INFORMATION: sequence encoding TCR alpha chain

<400> SEQUENCE: 16
agccagcagg gcgaagagga tccccaggct ctgtctattc aagagggcga gaacgccacc      60
atgaactgca gctacaagac cagcatcaac aacctgcagt ggtacagaca gaacagcggc     120
agaggactgg tgcacctgat cctgatcaga agcaacgaga gagagaagca ctccggcaga     180
ctgagagtga ccctggacac cagcaagaag tccagcagcc tgctgatcac agccagcaga     240
gccgccgata ccgccagcta cttttgtgcc accgatacca cctccggcac ctacaagtac     300
atcttcggca ccggcaccag actgaaggtg ctggccaaca ttcagaaccc cgatcctgcc     360
gtgtaccagc tgagagacag caagagcagc gacaagagcg tgtgcctgtt caccgacttc     420
gacagccaga ccaacgtgtc ccagagcaag gactccgatg tgtatatcac cgacaagacc     480
gtgctggaca tgcggagcat ggacttcaag agcaacagcg ccgtggcctg gtccaacaag     540
agcgatttcg cctgcgccaa cgccttcaac aacagcatta tccccgagga cacattcttc     600
ccaagtcctg agagcagctg cgacgtgaag ctggtggaaa agagcttcga gacagacacc     660
aacctgaact tccagaacct gagcgtgatc ggcttcagaa tcctgctgct gaaggtggcc     720
ggcttcaacc tgctgatgac cctgagactt tggagcagc                            759

<210> SEQ ID NO 17
<211> LENGTH: 891
<212> TYPE: DNA
<213> ORGANISM: Artificial Sequence
<220> FEATURE:
<223> OTHER INFORMATION: sequence encoding TCR beta chain

<400> SEQUENCE: 17
ggagctgtgg tgtctcagca cccctcttgg gtcatctgca agagcggcac cagcgtgaag      60
atcgagtgca gaagcctgga cttccaggcc accaccatgt tttggtacag gcagttcccc     120
aagcagagcc tgatgctgat ggccacctct aacgagggca gcaaggccac atatgagcag     180
ggcgtcgaga aggacaagtt cctgatcaac cacgccagcc tgacactgag caccctgaca     240
gtgacaagcg cccatcctga ggacagcagc ttctacatct gcagcgccag ggatctgaca     300
agcggcgcca caacgagca gttctttggc cctggcacca ggctgacagt gctcgaggac     360
ctgaagaacg tgttcccacc tgaggtggcc gtgttcgagc cttctgaggc cgagatctgt     420
cacacccaga aagccacact cgtgtgtctg gccaccggct ctacccccga tcacgtggaa     480
ctgtcttggt gggtcaacgg caaagaggtg cacagcggcg tcagcacaga tccccagcca     540

```
ctgaaagaac agcccgctct gaacgacagc cggtactgtc tgtctagccg gctgagagtg      600
tccgccacct tctggcagaa ccccagaaac cacttcagat gccaggtgca gttctacggc      660
ctgagcgaga cgatgagtg gacccaggat agagccaagc ctgtgacaca gatcgtgtct      720
gccgaagcct ggggcagagc cgattgtggc tttaccagcg agagctacca gcaaggcgtg      780
ctgtctgcca ccatcctgta cgagatcctg ctgggcaaag ccactctgta cgccgtgctg      840
gtttctgccc tggtcctgat ggctatggtc aagcggaagg actctagagg c             891
```

<210> SEQ ID NO 18
<211> LENGTH: 431
<212> TYPE: PRT
<213> ORGANISM: Homo sapiens

<400> SEQUENCE: 18

```
Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
            275                 280                 285

Gly Pro Val Val Pro Ala Trp Ser Gly Pro Arg Glu Ala Pro Asp Ser
        290                 295                 300

Leu Phe Ala Val Arg Arg His Leu Trp Gly Ser His Gly Asn Ser Thr
```

```
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
                340                 345                 350

Ala Pro Glu Lys Gln Arg Thr Leu Asn Glu Ile Tyr His Trp Phe Thr
                355                 360                 365

Arg Met Phe Ala Phe Phe Arg Asn His Pro Ala Thr Trp Lys Asn Ala
            370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro
                420                 425                 430

<210> SEQ ID NO 19
<211> LENGTH: 441
<212> TYPE: PRT
<213> ORGANISM: Artificial Sequence
<220> FEATURE:
<223> OTHER INFORMATION: FOXP3 polypeptide sequence

<400> SEQUENCE: 19

Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
                20                  25                  30

Ser Asp Leu Leu Gly Ala Arg Gly Pro Gly Gly Thr Phe Gln Gly Arg
            35                  40                  45

Asp Leu Arg Gly Gly Ala His Ala Ser Ser Ser Ser Leu Asn Pro Met
        50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
            115                 120                 125

Ile Ser Leu Thr Pro Pro Thr Thr Ala Thr Gly Val Phe Ser Leu Lys
        130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
                180                 185                 190

Leu Leu Ala Asn Gly Val Cys Lys Trp Pro Gly Cys Glu Lys Val Phe
            195                 200                 205

Glu Glu Pro Glu Asp Phe Leu Lys His Cys Gln Ala Asp His Leu Leu
        210                 215                 220

Asp Glu Lys Gly Arg Ala Gln Cys Leu Leu Gln Arg Glu Met Val Gln
225                 230                 235                 240

Ser Leu Glu Gln Val Glu Glu Leu Ser Ala Met Gln Ala His Leu Ala
```

```
                  245                250                255
Gly Lys Met Ala Leu Thr Lys Ala Ser Ser Val Ala Ser Ser Asp Lys
            260                265                270
Gly Ser Cys Cys Ile Val Ala Ala Gly Ser Gln Gly Pro Val Val Pro
            275                280                285
Ala Trp Ser Gly Pro Arg Glu Ala Pro Asp Ser Leu Phe Ala Val Arg
            290                295                300
Arg His Leu Trp Gly Ser His Gly Asn Ser Thr Phe Pro Glu Phe Leu
        305                310                315                320
His Asn Met Asp Tyr Phe Lys Phe His Asn Met Arg Pro Pro Phe Thr
                325                330                335
Tyr Ala Thr Leu Ile Arg Trp Ala Ile Leu Glu Ala Pro Glu Lys Gln
            340                345                350
Arg Thr Leu Asn Glu Ile Tyr His Trp Phe Thr Arg Met Phe Ala Phe
            355                360                365
Phe Arg Asn His Pro Ala Thr Trp Lys Asn Ala Ile Arg His Asn Leu
        370                375                380
Ser Leu His Lys Cys Phe Val Arg Val Glu Ser Glu Lys Gly Ala Val
        385                390                395                400
Trp Thr Val Asp Glu Leu Glu Phe Arg Lys Lys Arg Ser Gln Arg Pro
                405                410                415
Ser Arg Cys Ser Asn Pro Thr Pro Gly Pro Glu Gly Arg Gly Ser Leu
            420                425                430
Leu Thr Cys Gly Asp Val Glu Glu Asn
            435                440

<210> SEQ ID NO 20
<211> LENGTH: 1296
<212> TYPE: DNA
<213> ORGANISM: Homo sapiens

<400> SEQUENCE: 20
atgcccaacc ccaggcctgg caagccctcg gccccttcct tggcccttgg cccatcccca     60
ggagcctcgc ccagctggag ggctgcaccc aaagcctcag acctgctggg ggcccggggc    120
ccagggggaa ccttccaggg ccgagatctt cgaggcgggg cccatgcctc ctcttcttcc    180
ttgaacccca tgccaccatc gcagctgcag ctgcccacac tgcccctagt catggtggca    240
ccctccgggg cacggctggg cccccttgccc cacttacagg cactcctcca ggacaggcca    300
catttcatgc accagctctc aacggtggat gcccacgccc ggacccctgt gctgcaggtg    360
caccccctgg agagcccagc catgatcagc ctcacaccac ccaccaccgc cactgggtc     420 ttctccctca aggcccggcc tggcctccca cctgggatca acgtggccag cctggaatgg    480
gtgtccaggg agccggcact gctctgcacc ttcccaaatc ccagtgcacc caggaaggac    540
agcacccttt cggctgtgcc ccagagctcc tacccactgc tggcaaatgg tgtctgcaag    600
tggcccggat gtgagaaggt cttcgaagag ccagaggact tcctcaagca ctgccaggcg    660
gaccatcttc tggatgagaa gggcagggca caatgtctcc tccagagaga gatggtacag    720
tctctggagc agcagctggt gctggagaag gagaagctga gtgccatgca ggcccacctg    780
gctgggaaaa tggcactgac caaggcttca tctgtggcat catccgacaa gggctcctgc    840
tgcatcgtag ctgctggcag ccaaggccct gtcgtccag cctggtctgg ccccgggag     900 gcccctgaca gcctgtttgc tgtccggagg cacctgtggg gtagccatgg aaacagcaca    960
ttcccagagt tcctccacaa catggactac ttcaagttcc acaacatgcg accccctttc   1020
```

```
acctacgcca cgctcatccg ctgggccatc ctggaggctc cagagaagca gcggacactc    1080
aatgagatct accactggtt cacacgcatg tttgccttct tcagaaacca tcctgccacc    1140
tggaagaacg ccatccgcca caacctgagt ctgcacaagt gctttgtgcg ggtggagagc    1200
gagaaggggg ctgtgtggac cgtggatgag ctggagttcc gcaagaaacg gagccagagg    1260
cccagcaggt gttccaaccc tacacctggc ccctga                              1296

<210> SEQ ID NO 21
<211> LENGTH: 1352
<212> TYPE: DNA
<213> ORGANISM: Artificial Sequence
<220> FEATURE:
<223> OTHER INFORMATION: sequence encoding the FOXP3 polypeptide

<400> SEQUENCE: 21
gaattcgtcg acatgcccaa ccccagaccc ggcaagcctt ctgccccttc tctggccctg      60
ggaccatctc ctggcgcctc cccatcttgg agagccgccc ctaaagccag cgatctgctg     120
ggagctagag gccctggcgg cacattccag ggcagagatc tgagaggcgg agcccacgcc     180
tctagcagca gcctgaatcc catgccccct agccagctgc agctgcctac actgcctctc     240
gtgatggtgg cccctagcgg agctagactg ggccctctgc ctcatctgca ggctctgctg     300
caggaccggc cccactttat gcaccagctg agcaccgtgg acgcccacgc cagaacacct     360
gtgctgcagg tgcacccct ggaaagccct gccatgatca gcctgacccc tccaaccaca      420
gccaccggcg tgttcagcct gaaggccaga cctggactgc ccctggcat caatgtggcc      480 agcctggaat gggtgtcccg cgaacctgcc ctgctgtgca ccttccccaa tcctagcgcc     540
cccagaaagg acagcacact gtctgccgtg ccccagagca gctatcccct gctggctaac     600
ggcgtgtgca agtggcctgg ctgcgagaag gtgttcgagg aacccgagga cttcctgaag     660
cactgccagg ccgaccatct gctggacgag aaaggcagag cccagtgcct gctgcagcgc     720
gagatggtgc agtccctgga acagcagctg gtgctggaaa agaaaagct gagcgccatg      780 caggcccacc tggccggaaa gatggccctg acaaaagcca gcagcgtggc cagctccgac     840
aagggcagct gttgtatcgt ggccgctggc agccagggac ctgtggtgcc tgcttggagc     900
ggacctagag aggcccccga tagcctgttt gccgtgcgga gacacctgtg gggcagccac     960
ggcaactcta ccttccccga gttcctgcac aacatggact acttcaagtt ccacaacatg    1020
aggcccccct tcacctacgc caccctgatc agatgggcca ttctggaagc ccccgagaag    1080
cagcggaccc tgaacgagat ctaccactgg tttacccgga tgttcgcctt cttccggaac    1140 cacccgcca cctggaagaa cgccatccgg cacaatctga gcctgcacaa gtgcttcgtg     1200
cgggtggaaa gcgagaaggg cgccgtgtgg acagtggacg agctggaatt cggaagaag     1260 cggtcccaga ggcccagccg gtgtagcaat cctacacctg ccctgagggg cagaggaagt    1320
ctgctaacat gcggtgacgt cgaggagaat cc                                  1352

<210> SEQ ID NO 22
<211> LENGTH: 20
<212> TYPE: PRT
<213> ORGANISM: Artificial Sequence
<220> FEATURE:
<223> OTHER INFORMATION: leader sequence

<400> SEQUENCE: 22

Met Glu Thr Leu Leu Gly Val Ser Leu Val Ile Leu Trp Leu Gln Leu
1               5                   10                  15
```

-continued

```
Ala Arg Val Asn
          20

<210> SEQ ID NO 23
<211> LENGTH: 25
<212> TYPE: PRT
<213> ORGANISM: Artificial Sequence
<220> FEATURE:
<223> OTHER INFORMATION: leader sequence

<400> SEQUENCE: 23

Met Leu Leu Leu Leu Leu Leu Leu Gly Pro Gly Ile Ser Leu Leu Leu
1               5                   10                  15

Pro Gly Ser Leu Ala Gly Ser Gly Leu
          20                  25

<210> SEQ ID NO 24
<211> LENGTH: 452
<212> TYPE: PRT
<213> ORGANISM: Artificial Sequence
<220> FEATURE:
<223> OTHER INFORMATION: FOXP3-2A polypeptide (FOXP3 polypeptide-2A
      self-cleaving peptide)

<400> SEQUENCE: 24

Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
          20                  25                  30

Ser Asp Leu Leu Gly Ala Arg Gly Pro Gly Gly Thr Phe Gln Gly Arg
          35                  40                  45

Asp Leu Arg Gly Gly Ala His Ala Ser Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
              85                  90                  95

Gln Asp Arg Pro His Phe Met His Gln Leu Ser Thr Val Asp Ala His
              100                 105                 110

Ala Arg Thr Pro Val Leu Gln Val His Pro Leu Glu Ser Pro Ala Met
          115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
              165                 170                 175

Pro Arg Lys Asp Ser Thr Leu Ser Ala Val Pro Gln Ser Ser Tyr Pro
              180                 185                 190

Leu Leu Ala Asn Gly Val Cys Lys Trp Pro Gly Cys Glu Lys Val Phe
              195                 200                 205

Glu Glu Pro Glu Asp Phe Leu Lys His Cys Gln Ala Asp His Leu Leu
          210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
              245                 250                 255
```

-continued

```
Gln Ala His Leu Ala Gly Lys Met Ala Leu Thr Lys Ala Ser Ser Val
        260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
        290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
        340                 345                 350

Ala Pro Glu Lys Gln Arg Thr Leu Asn Glu Ile Tyr His Trp Phe Thr
        355                 360                 365

Arg Met Phe Ala Phe Phe Arg Asn His Pro Ala Thr Trp Lys Asn Ala
        370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro Gly
        420                 425                 430

Ala Thr Asn Phe Ser Leu Leu Lys Gln Ala Gly Asp Val Glu Glu Asn
        435                 440                 445

Pro Gly Pro Ser
    450
```

```
<210> SEQ ID NO 25
<211> LENGTH: 462
<212> TYPE: PRT
<213> ORGANISM: Artificial Sequence
<220> FEATURE:
<223> OTHER INFORMATION: FOXP3-2A polypeptide (FOXP3 polypeptide-2A
      self-cleaving peptide)

<400> SEQUENCE: 25

Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
                20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
        130                 135                 140

Ala Arg Pro Gly Leu Pro Pro Gly Ile Asn Val Ala Ser Leu Glu Trp
145                 150                 155                 160
```

-continued

```
Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Val Glu Glu Leu Ser Ala Met Gln Ala His Leu Ala
                245                 250                 255

Gly Lys Met Ala Leu Thr Lys Ala Ser Ser Val Ala Ser Ser Asp Lys
                260                 265                 270

Gly Ser Cys Cys Ile Val Ala Ala Gly Ser Gln Gly Pro Val Val Pro
            275                 280                 285

Ala Trp Ser Gly Pro Arg Glu Ala Pro Asp Ser Leu Phe Ala Val Arg
        290                 295                 300

Arg His Leu Trp Gly Ser His Gly Asn Ser Thr Phe Pro Glu Phe Leu
305                 310                 315                 320

His Asn Met Asp Tyr Phe Lys Phe His Asn Met Arg Pro Pro Phe Thr
                325                 330                 335

Tyr Ala Thr Leu Ile Arg Trp Ala Ile Leu Glu Ala Pro Glu Lys Gln
                340                 345                 350

Arg Thr Leu Asn Glu Ile Tyr His Trp Phe Thr Arg Met Phe Ala Phe
            355                 360                 365

Phe Arg Asn His Pro Ala Thr Trp Lys Asn Ala Ile Arg His Asn Leu
        370                 375                 380

Ser Leu His Lys Cys Phe Val Arg Val Glu Ser Glu Lys Gly Ala Val
385                 390                 395                 400

Trp Thr Val Asp Glu Leu Glu Phe Arg Lys Lys Arg Ser Gln Arg Pro
                405                 410                 415

Ser Arg Cys Ser Asn Pro Thr Pro Gly Pro Glu Gly Arg Gly Ser Leu
            420                 425                 430

Leu Thr Cys Gly Asp Val Glu Glu Asn Gly Ala Thr Asn Phe Ser Leu
        435                 440                 445

Leu Lys Gln Ala Gly Asp Val Glu Glu Asn Pro Gly Pro Ser
    450                 455                 460
```

```
<210> SEQ ID NO 26
<211> LENGTH: 6
<212> TYPE: PRT
<213> ORGANISM: Artificial Sequence
<220> FEATURE:
<223> OTHER INFORMATION: MBP111-129/DR4 TCR HD1-14 alpha chain CDR

<400> SEQUENCE: 26

Val Ser Gly Leu Arg Gly
1               5

<210> SEQ ID NO 27
<211> LENGTH: 7
<212> TYPE: PRT
<213> ORGANISM: Artificial Sequence
<220> FEATURE:
<223> OTHER INFORMATION: MBP111-129/DR4 TCR HD1-14 alpha chain CDR
```

```
<400> SEQUENCE: 27

Leu Tyr Ser Ala Gly Glu Glu
1               5

<210> SEQ ID NO 28
<211> LENGTH: 12
<212> TYPE: PRT
<213> ORGANISM: Artificial Sequence
<220> FEATURE:
<223> OTHER INFORMATION: MBP111-129/DR4 TCR HD1-14 alpha chain CDR

<400> SEQUENCE: 28

Ala Val Gln Gly Ala Gly Gly Tyr Gln Lys Val Thr
1               5                   10

<210> SEQ ID NO 29
<211> LENGTH: 5
<212> TYPE: PRT
<213> ORGANISM: Artificial Sequence
<220> FEATURE:
<223> OTHER INFORMATION: MBP111-129/DR4 TCR HD1-14 beta chain CDR

<400> SEQUENCE: 29

Met Asn His Asn Ser
1               5

<210> SEQ ID NO 30
<211> LENGTH: 6
<212> TYPE: PRT
<213> ORGANISM: Artificial Sequence
<220> FEATURE:
<223> OTHER INFORMATION: MBP111-129/DR4 TCR HD1-14 beta chain CDR

<400> SEQUENCE: 30

Ser Ala Ser Glu Gly Thr
1               5

<210> SEQ ID NO 31
<211> LENGTH: 10
<212> TYPE: PRT
<213> ORGANISM: Artificial Sequence
<220> FEATURE:
<223> OTHER INFORMATION: MBP111-129/DR4 TCR HD1-14 beta chain CDR

<400> SEQUENCE: 31

Ala Ser Ser Glu Trp Ala Ser Gly Tyr Thr
1               5                   10

<210> SEQ ID NO 32
<211> LENGTH: 112
<212> TYPE: PRT
<213> ORGANISM: Artificial Sequence
<220> FEATURE:
<223> OTHER INFORMATION: MBP111-129/DR4 TCR HD1-14 alpha variable

<400> SEQUENCE: 32

Glu Asp Gln Val Thr Gln Ser Pro Glu Ala Leu Arg Leu Gln Glu Gly
1               5                   10                  15

Glu Ser Ser Ser Leu Asn Cys Ser Tyr Thr Val Ser Gly Leu Arg Gly
                20                  25                  30

Leu Phe Trp Tyr Arg Gln Asp Pro Gly Lys Gly Pro Glu Phe Leu Phe
            35                  40                  45

Thr Leu Tyr Ser Ala Gly Glu Glu Lys Glu Lys Glu Arg Leu Lys Ala
        50                  55                  60
```

```
Thr Leu Thr Lys Lys Glu Ser Phe Leu His Ile Thr Ala Pro Lys Pro
65              70              75              80

Glu Asp Ser Ala Thr Tyr Leu Cys Ala Val Gln Gly Ala Gly Gly Tyr
                85              90              95

Gln Lys Val Thr Phe Gly Ile Gly Thr Lys Leu Gln Val Ile Pro Asn
            100             105             110
```

<210> SEQ ID NO 33
<211> LENGTH: 111
<212> TYPE: PRT
<213> ORGANISM: Artificial Sequence
<220> FEATURE:
<223> OTHER INFORMATION: MBP111-129/DR4 TCR HD1-14 beta variable

<400> SEQUENCE: 33

```
Asn Ala Gly Val Thr Gln Thr Pro Lys Phe Gln Val Leu Lys Thr Gly
1               5               10              15

Gln Ser Met Thr Leu Gln Cys Ala Gln Asp Met Asn His Asn Ser Met
                20              25              30

Tyr Trp Tyr Arg Gln Asp Pro Gly Met Gly Leu Arg Leu Ile Tyr Tyr
            35              40              45

Ser Ala Ser Glu Gly Thr Thr Asp Lys Gly Glu Val Pro Asn Gly Tyr
        50              55              60

Asn Val Ser Arg Leu Asn Lys Arg Glu Phe Ser Leu Arg Leu Glu Ser
65              70              75              80

Ala Ala Pro Ser Gln Thr Ser Val Tyr Phe Cys Ala Ser Ser Glu Trp
                85              90              95

Ala Ser Gly Tyr Thr Phe Gly Ser Gly Thr Arg Leu Thr Val Val
            100             105             110
```

<210> SEQ ID NO 34
<211> LENGTH: 6
<212> TYPE: PRT
<213> ORGANISM: Artificial Sequence
<220> FEATURE:
<223> OTHER INFORMATION: MBP111-129/DR4 TCR MS3-1 alpha chain CDR

<400> SEQUENCE: 34

```
Val Ser Gly Leu Arg Gly
1               5
```

<210> SEQ ID NO 35
<211> LENGTH: 7
<212> TYPE: PRT
<213> ORGANISM: Artificial Sequence
<220> FEATURE:
<223> OTHER INFORMATION: MBP111-129/DR4 TCR MS3-1 alpha chain CDR

<400> SEQUENCE: 35

```
Leu Tyr Ser Ala Gly Glu Glu
1               5
```

<210> SEQ ID NO 36
<211> LENGTH: 12
<212> TYPE: PRT
<213> ORGANISM: Artificial Sequence
<220> FEATURE:
<223> OTHER INFORMATION: MBP111-129/DR4 TCR MS3-1 alpha chain CDR

<400> SEQUENCE: 36

```
Ala Ala Tyr Gly Ser Ser Asn Thr Gly Lys Leu Ile
1               5               10
```

```
<210> SEQ ID NO 37
<211> LENGTH: 6
<212> TYPE: PRT
<213> ORGANISM: Artificial Sequence
<220> FEATURE:
<223> OTHER INFORMATION: MBP111-129/DR4 TCR MS3-1 beta chain CDR

<400> SEQUENCE: 37

Gly Thr Ser Asn Pro Asn
1               5

<210> SEQ ID NO 38
<211> LENGTH: 5
<212> TYPE: PRT
<213> ORGANISM: Artificial Sequence
<220> FEATURE:
<223> OTHER INFORMATION: MBP111-129/DR4 TCR MS3-1 beta chain CDR

<400> SEQUENCE: 38

Ser Val Gly Ile Gly
1               5

<210> SEQ ID NO 39
<211> LENGTH: 13
<212> TYPE: PRT
<213> ORGANISM: Artificial Sequence
<220> FEATURE:
<223> OTHER INFORMATION: MBP111-129/DR4 TCR MS3-1 beta chain CDR

<400> SEQUENCE: 39

Ala Trp Ser Ala Pro Gly Thr Ala Tyr Thr Glu Ala Phe
1               5                   10

<210> SEQ ID NO 40
<211> LENGTH: 112
<212> TYPE: PRT
<213> ORGANISM: Artificial Sequence
<220> FEATURE:
<223> OTHER INFORMATION: MBP111-129/DR4 TCR MS3-1 alpha variable

<400> SEQUENCE: 40

Glu Asp Gln Val Thr Gln Ser Pro Glu Ala Leu Arg Leu Gln Glu Gly
1               5                   10                  15

Glu Ser Ser Ser Leu Asn Cys Ser Tyr Thr Val Ser Gly Leu Arg Gly
                20                  25                  30

Leu Phe Trp Tyr Arg Gln Asp Pro Gly Lys Gly Pro Glu Phe Leu Phe
        35                  40                  45

Thr Leu Tyr Ser Ala Gly Glu Glu Lys Glu Lys Glu Arg Leu Lys Ala
    50                  55                  60

Thr Leu Thr Lys Lys Glu Ser Phe Leu His Ile Thr Ala Pro Lys Pro
65                  70                  75                  80

Glu Asp Ser Ala Thr Tyr Leu Cys Ala Ala Tyr Gly Ser Ser Asn Thr
                85                  90                  95

Gly Lys Leu Ile Phe Gly Gln Gly Thr Thr Leu Gln Val Lys Pro Asp
            100                 105                 110

<210> SEQ ID NO 41
<211> LENGTH: 114
<212> TYPE: PRT
<213> ORGANISM: Artificial Sequence
<220> FEATURE:
<223> OTHER INFORMATION: MBP111-129/DR4 TCR MS3-1 beta variable

<400> SEQUENCE: 41
```

```
Ser Gln Thr Ile His Gln Trp Pro Ala Thr Leu Val Gln Pro Val Gly
1               5                   10                  15

Ser Pro Leu Ser Leu Glu Cys Thr Val Glu Gly Thr Ser Asn Pro Asn
            20                  25                  30

Leu Tyr Trp Tyr Arg Gln Ala Ala Gly Arg Gly Leu Gln Leu Leu Phe
        35                  40                  45

Tyr Ser Val Gly Ile Gly Gln Ile Ser Ser Glu Val Pro Gln Asn Leu
    50                  55                  60

Ser Ala Ser Arg Pro Gln Asp Arg Gln Phe Ile Leu Ser Ser Lys Lys
65                  70                  75                  80

Leu Leu Leu Ser Asp Ser Gly Phe Tyr Leu Cys Ala Trp Ser Ala Pro
                85                  90                  95

Gly Thr Ala Tyr Thr Glu Ala Phe Phe Gly Gln Gly Thr Arg Leu Thr
            100                 105                 110

Val Val
```

```
<210> SEQ ID NO 42
<211> LENGTH: 6
<212> TYPE: PRT
<213> ORGANISM: Artificial Sequence
<220> FEATURE:
<223> OTHER INFORMATION: MBP111-129/DR4 TCR MS3-11 alpha chain CDR

<400> SEQUENCE: 42

Ser Ser Val Pro Pro Tyr
1               5
```

```
<210> SEQ ID NO 43
<211> LENGTH: 8
<212> TYPE: PRT
<213> ORGANISM: Artificial Sequence
<220> FEATURE:
<223> OTHER INFORMATION: MBP111-129/DR4 TCR MS3-11 alpha chain CDR

<400> SEQUENCE: 43

Tyr Thr Ser Ala Ala Thr Leu Val
1               5
```

```
<210> SEQ ID NO 44
<211> LENGTH: 8
<212> TYPE: PRT
<213> ORGANISM: Artificial Sequence
<220> FEATURE:
<223> OTHER INFORMATION: MBP111-129/DR4 TCR MS3-11 alpha chain CDR

<400> SEQUENCE: 44

Ala Val Met His Asn Asp Met Arg
1               5
```

```
<210> SEQ ID NO 45
<211> LENGTH: 5
<212> TYPE: PRT
<213> ORGANISM: Artificial Sequence
<220> FEATURE:
<223> OTHER INFORMATION: MBP111-129/DR4 TCR MS3-11 beta chain CDR

<400> SEQUENCE: 45

Met Asn His Glu Tyr
1               5
```

```
<210> SEQ ID NO 46
<211> LENGTH: 6
```

<212> TYPE: PRT
<213> ORGANISM: Artificial Sequence
<220> FEATURE:
<223> OTHER INFORMATION: MBP111-129/DR4 TCR MS3-11 beta chain CDR

<400> SEQUENCE: 46

Ser Val Gly Ala Gly Ile
1               5

<210> SEQ ID NO 47
<211> LENGTH: 14
<212> TYPE: PRT
<213> ORGANISM: Artificial Sequence
<220> FEATURE:
<223> OTHER INFORMATION: MBP111-129/DR4 TCR MS3-11 beta chain CDR

<400> SEQUENCE: 47

Ala Ser Arg Thr Gly Thr Gly Arg Ala Ser Thr Glu Ala Phe
1               5                   10

<210> SEQ ID NO 48
<211> LENGTH: 111
<212> TYPE: PRT
<213> ORGANISM: Artificial Sequence
<220> FEATURE:
<223> OTHER INFORMATION: MBP111-129/DR4 TCR MS3-11 alpha variable

<400> SEQUENCE: 48

Ala Gln Ser Val Thr Gln Leu Gly Ser His Val Ser Val Ser Glu Gly
1               5                   10                  15

Ala Leu Val Leu Leu Arg Cys Asn Tyr Ser Ser Ser Val Pro Pro Tyr
                20                  25                  30

Leu Phe Trp Tyr Val Gln Tyr Pro Asn Gln Gly Leu Gln Leu Leu Leu
            35                  40                  45

Lys Tyr Thr Ser Ala Ala Thr Leu Val Lys Gly Ile Asn Gly Phe Glu
        50                  55                  60

Ala Glu Phe Lys Lys Ser Glu Thr Ser Phe His Leu Thr Lys Pro Ser
65                  70                  75                  80

Ala His Met Ser Asp Ala Ala Glu Tyr Phe Cys Ala Val Met His Asn
                85                  90                  95

Asp Met Arg Phe Gly Ala Gly Thr Arg Leu Thr Val Lys Pro Asn
            100                 105                 110

<210> SEQ ID NO 49
<211> LENGTH: 115
<212> TYPE: PRT
<213> ORGANISM: Artificial Sequence
<220> FEATURE:
<223> OTHER INFORMATION: MBP111-129/DR4 TCR MS3-11 beta variable

<400> SEQUENCE: 49

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
                20                  25                  30

Ser Trp Tyr Arg Gln Asp Pro Gly Met Gly Leu Arg Leu Ile His Tyr
        35                  40                  45

Ser Val Gly Ala Gly Ile Thr Asp Gln Gly Glu Val Pro Asn Gly Tyr
        50                  55                  60

Asn Val Ser Arg Ser Thr Thr Glu Asp Phe Pro Leu Arg Leu Leu Ser
65                  70                  75                  80

```
Ala Ala Pro Ser Gln Thr Ser Val Tyr Phe Cys Ala Ser Arg Thr Gly
                85                  90                  95

Thr Gly Arg Ala Ser Thr Glu Ala Phe Phe Gly Gln Gly Thr Arg Leu
            100                 105                 110

Thr Val Val
        115

<210> SEQ ID NO 50
<211> LENGTH: 6
<212> TYPE: PRT
<213> ORGANISM: Artificial Sequence
<220> FEATURE:
<223> OTHER INFORMATION: MBP111-129/DR4 TCR MS1-4H12 alpha chain CDR

<400> SEQUENCE: 50

Val Ser Gly Leu Arg Gly
1               5

<210> SEQ ID NO 51
<211> LENGTH: 7
<212> TYPE: PRT
<213> ORGANISM: Artificial Sequence
<220> FEATURE:
<223> OTHER INFORMATION: MBP111-129/DR4 TCR MS1-4H12 alpha chain CDR

<400> SEQUENCE: 51

Leu Tyr Ser Ala Gly Glu Glu
1               5

<210> SEQ ID NO 52
<211> LENGTH: 12
<212> TYPE: PRT
<213> ORGANISM: Artificial Sequence
<220> FEATURE:
<223> OTHER INFORMATION: MBP111-129/DR4 TCR MS1-4H12 alpha chain CDR

<400> SEQUENCE: 52

Ala Val Gln Ala Asn Asn Tyr Gly Gln Asn Phe Val
1               5                   10

<210> SEQ ID NO 53
<211> LENGTH: 5
<212> TYPE: PRT
<213> ORGANISM: Artificial Sequence
<220> FEATURE:
<223> OTHER INFORMATION: MBP111-129/DR4 TCR MS1-4H12 beta chain CDR

<400> SEQUENCE: 53

Leu Gly His Asn Ala
1               5

<210> SEQ ID NO 54
<211> LENGTH: 6
<212> TYPE: PRT
<213> ORGANISM: Artificial Sequence
<220> FEATURE:
<223> OTHER INFORMATION: MBP111-129/DR4 TCR MS1-4H12 beta chain CDR

<400> SEQUENCE: 54

Tyr Ser Leu Glu Glu Arg
1               5

<210> SEQ ID NO 55
<211> LENGTH: 14
<212> TYPE: PRT
<213> ORGANISM: Artificial Sequence
```

<220> FEATURE:
<223> OTHER INFORMATION: MBP111-129/DR4 TCR MS1-4H12 beta chain CDR

<400> SEQUENCE: 55

Ala Ser Ser Gln Gly Pro Ser Gly Asn Thr Gly Glu Leu Phe
1               5                   10

<210> SEQ ID NO 56
<211> LENGTH: 112
<212> TYPE: PRT
<213> ORGANISM: Artificial Sequence
<220> FEATURE:
<223> OTHER INFORMATION: MBP111-129/DR4 TCR MS1-4H12 alpha variable

<400> SEQUENCE: 56

Glu Asp Gln Val Thr Gln Ser Pro Glu Ala Leu Arg Leu Gln Glu Gly
1               5                   10                  15

Glu Ser Ser Ser Leu Asn Cys Ser Tyr Thr Val Ser Gly Leu Arg Gly
                20                  25                  30

Leu Phe Trp Tyr Arg Gln Asp Pro Gly Lys Gly Pro Glu Phe Leu Phe
            35                  40                  45

Thr Leu Tyr Ser Ala Gly Glu Glu Lys Glu Lys Glu Arg Leu Lys Ala
        50                  55                  60

Thr Leu Thr Lys Lys Glu Ser Phe Leu His Ile Thr Ala Pro Lys Pro
65                  70                  75                  80

Glu Asp Ser Ala Thr Tyr Leu Cys Ala Val Gln Ala Asn Asn Tyr Gly
                85                  90                  95

Gln Asn Phe Val Phe Gly Pro Gly Thr Arg Leu Ser Val Leu Pro Tyr
                100                 105                 110

<210> SEQ ID NO 57
<211> LENGTH: 115
<212> TYPE: PRT
<213> ORGANISM: Artificial Sequence
<220> FEATURE:
<223> OTHER INFORMATION: MBP111-129/DR4 TCR MS1-4H12 beta variable

<400> SEQUENCE: 57

Glu Thr Gly Val Thr Gln Thr Pro Arg His Leu Val Met Gly Met Thr
1               5                   10                  15

Asn Lys Lys Ser Leu Lys Cys Glu Gln His Leu Gly His Asn Ala Met
                20                  25                  30

Tyr Trp Tyr Lys Gln Ser Ala Lys Lys Pro Leu Glu Leu Met Phe Val
            35                  40                  45

Tyr Ser Leu Glu Glu Arg Val Glu Asn Asn Ser Val Pro Ser Arg Phe
        50                  55                  60

Ser Pro Glu Cys Pro Asn Ser Ser His Leu Phe Leu His Leu His Thr
65                  70                  75                  80

Leu Gln Pro Glu Asp Ser Ala Leu Tyr Leu Cys Ala Ser Ser Gln Gly
                85                  90                  95

Pro Ser Gly Asn Thr Gly Glu Leu Phe Phe Gly Glu Gly Ser Arg Leu
                100                 105                 110

Thr Val Leu
        115

<210> SEQ ID NO 58
<211> LENGTH: 7
<212> TYPE: PRT
<213> ORGANISM: Artificial Sequence
<220> FEATURE:

<223> OTHER INFORMATION: MBP111-129/DR4 TCR HD-1C2 alpha chain CDR

<400> SEQUENCE: 58

Thr Ile Ser Gly Thr Asp Tyr
1               5

<210> SEQ ID NO 59
<211> LENGTH: 5
<212> TYPE: PRT
<213> ORGANISM: Artificial Sequence
<220> FEATURE:
<223> OTHER INFORMATION: MBP111-129/DR4 TCR HD-1C2 alpha chain CDR

<400> SEQUENCE: 59

Gly Leu Thr Ser Asn
1               5

<210> SEQ ID NO 60
<211> LENGTH: 12
<212> TYPE: PRT
<213> ORGANISM: Artificial Sequence
<220> FEATURE:
<223> OTHER INFORMATION: MBP111-129/DR4 TCR HD-1C2 alpha chain CDR

<400> SEQUENCE: 60

Ile Leu Arg Gly Arg Thr Ser Tyr Asp Lys Val Ile
1               5                   10

<210> SEQ ID NO 61
<211> LENGTH: 5
<212> TYPE: PRT
<213> ORGANISM: Artificial Sequence
<220> FEATURE:
<223> OTHER INFORMATION: MBP111-129/DR4 TCR HD-1C2 beta chain CDR

<400> SEQUENCE: 61

Met Gly His Arg Ala
1               5

<210> SEQ ID NO 62
<211> LENGTH: 6
<212> TYPE: PRT
<213> ORGANISM: Artificial Sequence
<220> FEATURE:
<223> OTHER INFORMATION: MBP111-129/DR4 TCR HD-1C2 beta chain CDR

<400> SEQUENCE: 62

Tyr Ser Tyr Glu Lys Leu
1               5

<210> SEQ ID NO 63
<211> LENGTH: 15
<212> TYPE: PRT
<213> ORGANISM: Artificial Sequence
<220> FEATURE:
<223> OTHER INFORMATION: MBP111-129/DR4 TCR HD-1C2 beta chain CDR

<400> SEQUENCE: 63

Ala Ser Ser Gln Gly Ser Gly Gly Gly Val Thr Gly Glu Leu Phe
1               5                   10                  15

<210> SEQ ID NO 64
<211> LENGTH: 112
<212> TYPE: PRT
<213> ORGANISM: Artificial Sequence
<220> FEATURE:
<223> OTHER INFORMATION: MBP111-129/DR4 TCR HD-1C2 alpha variable

<400> SEQUENCE: 64

Asp Ala Lys Thr Thr Gln Pro Asn Ser Met Glu Ser Asn Glu Glu Glu
1               5                   10                  15

Pro Val His Leu Pro Cys Asn His Ser Thr Ile Ser Gly Thr Asp Tyr
            20                  25                  30

Ile His Trp Tyr Arg Gln Leu Pro Ser Gln Gly Pro Glu Tyr Val Ile
        35                  40                  45

His Gly Leu Thr Ser Asn Val Asn Asn Arg Met Ala Ser Leu Ala Ile
    50                  55                  60

Ala Glu Asp Arg Lys Ser Ser Thr Leu Ile Leu His Arg Ala Thr Leu
65                  70                  75                  80

Arg Asp Ala Ala Val Tyr Tyr Cys Ile Leu Arg Gly Arg Thr Ser Tyr
                85                  90                  95

Asp Lys Val Ile Phe Gly Pro Gly Thr Ser Leu Ser Val Ile Pro Asn
            100                 105                 110

<210> SEQ ID NO 65
<211> LENGTH: 116
<212> TYPE: PRT
<213> ORGANISM: Artificial Sequence
<220> FEATURE:
<223> OTHER INFORMATION: MBP111-129/DR4 TCR HD-1C2 beta variable

<400> SEQUENCE: 65

Asp Thr Glu Val Thr Gln Thr Pro Lys His Leu Val Met Gly Met Thr
1               5                   10                  15

Asn Lys Lys Ser Leu Lys Cys Glu Gln His Met Gly His Arg Ala Met
            20                  25                  30

Tyr Trp Tyr Lys Gln Lys Ala Lys Lys Pro Pro Glu Leu Met Phe Val
        35                  40                  45

Tyr Ser Tyr Glu Lys Leu Ser Ile Asn Glu Ser Val Pro Ser Arg Phe
    50                  55                  60

Ser Pro Glu Cys Pro Asn Ser Ser Leu Leu Asn Leu His Leu His Ala
65                  70                  75                  80

Leu Gln Pro Glu Asp Ser Ala Leu Tyr Leu Cys Ala Ser Ser Gln Gly
                85                  90                  95

Ser Gly Gly Gly Val Thr Gly Glu Leu Phe Phe Gly Glu Gly Ser Arg
            100                 105                 110

Leu Thr Val Leu
        115

<210> SEQ ID NO 66
<211> LENGTH: 5
<212> TYPE: PRT
<213> ORGANISM: Artificial Sequence
<220> FEATURE:
<223> OTHER INFORMATION: MBP81-99 /DR15 TCR Ob-2F3 alpha chain CDR

<400> SEQUENCE: 66

Thr Ser Ile Asn Asn
1               5

<210> SEQ ID NO 67
<211> LENGTH: 7
<212> TYPE: PRT
<213> ORGANISM: Artificial Sequence
<220> FEATURE:
<223> OTHER INFORMATION: MBP81-99 /DR15 TCR Ob-2F3 alpha chain CDR

```
<400> SEQUENCE: 67

Ile Arg Ser Asn Glu Arg Glu
1               5

<210> SEQ ID NO 68
<211> LENGTH: 12
<212> TYPE: PRT
<213> ORGANISM: Artificial Sequence
<220> FEATURE:
<223> OTHER INFORMATION: MBP81-99 /DR15 TCR Ob-2F3 alpha chain CDR

<400> SEQUENCE: 68

Ala Thr Asp Ala Thr Ser Gly Thr Tyr Lys Tyr Ile
1               5                   10

<210> SEQ ID NO 69
<211> LENGTH: 6
<212> TYPE: PRT
<213> ORGANISM: Artificial Sequence
<220> FEATURE:
<223> OTHER INFORMATION: MBP81-99 /DR15 TCR Ob-2F3 beta chain CDR

<400> SEQUENCE: 69

Asp Phe Gln Ala Thr Thr
1               5

<210> SEQ ID NO 70
<211> LENGTH: 7
<212> TYPE: PRT
<213> ORGANISM: Artificial Sequence
<220> FEATURE:
<223> OTHER INFORMATION: MBP81-99 /DR15 TCR Ob-2F3 beta chain CDR

<400> SEQUENCE: 70

Ser Asn Glu Gly Ser Lys Ala
1               5

<210> SEQ ID NO 71
<211> LENGTH: 14
<212> TYPE: PRT
<213> ORGANISM: Artificial Sequence
<220> FEATURE:
<223> OTHER INFORMATION: MBP81-99 /DR15 TCR Ob-2F3 beta chain CDR

<400> SEQUENCE: 71

Ser Ala Arg Asp Leu Thr Ser Gly Ser Leu Asn Glu Gln Phe
1               5                   10

<210> SEQ ID NO 72
<211> LENGTH: 113
<212> TYPE: PRT
<213> ORGANISM: Artificial Sequence
<220> FEATURE:
<223> OTHER INFORMATION: MBP81-99 /DR15 TCR Ob-2F3 alpha variable

<400> SEQUENCE: 72

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
                20                  25                  30

Gln Trp Tyr Arg Gln Asn Ser Gly Arg Gly Leu Val His Leu Ile Leu
            35                  40                  45

Ile Arg Ser Asn Glu Arg Glu Lys His Ser Gly Arg Leu Arg Val Thr
        50                  55                  60
```

Leu Asp Thr Ser Lys Lys Ser Ser Ser Leu Leu Ile Thr Ala Ser Arg
65              70                  75                  80

Ala Ala Asp Thr Ala Ser Tyr Phe Cys Ala Thr Asp Ala Thr Ser Gly
                85                  90                  95

Thr Tyr Lys Tyr Ile Phe Gly Thr Gly Thr Arg Leu Lys Val Leu Ala
            100                 105                 110

Asn

<210> SEQ ID NO 73
<211> LENGTH: 118
<212> TYPE: PRT
<213> ORGANISM: Artificial Sequence
<220> FEATURE:
<223> OTHER INFORMATION: MBP81-99 /DR15 TCR Ob-2F3 beta variable

<400> SEQUENCE: 73

Gly Ala Val Val Ser Gln His Pro Ser Trp Val Ile Cys Lys Ser Gly
1               5                   10                  15

Thr Ser Val Lys Ile Glu Cys Arg Ser Leu Asp Phe Gln Ala Thr Thr
                20                  25                  30

Met Phe Trp Tyr Arg Gln Phe Pro Lys Gln Ser Leu Met Leu Met Ala
            35                  40                  45

Thr Ser Asn Glu Gly Ser Lys Ala Thr Tyr Glu Gln Gly Val Glu Lys
        50                  55                  60

Asp Lys Phe Leu Ile Asn His Ala Ser Leu Thr Leu Ser Thr Leu Thr
65                  70                  75                  80

Val Thr Ser Ala His Pro Glu Asp Ser Ser Phe Tyr Ile Cys Ser Ala
                85                  90                  95

Arg Asp Leu Thr Ser Gly Ser Leu Asn Glu Gln Phe Phe Gly Pro Gly
            100                 105                 110

Thr Arg Leu Thr Val Leu
        115

<210> SEQ ID NO 74
<211> LENGTH: 5
<212> TYPE: PRT
<213> ORGANISM: Artificial Sequence
<220> FEATURE:
<223> OTHER INFORMATION: MBP81-99 /DR15 TCR Ob-3D1 alpha chain CDR

<400> SEQUENCE: 74

Thr Ser Ile Asn Asn
1               5

<210> SEQ ID NO 75
<211> LENGTH: 7
<212> TYPE: PRT
<213> ORGANISM: Artificial Sequence
<220> FEATURE:
<223> OTHER INFORMATION: MBP81-99 /DR15 TCR Ob-3D1 alpha chain CDR

<400> SEQUENCE: 75

Ile Arg Ser Asn Glu Arg Glu
1               5

<210> SEQ ID NO 76
<211> LENGTH: 10
<212> TYPE: PRT
<213> ORGANISM: Artificial Sequence
<220> FEATURE:
<223> OTHER INFORMATION: MBP81-99 /DR15 TCR Ob-3D1 alpha chain CDR

<400> SEQUENCE: 76

Ala Thr Asp Gly Asn Gly Asn Gln Phe Tyr
1               5                   10

<210> SEQ ID NO 77
<211> LENGTH: 5
<212> TYPE: PRT
<213> ORGANISM: Artificial Sequence
<220> FEATURE:
<223> OTHER INFORMATION: MBP81-99 /DR15 TCR Ob-3D1 beta chain CDR

<400> SEQUENCE: 77

Ser Gly His Ala Thr
1               5

<210> SEQ ID NO 78
<211> LENGTH: 6
<212> TYPE: PRT
<213> ORGANISM: Artificial Sequence
<220> FEATURE:
<223> OTHER INFORMATION: MBP81-99 /DR15 TCR Ob-3D1 beta chain CDR

<400> SEQUENCE: 78

Phe Gln Asn Asn Gly Val
1               5

<210> SEQ ID NO 79
<211> LENGTH: 13
<212> TYPE: PRT
<213> ORGANISM: Artificial Sequence
<220> FEATURE:
<223> OTHER INFORMATION: MBP81-99 /DR15 TCR Ob-3D1 beta chain CDR

<400> SEQUENCE: 79

Ala Ser Ser Ile Arg His Arg Thr Asn Thr Glu Ala Phe
1               5                   10

<210> SEQ ID NO 80
<211> LENGTH: 111
<212> TYPE: PRT
<213> ORGANISM: Artificial Sequence
<220> FEATURE:
<223> OTHER INFORMATION: MBP81-99 /DR15 TCR Ob-3D1 alpha variable

<400> SEQUENCE: 80

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
                20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Leu Ile Thr Ala Ser Arg
65                  70                  75                  80

Ala Ala Asp Thr Ala Ser Tyr Phe Cys Ala Thr Asp Gly Asn Gly Asn
                85                  90                  95

Gln Phe Tyr Phe Gly Thr Gly Thr Ser Leu Thr Val Ile Pro Asn
            100                 105                 110

<210> SEQ ID NO 81
<211> LENGTH: 115
<212> TYPE: PRT

-continued

```
<213> ORGANISM: Artificial Sequence
<220> FEATURE:
<223> OTHER INFORMATION: MBP81-99 /DR15 TCR Ob-3D1 beta variable

<400> SEQUENCE: 81

Glu Ala Gly Val Ala Gln Ser Pro Arg Tyr Lys Ile Ile Glu Lys Arg
1               5                   10                  15

Gln Ser Val Ala Phe Trp Cys Asn Pro Ile Ser Gly His Ala Thr Leu
            20                  25                  30

Tyr Trp Tyr Gln Gln Ile Leu Gly Gln Gly Pro Lys Leu Leu Ile Gln
        35                  40                  45

Phe Gln Asn Asn Gly Val Val Asp Asp Ser Gln Leu Pro Lys Asp Arg
    50                  55                  60

Phe Ser Ala Glu Arg Leu Lys Gly Val Asp Ser Thr Leu Lys Ile Gln
65                  70                  75                  80

Pro Ala Lys Leu Glu Asp Ser Ala Val Tyr Leu Cys Ala Ser Ser Ile
                85                  90                  95

Arg His Arg Thr Asn Thr Glu Ala Phe Phe Gly Gln Gly Thr Arg Leu
            100                 105                 110

Thr Val Val
        115

<210> SEQ ID NO 82
<211> LENGTH: 6
<212> TYPE: PRT
<213> ORGANISM: Artificial Sequence
<220> FEATURE:
<223> OTHER INFORMATION: MBP81-99 /DR15 TCR Hy-1A8 alpha chain CDR

<400> SEQUENCE: 82

Asp Ser Ala Ser Asn Tyr
1               5

<210> SEQ ID NO 83
<211> LENGTH: 7
<212> TYPE: PRT
<213> ORGANISM: Artificial Sequence
<220> FEATURE:
<223> OTHER INFORMATION: MBP81-99 /DR15 TCR Hy-1A8 alpha chain CDR

<400> SEQUENCE: 83

Ile Arg Ser Asn Val Gly Glu
1               5

<210> SEQ ID NO 84
<211> LENGTH: 11
<212> TYPE: PRT
<213> ORGANISM: Artificial Sequence
<220> FEATURE:
<223> OTHER INFORMATION: MBP81-99 /DR15 TCR Hy-1A8 alpha chain CDR

<400> SEQUENCE: 84

Ala Ala Ser Ser Phe Gly Asn Glu Lys Leu Thr
1               5                   10

<210> SEQ ID NO 85
<211> LENGTH: 5
<212> TYPE: PRT
<213> ORGANISM: Artificial Sequence
<220> FEATURE:
<223> OTHER INFORMATION: MBP81-99 /DR15 TCR Hy-1A8 beta chain CDR

<400> SEQUENCE: 85
```

```
Ser Gly His Thr Ala
1               5

<210> SEQ ID NO 86
<211> LENGTH: 6
<212> TYPE: PRT
<213> ORGANISM: Artificial Sequence
<220> FEATURE:
<223> OTHER INFORMATION: MBP81-99 /DR15 TCR Hy-1A8 beta chain CDR

<400> SEQUENCE: 86

Phe Gln Gly Thr Gly Ala
1               5

<210> SEQ ID NO 87
<211> LENGTH: 10
<212> TYPE: PRT
<213> ORGANISM: Artificial Sequence
<220> FEATURE:
<223> OTHER INFORMATION: MBP81-99 /DR15 TCR Hy-1A8 beta chain CDR

<400> SEQUENCE: 87

Ala Thr Ser Ala Leu Gly Asp Thr Gln Tyr
1               5                   10

<210> SEQ ID NO 88
<211> LENGTH: 113
<212> TYPE: PRT
<213> ORGANISM: Artificial Sequence
<220> FEATURE:
<223> OTHER INFORMATION: MBP81-99 /DR15 TCR Hy-1A8 alpha variable

<400> SEQUENCE: 88

Gly Glu Asn Val Glu Gln His Pro Ser Thr Leu Ser Val Gln Glu Gly
1               5                   10                  15

Asp Ser Ala Val Ile Lys Cys Thr Tyr Ser Asp Ser Ala Ser Asn Tyr
            20                  25                  30

Phe Pro Trp Tyr Lys Gln Glu Leu Gly Lys Gly Pro Gln Leu Ile Ile
        35                  40                  45

Asp Ile Arg Ser Asn Val Gly Glu Lys Lys Asp Gln Arg Ile Ala Val
    50                  55                  60

Thr Leu Asn Lys Thr Ala Lys His Phe Ser Leu His Ile Thr Glu Thr
65                  70                  75                  80

Gln Pro Glu Asp Ser Ala Val Tyr Phe Cys Ala Ala Ser Ser Phe Gly
                85                  90                  95

Asn Glu Lys Leu Thr Phe Gly Thr Gly Thr Arg Leu Thr Ile Ile Pro
            100                 105                 110

Asn

<210> SEQ ID NO 89
<211> LENGTH: 112
<212> TYPE: PRT
<213> ORGANISM: Artificial Sequence
<220> FEATURE:
<223> OTHER INFORMATION: MBP81-99 /DR15 TCR Hy-1A8 beta variable

<400> SEQUENCE: 89

Gly Ala Gly Val Ser Gln Thr Pro Ser Asn Lys Val Thr Glu Lys Gly
1               5                   10                  15

Lys Tyr Val Glu Leu Arg Cys Asp Pro Ile Ser Gly His Thr Ala Leu
            20                  25                  30

Tyr Trp Tyr Arg Gln Ser Leu Gly Gln Gly Pro Glu Phe Leu Ile Tyr
```

```
           35                  40                  45

Phe Gln Gly Thr Gly Ala Ala Asp Asp Ser Gly Leu Pro Asn Asp Arg
    50                  55                  60

Phe Phe Ala Val Arg Pro Glu Gly Ser Val Ser Thr Leu Lys Ile Gln
65                  70                  75                  80

Arg Thr Glu Arg Gly Asp Ser Ala Val Tyr Leu Cys Ala Thr Ser Ala
                85                  90                  95

Leu Gly Asp Thr Gln Tyr Phe Gly Pro Gly Thr Arg Leu Thr Val Leu
                100                 105                 110

<210> SEQ ID NO 90
<211> LENGTH: 5
<212> TYPE: PRT
<213> ORGANISM: Artificial Sequence
<220> FEATURE:
<223> OTHER INFORMATION: MBP81-99 /DR15 TCR Hy-2E11 alpha chain CDR

<400> SEQUENCE: 90

Thr Ser Ile Asn Asn
1               5

<210> SEQ ID NO 91
<211> LENGTH: 7
<212> TYPE: PRT
<213> ORGANISM: Artificial Sequence
<220> FEATURE:
<223> OTHER INFORMATION: MBP81-99 /DR15 TCR Hy-2E11 alpha chain CDR

<400> SEQUENCE: 91

Ile Arg Ser Asn Glu Arg Glu
1               5

<210> SEQ ID NO 92
<211> LENGTH: 11
<212> TYPE: PRT
<213> ORGANISM: Artificial Sequence
<220> FEATURE:
<223> OTHER INFORMATION: MBP81-99 /DR15 TCR Hy-2E11 alpha chain CDR

<400> SEQUENCE: 92

Ala Thr Asp Ser Gly Gly Ser Tyr Ile Pro Thr
1               5                   10

<210> SEQ ID NO 93
<211> LENGTH: 5
<212> TYPE: PRT
<213> ORGANISM: Artificial Sequence
<220> FEATURE:
<223> OTHER INFORMATION: MBP81-99 /DR15 TCR Hy-2E11 beta chain CDR

<400> SEQUENCE: 93

Ser Gln Val Thr Met
1               5

<210> SEQ ID NO 94
<211> LENGTH: 7
<212> TYPE: PRT
<213> ORGANISM: Artificial Sequence
<220> FEATURE:
<223> OTHER INFORMATION: MBP81-99 /DR15 TCR Hy-2E11 beta chain CDR

<400> SEQUENCE: 94

Ala Asn Gln Gly Ser Glu Ala
1               5
```

```
<210> SEQ ID NO 95
<211> LENGTH: 13
<212> TYPE: PRT
<213> ORGANISM: Artificial Sequence
<220> FEATURE:
<223> OTHER INFORMATION: MBP81-99 /DR15 TCR Hy-2E11 beta chain CDR

<400> SEQUENCE: 95

Ser Ala Trp Pro Ser Gly Gln Gly Thr Tyr Gly Tyr Thr
1               5                   10

<210> SEQ ID NO 96
<211> LENGTH: 112
<212> TYPE: PRT
<213> ORGANISM: Artificial Sequence
<220> FEATURE:
<223> OTHER INFORMATION: MBP81-99 /DR15 TCR Hy-2E11 alpha variable

<400> SEQUENCE: 96

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
                20                  25                  30

Gln Trp Tyr Arg Gln Asn Ser Gly Arg Gly Leu Val His Leu Ile Leu
            35                  40                  45

Ile Arg Ser Asn Glu Arg Glu Lys His Ser Gly Arg Leu Arg Val Thr
        50                  55                  60

Leu Asp Thr Ser Lys Lys Ser Ser Ser Leu Leu Ile Thr Ala Ser Arg
65                  70                  75                  80

Ala Ala Asp Thr Ala Ser Tyr Phe Cys Ala Thr Asp Ser Gly Gly Ser
                85                  90                  95

Tyr Ile Pro Thr Phe Gly Arg Gly Thr Ser Leu Ile Val His Pro Tyr
            100                 105                 110

<210> SEQ ID NO 97
<211> LENGTH: 116
<212> TYPE: PRT
<213> ORGANISM: Artificial Sequence
<220> FEATURE:
<223> OTHER INFORMATION: MBP81-99 /DR15 TCR Hy-2E11 beta variable

<400> SEQUENCE: 97

Ser Ala Val Ile Ser Gln Lys Pro Ser Arg Asp Ile Cys Gln Arg Gly
1               5                   10                  15

Thr Ser Leu Thr Ile Gln Cys Gln Val Asp Ser Gln Val Thr Met Ile
                20                  25                  30

Phe Trp Tyr Arg Gln Gln Pro Gly Gln Ser Leu Thr Leu Ile Ala Thr
            35                  40                  45

Ala Asn Gln Gly Ser Glu Ala Thr Tyr Glu Ser Gly Phe Val Ile Asp
        50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys Ser Ala Trp
                85                  90                  95

Pro Ser Gly Gln Gly Thr Tyr Gly Tyr Thr Phe Gly Ser Gly Thr Arg
            100                 105                 110

Leu Thr Val Val
        115
```

1

ENGINEERED REGULATORY T CELL

FIELD OF THE INVENTION

The present invention relates to an engineered regulatory T cell (Treg). In particular, the present invention relates to a Treg comprising a T cell receptor (TCR) which is capable of specifically binding to myelin basic protein (MBP). The present invention further relates to methods for providing an engineered Treg and to methods and uses of said engineered Treg.

BACKGROUND TO THE INVENTION

Many autoimmune and inflammatory central nervous system (CNS) diseases involve autoreactive T-cells. For example, Multiple Sclerosis (MS), which is an autoimmune inflammatory demyelinating condition of the central nervous system and is the most common neurological disorder among young adults.

Current treatments for autoimmune and inflammatory CNS diseases generally suppress the immune system. For example, one treatment includes transplantation of bone marrow along with administration of cytostatics and immunosuppressive drugs. Autologous haematopoietic stem cell transplantation can have lasting beneficial effects for some patients, but the procedure requires aggressive myelo-ablative conditioning which is associated with substantial toxicity and risk.

Although several disease-modifying treatments (DMTs) have been approved to reduce the frequency of clinical relapses, most patients continue to clinically deteriorate under current therapy schedules. Neither DMTs nor stem cell transplantation can mediate CNS-specific suppression of the immunopathology of autoimmune and inflammatory CNS diseases.

Currently, effective treatments for autoimmune and inflammatory CNS diseases do not exist. Treatment is focused on merely reducing its symptoms, usually by general suppression of the immune system. There is a need for a therapy which specifically targets local immune responses associated with onset and progression of CNS disease.

SUMMARY OF ASPECTS OF THE INVENTION

The present invention is based, at least in part, on the inventors' determination that T cell receptor gene transfer technology can be used to generate antigen-specific Tregs. It has been shown that human antigen-specific Tregs can suppress activated T cells.

In particular, the present inventors have produced MBP-specific Tregs for example, by retroviral transfer of MBP-TCR genes into purified Tregs and/or by retroviral transfer of MBP-TCR and forkhead box P3 (FOXP3) genes into conventional CD4⁺ T cells. Without wishing to be bound by theory, these engineered Tregs with TCRs specific for MBP may be used in the suppression of diseases e.g. autoimmune diseases, where local activation of MBP-specific Tregs in the central nervous system (CNS) may suppress CNS pathology as seen in MS and other CNS inflammatory conditions.

Further, a large number of TCRs cannot be successfully expressed as an exogenous TCR. It cannot be predicted which TCRs can be effectively expressed as an exogenous TCR, in particular in a Treg.

The present invention particularly relates to an engineered regulatory T cell (Treg) comprising a T cell receptor with advantageous properties, for example in respect of effector cytokine expression.

Accordingly, the present invention provides an engineered Treg comprising a T cell receptor,
  wherein the TCR comprises an α chain and a β chain,
  wherein the α chain and the β chain each comprises three complementarity determining regions (CDRs) and the sequence of each CDR3 is as follows:

```
CDR3α
                              (SEQ ID NO: 1)
ATDTTSGTYKYI

CDR3β
                              (SEQ ID NO: 2)
SARDLTSGANNEQF
``` or a variant of those sequences having up to three amino acid changes.

The TCR may be capable of specifically binding to a peptide which comprises at least 90% identity to MBP 82-102 (SEQ ID NO: 12) or a fragment thereof when the peptide is presented by a major histocompatibility complex (MHC) molecule.

The MBP82-102 peptide binds to HLA-DR15 (DRB1*1501).

The α chain of the TCR may comprise three CDRs having the following amino acid sequences:

```
CDR1α
                              (SEQ ID NO: 3)
TSINN

CDR2α
                              (SEQ ID NO: 4)
IRSNERE

CDR3α
                              (SEQ ID NO: 1)
ATDTTSGTYKYI
``` or variants of those sequences having up to three amino acid changes;
and the β chain of the TCR may comprise three CDRs having the following amino acid sequences:

```
CDR1β
                              (SEQ ID NO: 5)
DFQATT

CDR2β
                              (SEQ ID NO: 6)
SNEGSKA

CDR3β
                              (SEQ ID NO: 2)
SARDLTSGANNEQF
``` or variants of those sequences having up to three amino acid changes.

The variable region of the α chain of the TCR may comprise an amino acid sequence having at least 80% sequence identity to SEQ ID NO: 7, wherein the sequence identity does not include the CDR sequences; and
  the variable region of the β chain of the TCR may comprise an amino acid sequence having at least 80% sequence identity to SEQ ID NO: 8, wherein the sequence identity does not include the CDR sequences.

The variable region of the α chain of the TCR may comprise an amino acid sequence having at least 80% sequence identity to SEQ ID NO: 7; and the variable region of the β chain of the TCR may comprise an amino acid sequence having at least 80% sequence identity to SEQ ID NO: 8.

The constant region domains of the α chain and β chain of the TCR may each comprise an additional cysteine residue, enabling the formation of an extra disulphide bond between the α chain and the β chain. Suitably, the additional disulphide bond reduces mispairing with endogenous TCR chains.

The α chain of the TCR may comprise an amino acid sequence having at least 80% sequence identity to SEQ ID NO: 9; and the β chain of the TCR may comprise an amino acid sequence having at least 80% sequence identity to SEQ ID NO: 10.

In one aspect, the Treg is derived from a T cell isolated from a subject.

In another aspect, the present invention provides a pharmaceutical composition comprising an engineered Treg according to the invention.

In one aspect, the present invention relates to an engineered Treg or pharmaceutical composition according to the invention for use in treating a disease.

In another aspect, the present invention relates to the use of an engineered Treg or pharmaceutical composition according to the invention in the manufacture of a medicament.

In one aspect, there is provided a method for treating or preventing a disease in a subject in need of same which comprises the step of administering an engineered Treg or pharmaceutical composition according to the invention to the subject.

In another aspect, there is provided an engineered Treg or pharmaceutical composition for use, or a use or a method according to the invention, wherein the disease is multiple sclerosis.

In one aspect, there is provided an engineered Treg or pharmaceutical composition for use, or a use or a method according to the invention, wherein the subject is a DRB1*1501 positive subject.

In another aspect, there is provided a vector which comprises a nucleic acid sequence which encodes a TCR as defined herein and a nucleic acid sequence which encodes FOXP3.

In one aspect, a kit of polynucleotides or a kit of vectors is provided which comprises a first polynucleotide or vector which comprises a nucleic acid sequence which encodes a TCR as defined herein and a second polynucleotide or vector which comprises a nucleic acid sequence which encodes FOXP3. Suitably, the first and second polynucleotides or vectors are separate.

In one aspect, there is provided a method for producing an engineered Treg according to the invention which comprises the step of introducing into a cell in vitro or ex vivo a polynucleotide encoding a TCR as defined herein.

Suitably the T cell is a natural Treg which expresses FOXP3.

In one aspect, the method further comprises the step of introducing into the cell in vitro or ex vivo a polynucleotide encoding a FOXP3 protein.

Suitably the cell is a T cell.

Suitably the T cell is a 'conventional' T cell.

Suitably, the cell is a human cell, such as a human T cell.

Suitably, the cell is a human Treg cell.

In one aspect of a method of the invention, the step of introducing the polynucleotide encoding a TCR and the polynucleotide encoding FOXP3 are performed sequentially, separately or simultaneously.

In another aspect of a method of the invention, the polynucleotide encoding a TCR and the polynucleotide encoding FOXP3 are introduced to the cell using the vector of the invention.

Thy1.1+CD4+CD25+ Treg were isolated from lymph nodes and splenocytes of HLA-DRB*0401 transgenic mice by bead sort. Treg were transduced with a reference TCR, reference TCR+murine FOXP3 or cultured with virus-free supernatant (mock). 1 day after transduction TCR or TCR+ FOXP3 transduced cells were injected into HLA-DRB*0401 transgenic hosts conditioned with 4 Gy irradiation. 7 weeks later flow cytometry was used to determine the engraftment of transduced Treg A. Transduction efficiency was determined through expression of human variable 2.1 and murine Foxp3 on dl post-transduction B. Splenocytes from mice that received Treg transduced with TCR or TCR+FOXP3 were stained with Thy1.1 to identify transferred cells (top panel) and FOXP3 and TCR (bottom panel) C. Cumulative data showing fold change in transduction efficiency (left panel) and fold change in absolute number of transduced cells (right panel) relative to day of injection for Treg transduced with TCR or TCR+FOXP3 (n=3). Error bars show standard error of the mean. Statistical analysis by unpaired t test D. Representative expression of FOXP3 within transduced cells 7 weeks after transfer. Graphs show cumulative of percentage FOXP3+ cells within the transduced population at week 7 (left) and the fold change in FOXP3+ cells relative to the day of injection (n=3). Error bars show standard error of the mean. *p=>0.05, **p=>0.01 determined by unpaired t test.

Figure 6A:
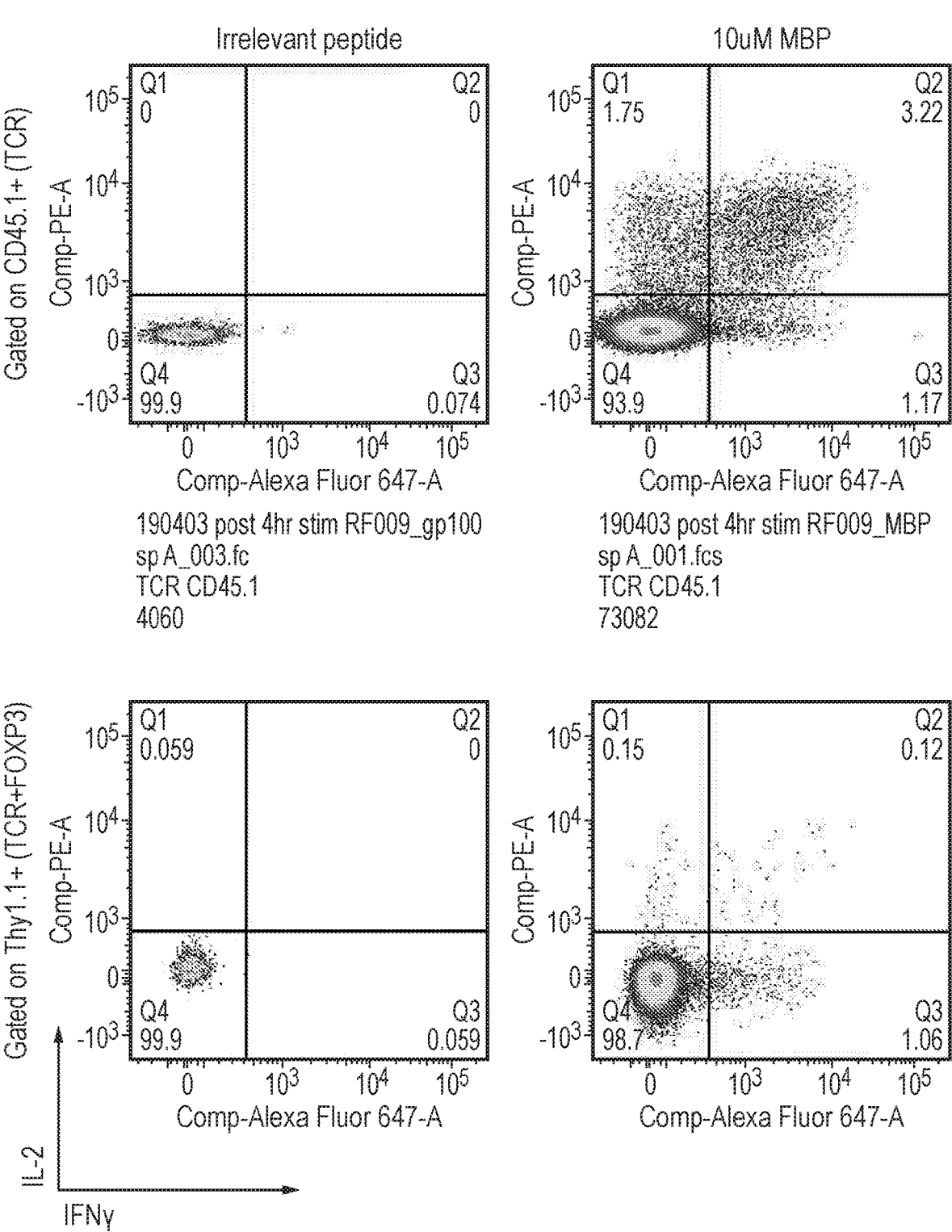
Figure 6B:
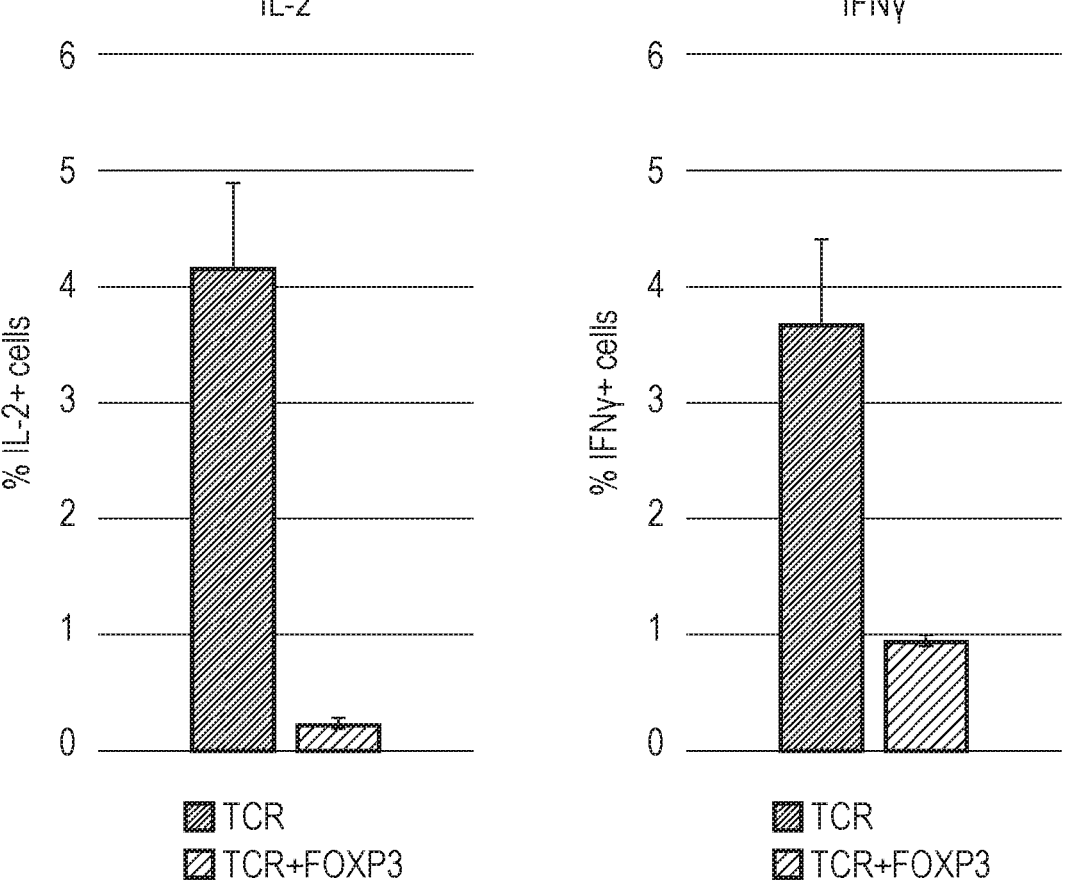

FIG. 6—Treg expressing exogenous FOXP3 retain Treg functionality after 7 weeks in vivo whilst Tregs not expressing exogenous FOXP3 acquire the ability to produce effector cytokines A Splenocytes were cultured for 4 hours with CD86+HLA-DR4+CHO cells pulsed with irrelevant peptide or 10 uM MBP. Production of IL-2 and IFNg was determined by flow cytometry. FACS plots show CD45.1 cells (top panel) containing Treg expressing reference TCR alone and Thy1.1 cells containing Treg expressing reference TCR+FOXP3. B Graphs show cumulative IL-2 and IFNg production by TCR-expressing (dark grey) and TCR+ FOXP3-expressing (light grey) Treg. Error bars show standard deviation of the mean (n=3)

Figure 7:
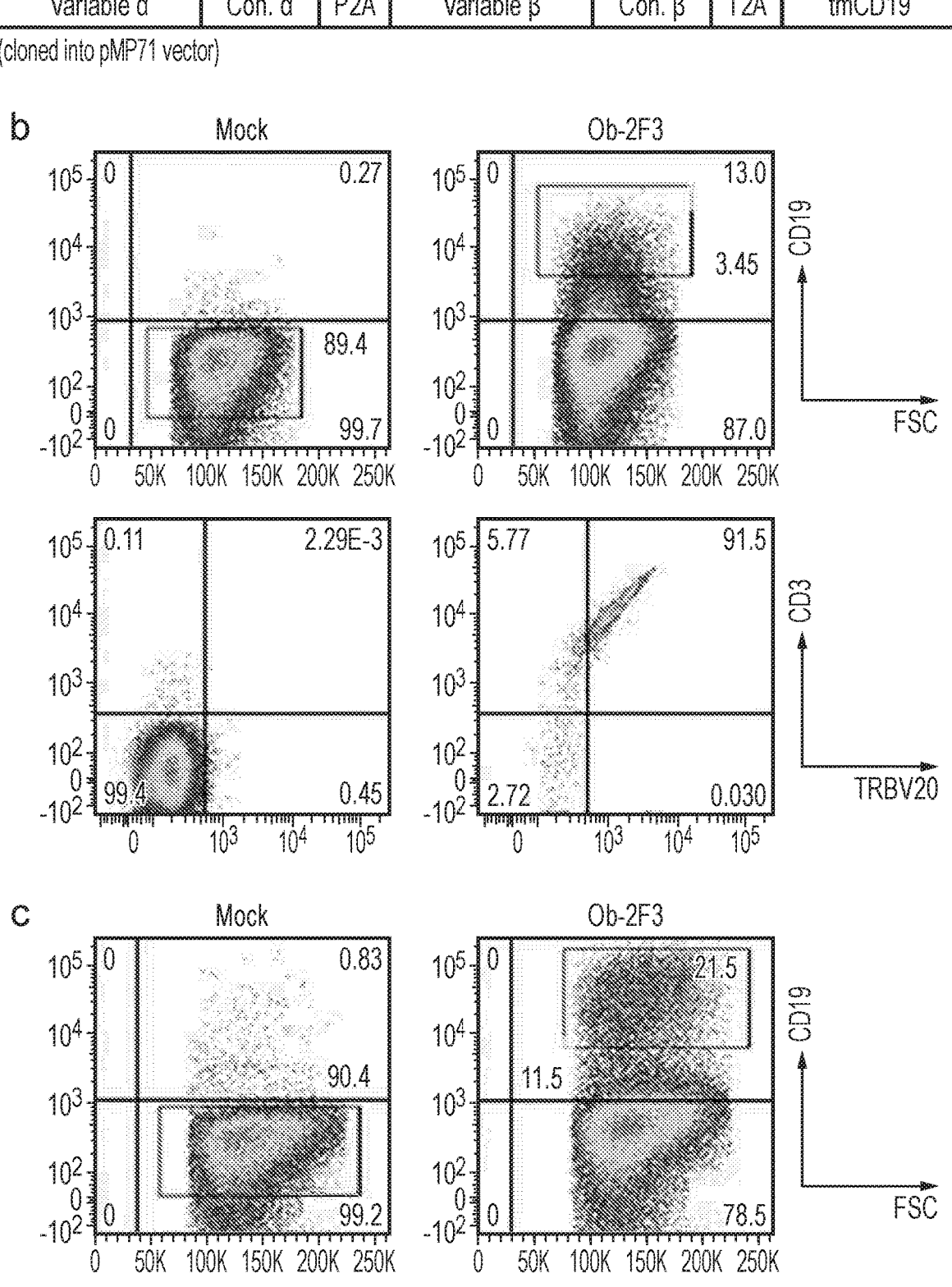
Figure 7:
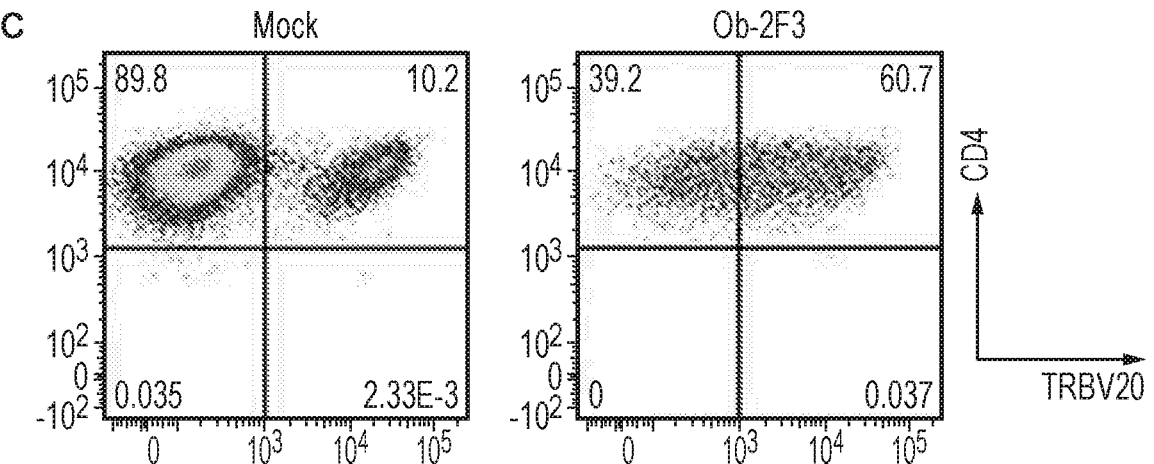
Figure 7:
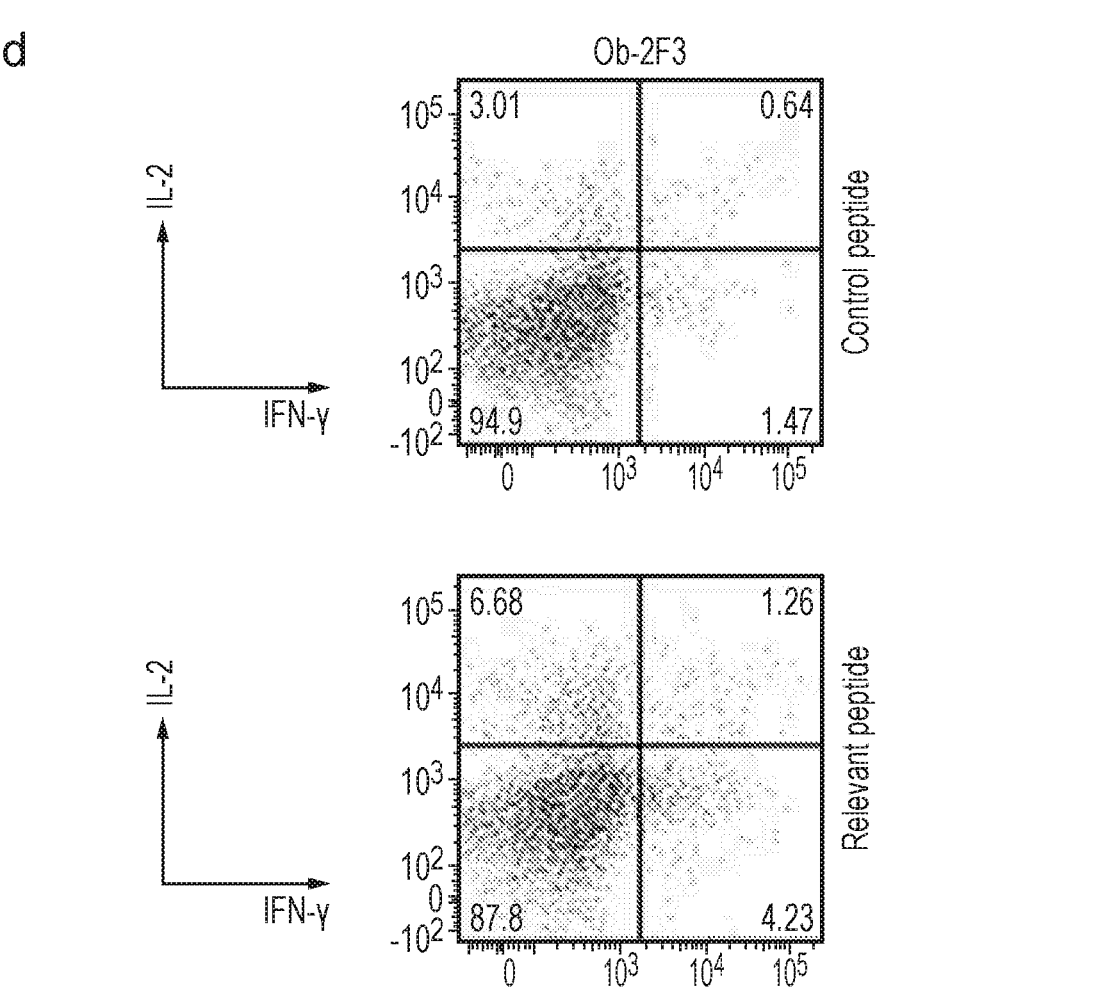
Figure 8:
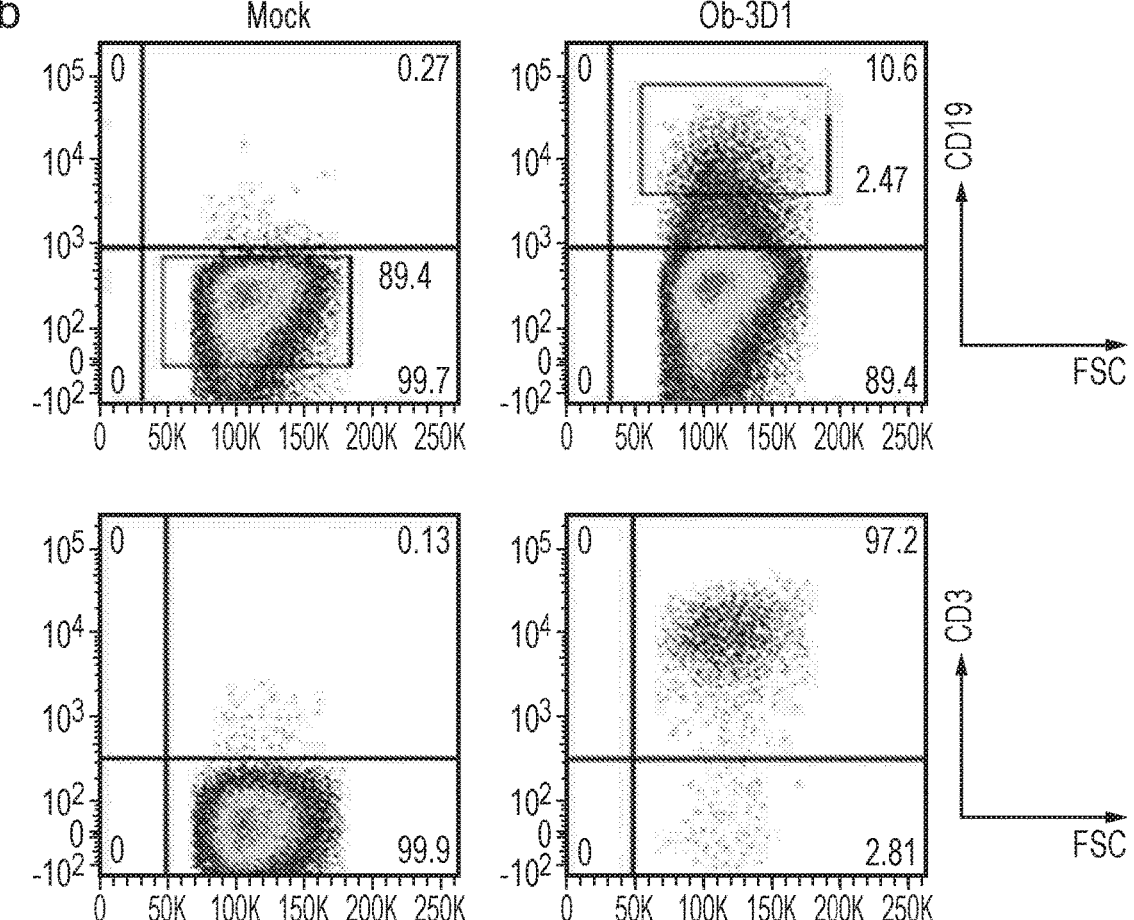
Figure 9:
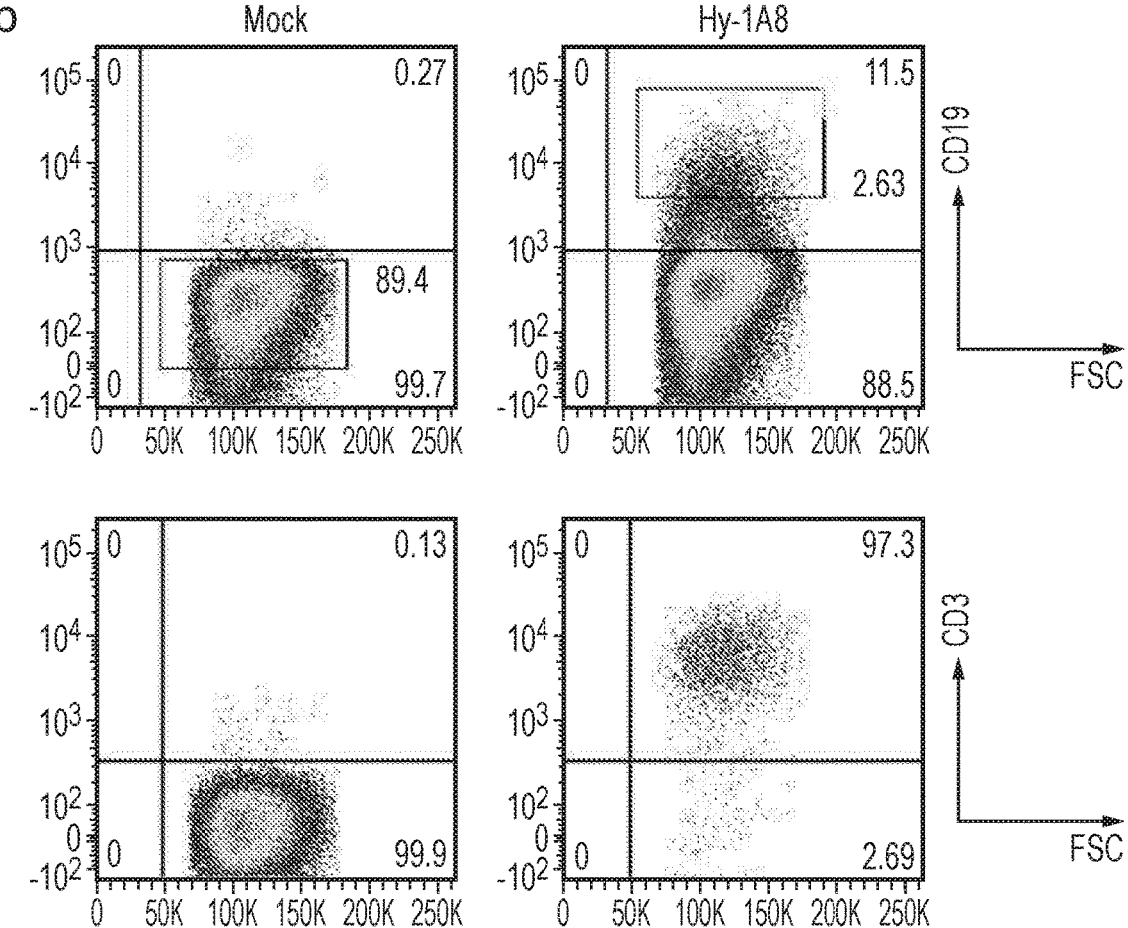
Figure 10:
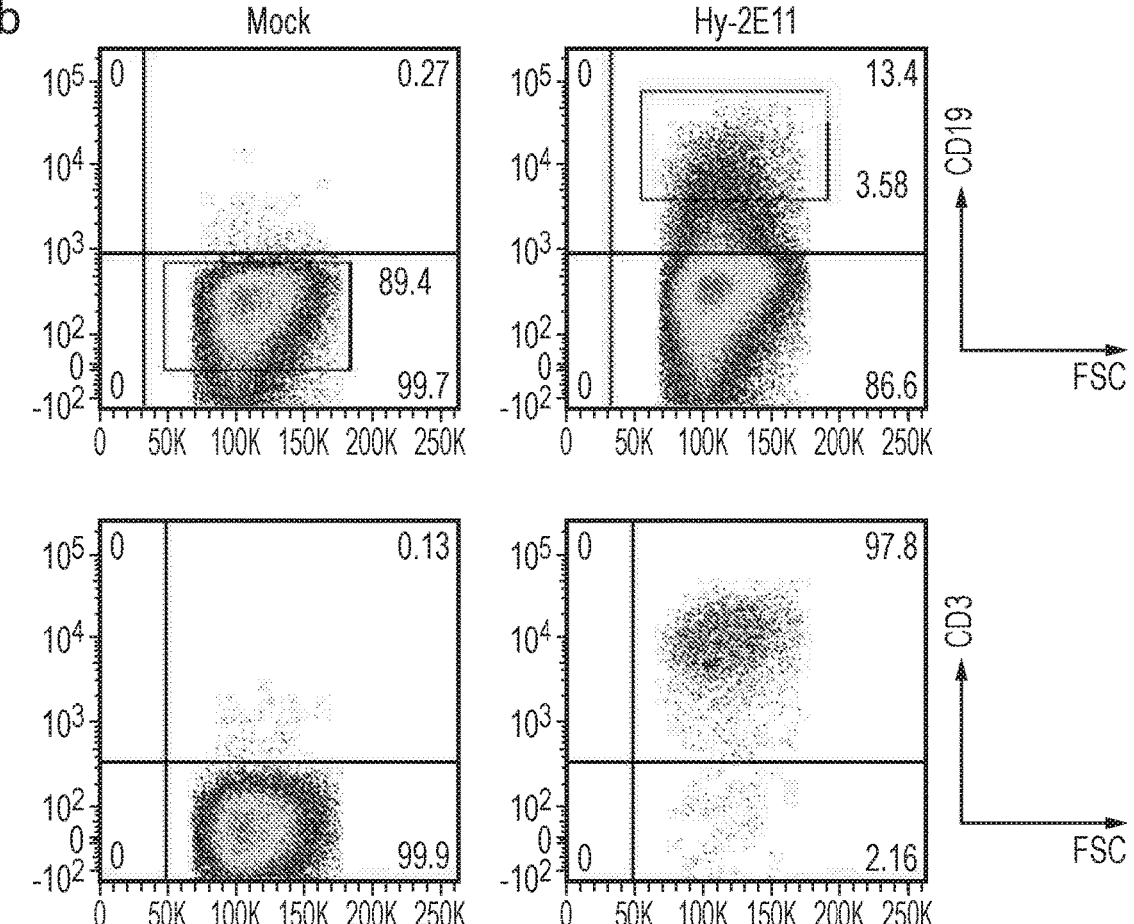
Figure 11:
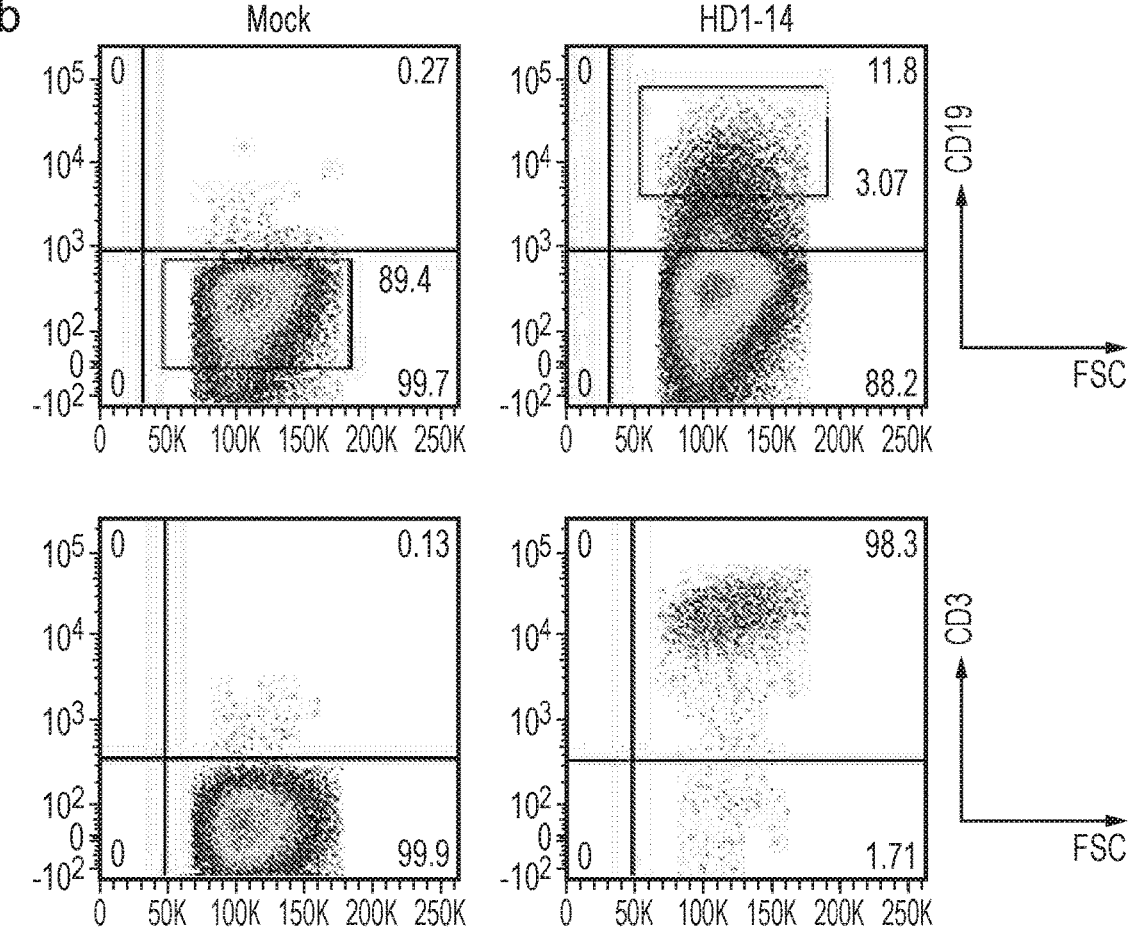
Figure 11:
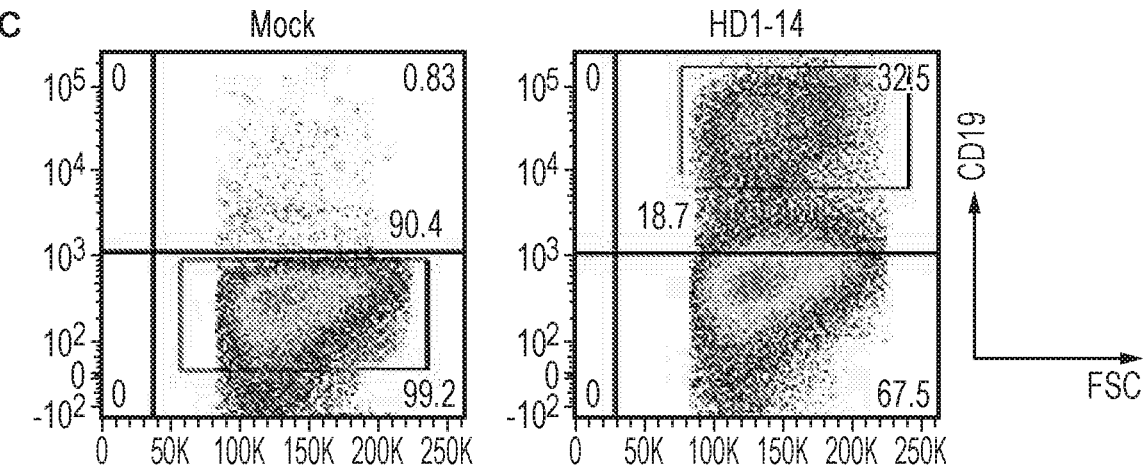
Figure 11:
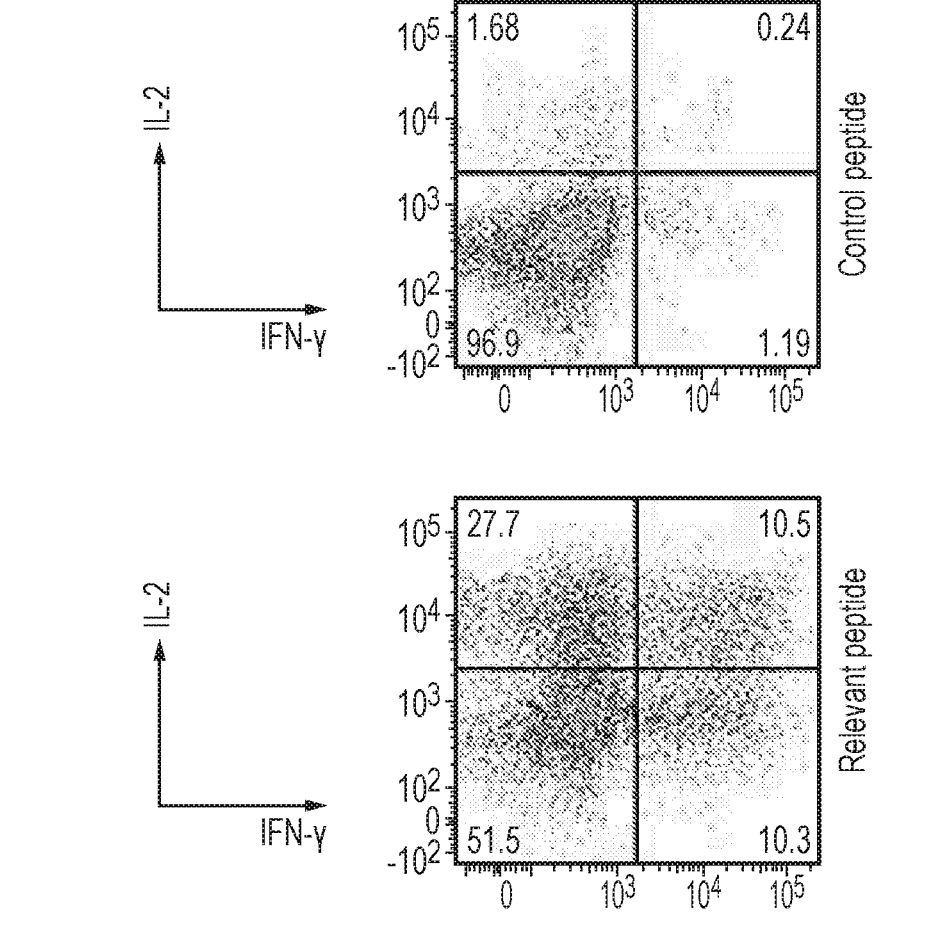
Figure 12:
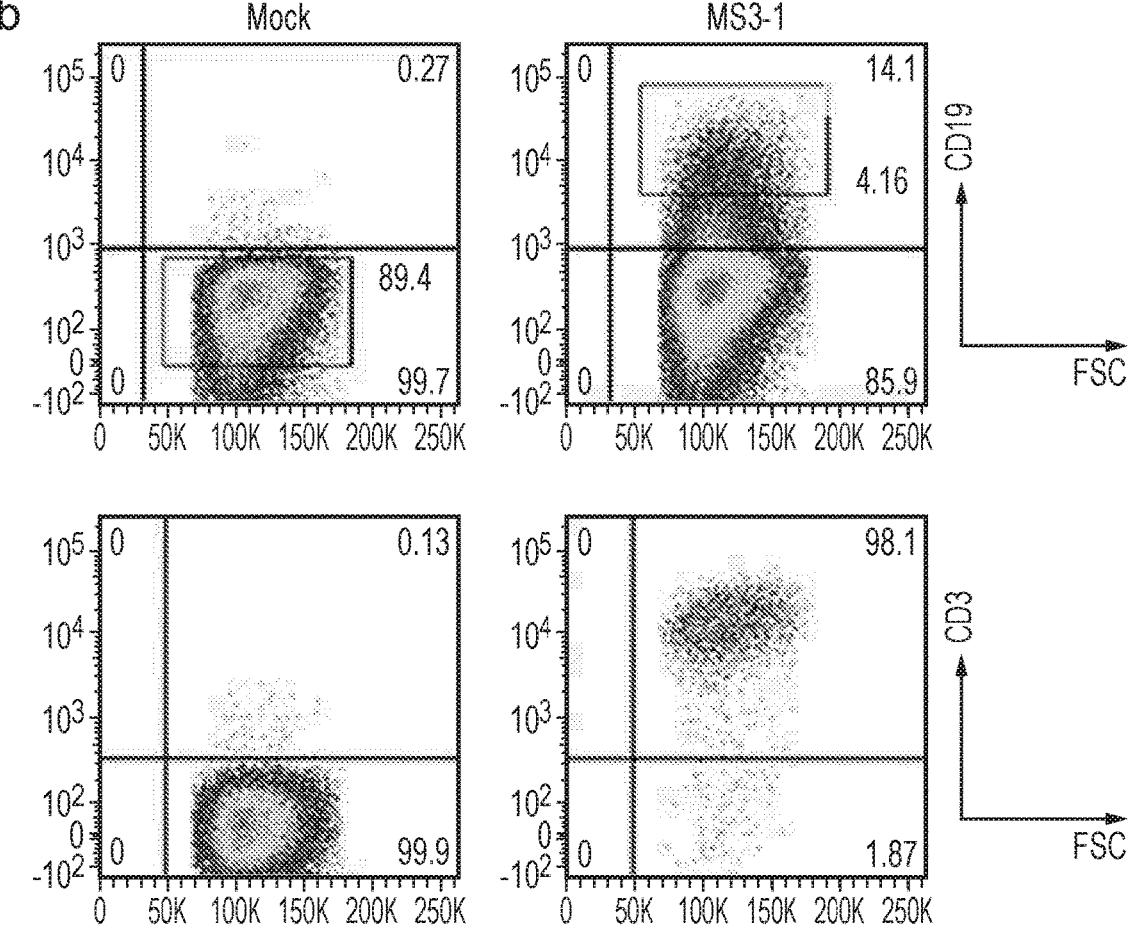
Figure 12:
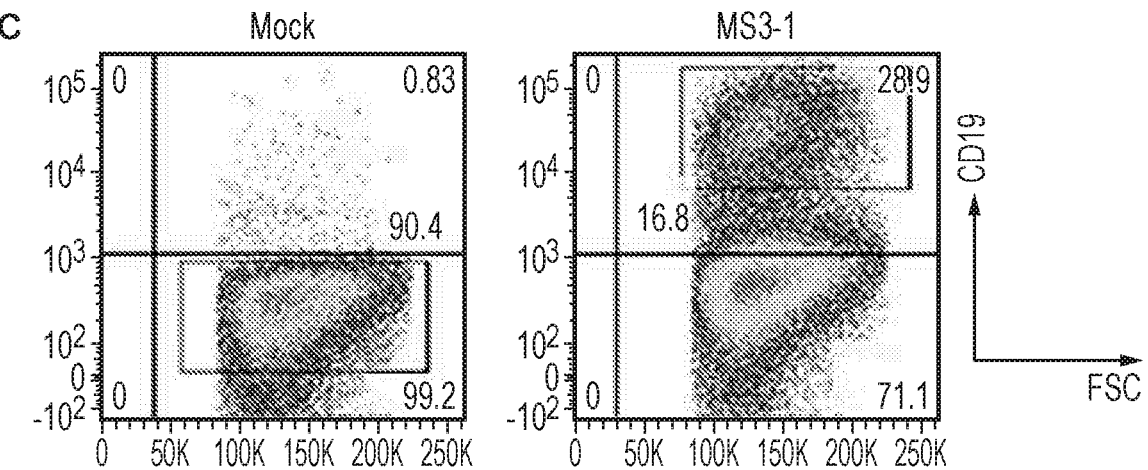
Figure 12:
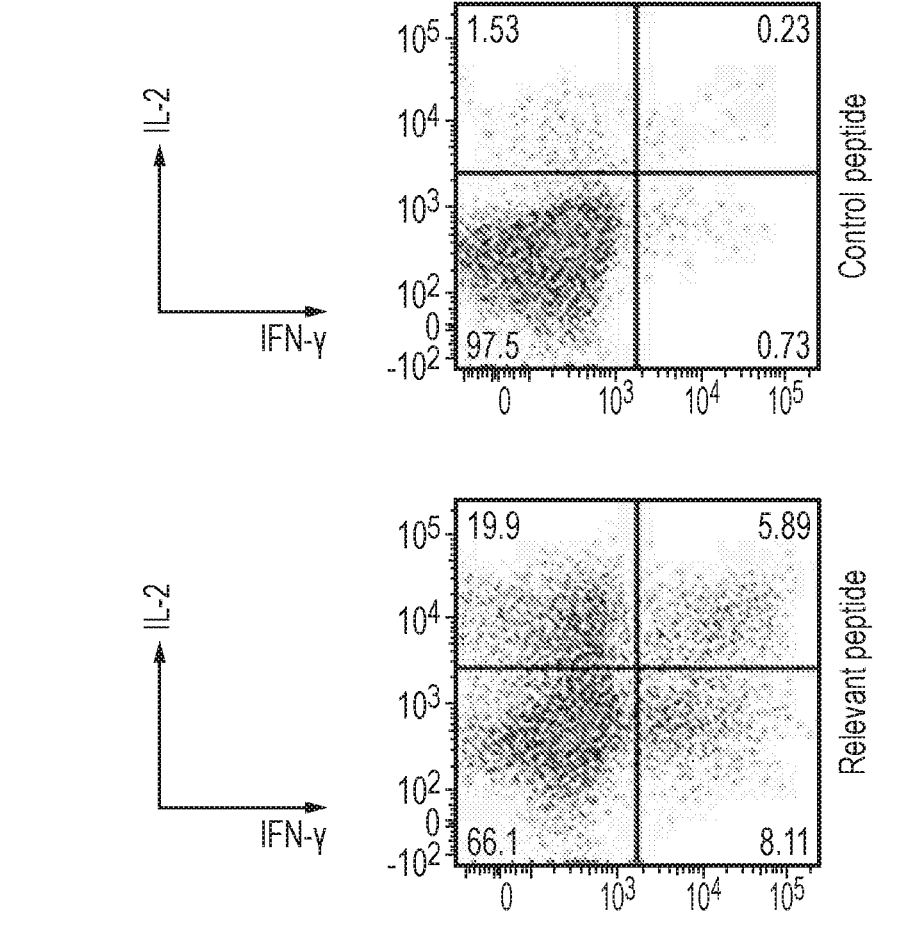
Figure 13:
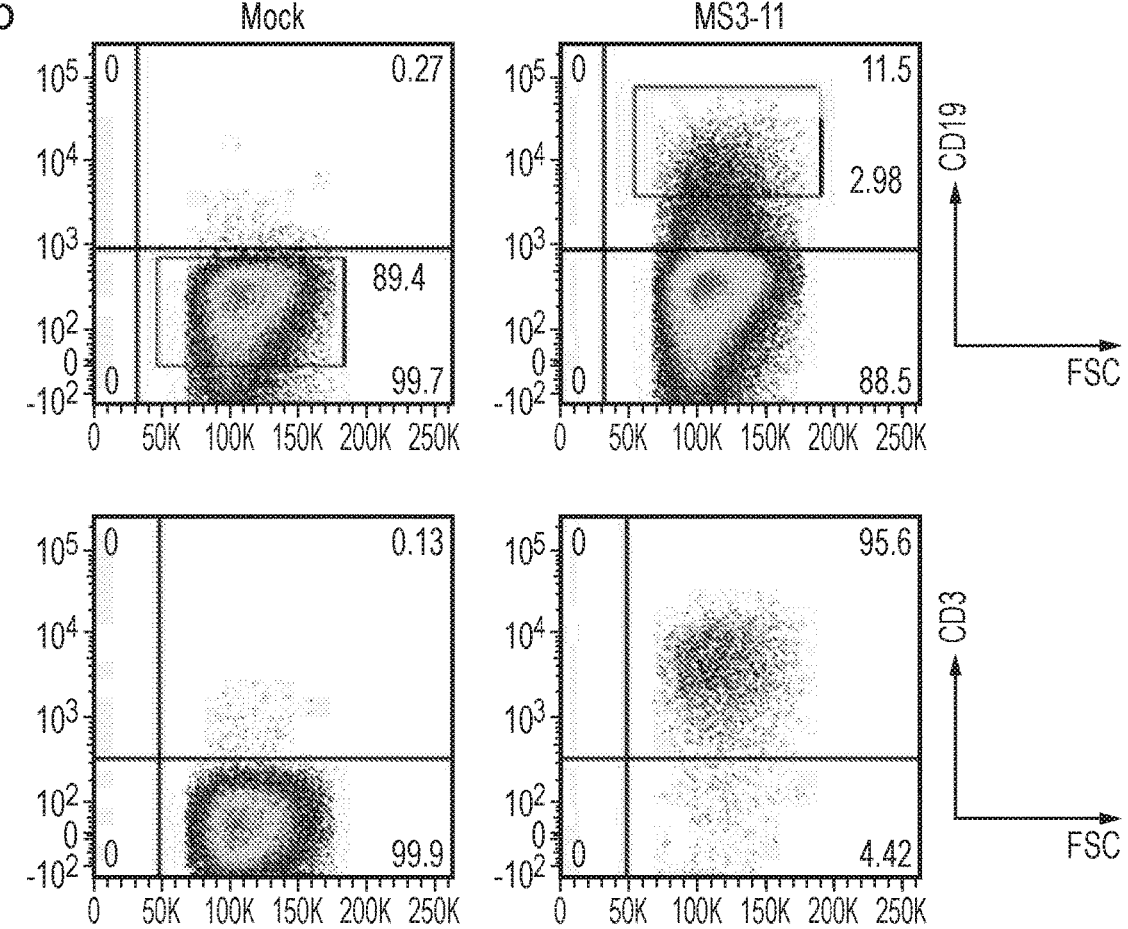
Figure 13:
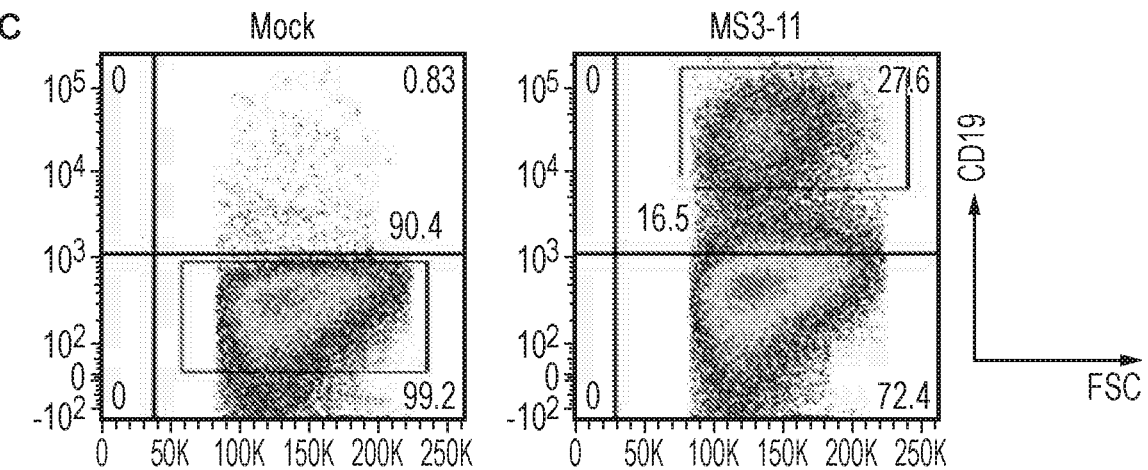
Figure 13:
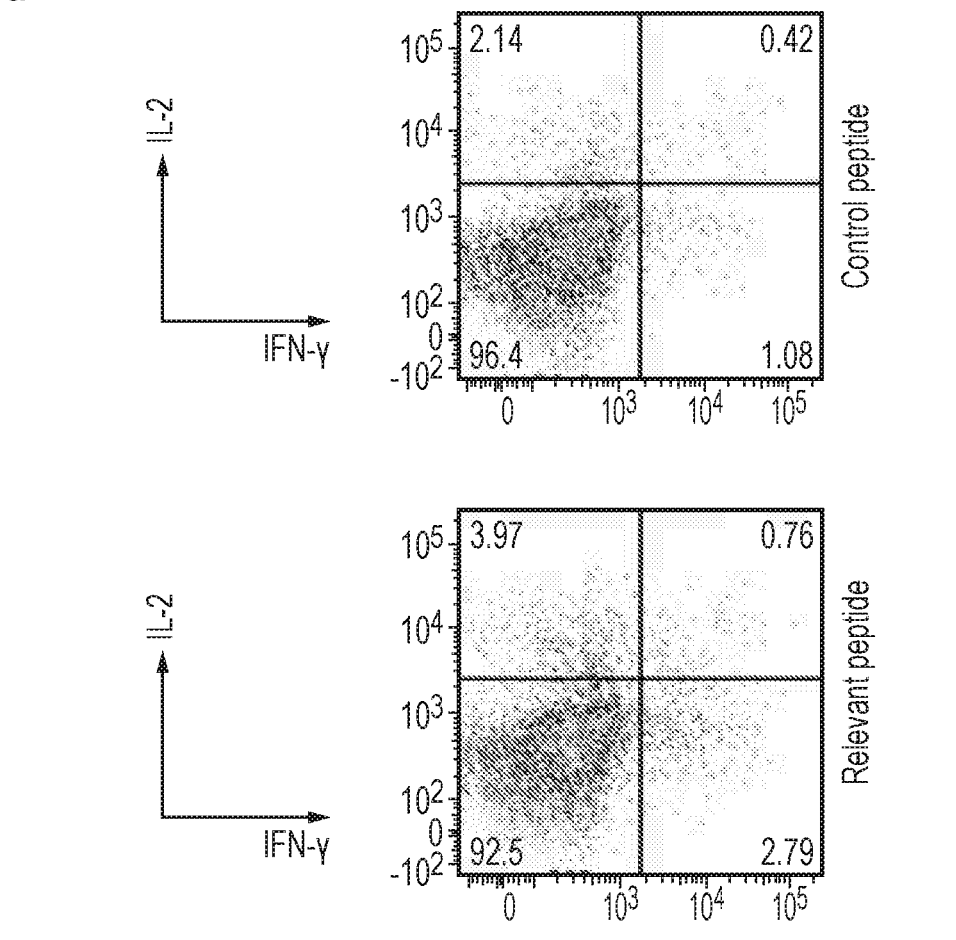
Figure 14:
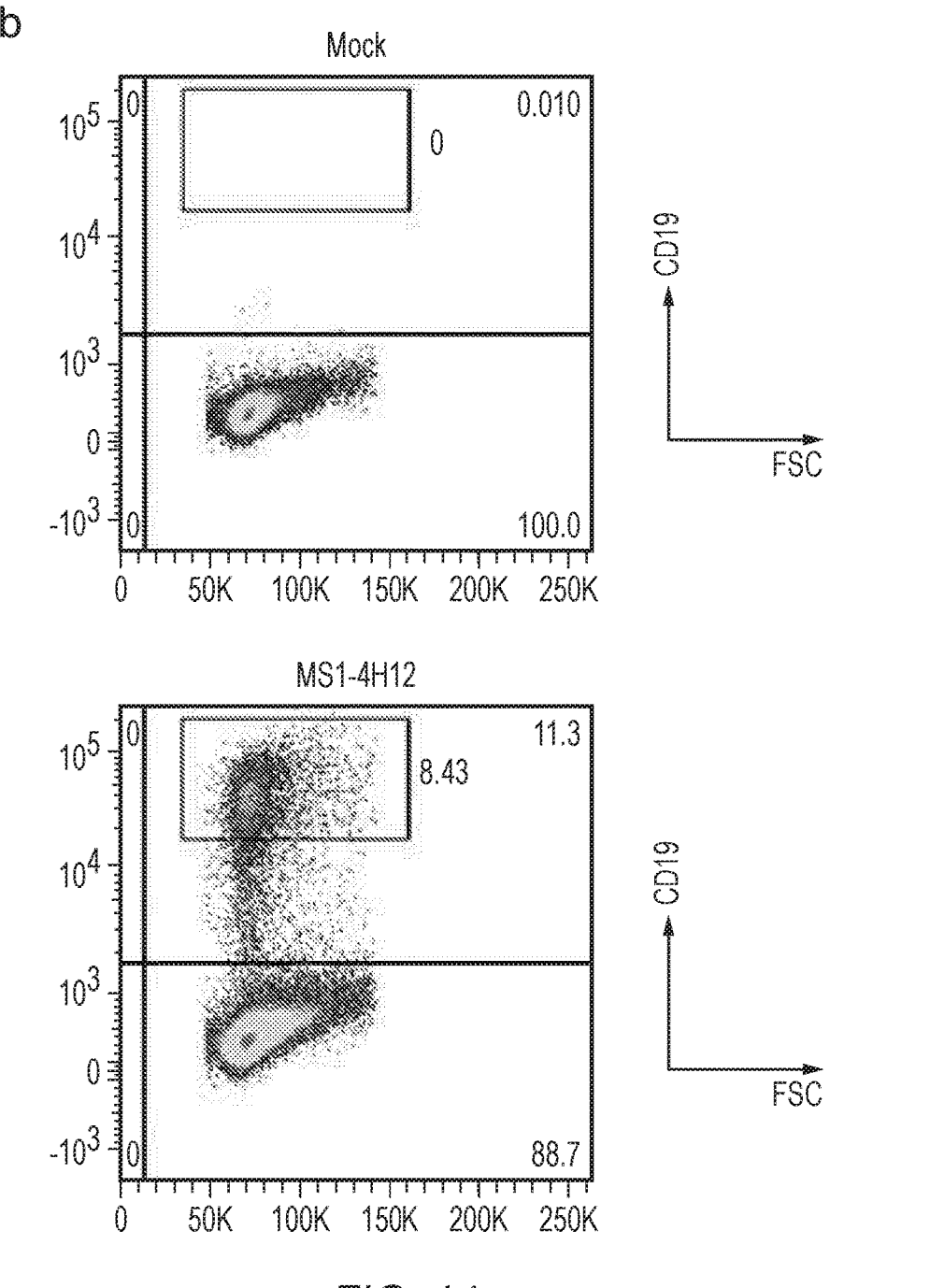
Figure 15:
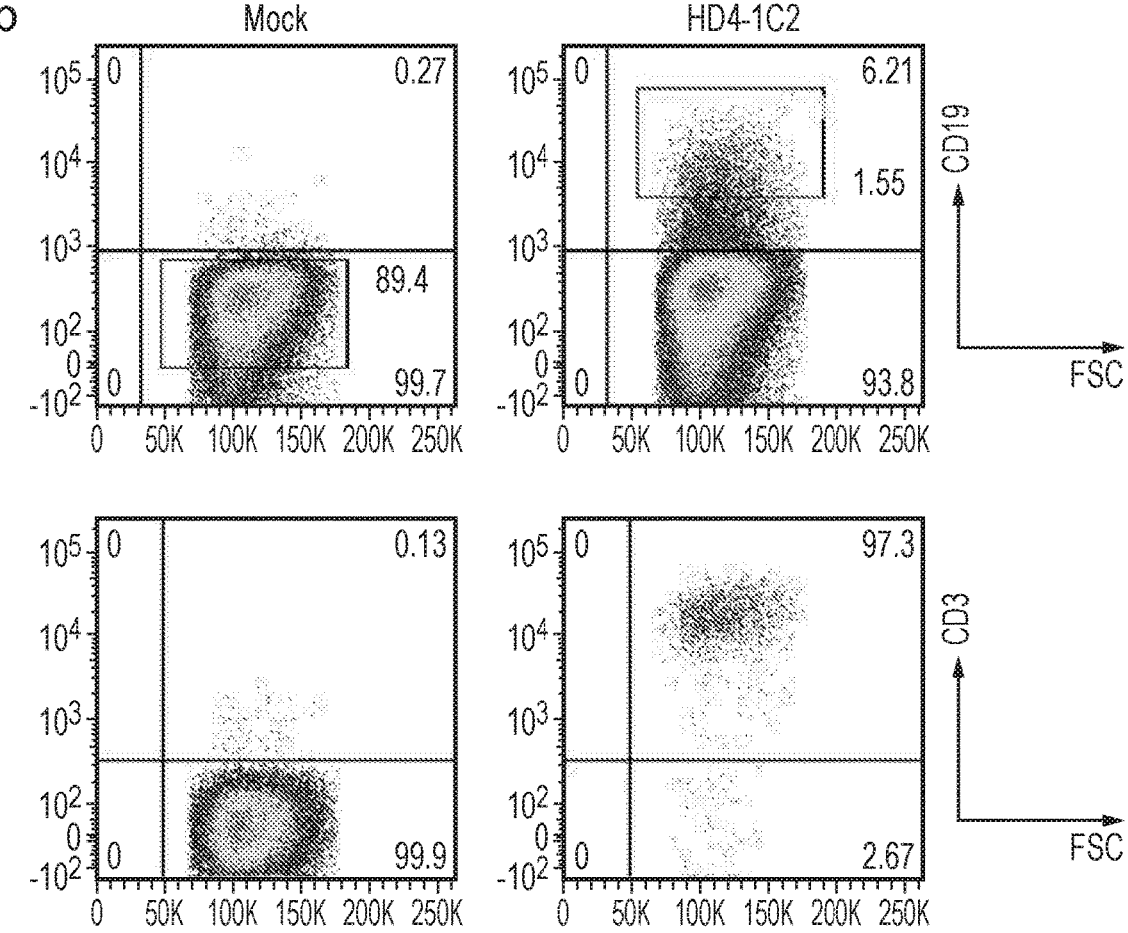

FIG. 7—Characterisation of Ob-2F3
FIG. 8—Characterisation of Ob-3D1
FIG. 9—Characterisation of Hy-1A8
FIG. 10—Characterisation of Hy-2E11
FIG. 11—Characterisation of H D1-14
FIG. 12—Characterisation of MS3-1
FIG. 13—Characterisation of MS3-11
FIG. 14—Characterisation of MS1-4H12
FIG. 15—Characterisation of HD4-1C2

DETAILED DESCRIPTION

Myelin Basic Protein (MBP) Peptides

Myelin basic protein is important in the process of myelination of nerves and is found in the myelin sheath of cells in the nervous system such as oligodendrocytes and Schwann cells. MBP transcripts are also found in the bone marrow and the immune system. One function of the myelin sheath is to increase the velocity of axonal impulse conduction. MBP helps to maintain the correct structure of myelin and interacts with lipids in the myelin membrane. MBP is known to localise to the CNS and to various haematopoietic cells.

MBP has been implicated in the pathogenesis of demyelinating diseases, such as multiple sclerosis (MS). Studies have demonstrated a role for antibodies against MBP in the pathogenesis of MS.

In one aspect, an illustrative amino acid sequence of MBP comprises the sequence with UniProtKB accession P02686-1, shown as SEQ ID NO: 11:

```
                                        (SEQ ID NO: 11)
MGNHAGKRELNAEKASTNSETNRGESEKKRNLGEL

SRTTSEDNEVFGEADANQNNGTSSQDTAVTDSKRT

ADPKNAWQDAHPADPGSRPHLIRLFSRDAPGREDN

TFKDRPSESDELQTIQEDSAATSESLDVMASQKRP

SQRHGSKYLATASTMDHARHGFLPRHRDTGILDSI

GRFFGGDRGAPKRGSGKDSHHPARTAHYGSLPQKS

HGRTQDENPVVHFFKNIVTPRTPPPSQGKGRGLSL

SRFSWGAEGQRPGFGYGGRASDYKSAHKGFKGVDA

QGTLSKIFKLGGRDSRSGSPMARR.
```

An illustrative amino acid sequence of MBP may comprise SEQ ID NO: 11 or a variant or fragment thereof.

Suitably, an illustrative amino acid sequence of MBP may be an isoform of UniProtKB accession P02686-1, such as UniProtKB accession P02686-5. Isoform P02686-5 differs from the canonical sequence shown above in SEQ ID NO:11 as follows, amino acid residues 1-133 are missing.

UniProtKB accession P02686-5 is shown as SEQ ID NO: 13:

```
                                        (SEQ ID NO: 13)
MASQKRPSQRHGSKYLATASTMDHARHGFLPRHRD

TGILDSIGRFFGGDRGAPKRGSGKDSHHPARTAHY

GSLPQKSHGRTQDENPVVHFFKNIVTPRTPPPSQG

KGRGLSLSRFSWGAEGQRPGFGYGGRASDYKSAHK

GFKGVDAQGTLSKIFKLGGRDSRSGSPMARR.
```

Unless otherwise stated, MBP XXX-XXX as used herein refers to the numbering used in Muraro et al., JCI 1997; 100, 2, 339-349, incorporated herein by reference or by reference to SEQ ID NO: 13 (not including the initiator methionine). One may determine whether a peptide is capable of being presented by a MHC molecule and recognised by a T cell using methods available in the art. For example, an assay may comprise co-culturing antigen presenting cells (APCs) expressing the MHC:peptide complex to be tested with T cells comprising the TCR defined herein. T cell proliferation may then be measured as an indication of successful presentation of the peptide (for example by carboxyfluorescein succinimidyl ester (CFSE) assay). Alternatively, effector cytokine production may also be measured.

As used herein "specifically binding" means that the TCR binds to the peptide but does not bind to other peptides, or binds at a lower affinity to other peptides.

The binding affinity between two molecules, e.g. a TCR and a peptide, or fragment thereof, may be quantified for example, by determination of the dissociation constant (KD). The KD can be determined by measurement of the kinetics of complex formation and dissociation between the TCR and the peptide, e.g. by the surface plasmon resonance (SPR) method (Biacore™). The rate constants corresponding to the association and the dissociation of a complex are referred to as the association rate constants ka (or kon) and dissociation rate constant kd. (or koff), respectively. KD is related to ka and kd through the equation KD=kd/ka.

Binding affinities associated with different molecular interactions, e.g. comparison of the binding affinity of different TCRs and peptides, may be compared by comparison of the KD values for the individual TCR/peptide complexes.

The peptide may be capable of being presented by any Human Leukocyte Antigen—antigen D Related (HLA-DR).

In one aspect, the peptide is capable of being presented by a HLA-DR15.

In one aspect, the peptide is capable of being presented by a DRB1*1501 molecule.

In one aspect, the peptide has at least 90% identity to MBP 82-102: DENPVVHFFKNIVTPRTPPPS (SEQ ID NO: 12). The MBP peptide may be mutated compared to MBP 82-102 (SEQ ID NO: 12). For example, the MBP peptide may be mutated by amino acid insertion, deletion or substitution, so long as the modified MBP peptide retains the MHC binding specificity of the unmodified peptide, and is capable of being presented to a T cell. The peptide may, for example have 3, 2, 1 or 0 mutations relative to MBP 82-102 (SEQ ID NO: 12). Suitably the peptide may, for example have 3, 2, 1 or 0 conservative mutations relative to MBP 82-102 (SEQ ID NO: 12). Suitably the peptide may, for example have 3, 2, 1 or 0 insertions relative to MBP 82-102 (SEQ ID NO: 12). Suitably the MBP peptide fragment may, for example have 3, 2, 1 or 0 deletions relative to MBP 82-102 (SEQ ID NO: 12). Suitably, the MBP 82-102 (SEQ ID NO: 12) peptide fragment retains the MHC binding specificity of the 82-102 (SEQ ID NO: 12) peptide, and is capable of being presented to a T cell.

T Cell Receptor (TCR)

The variable domain of both the TCR α-chain and β-chain have three hypervariable or complementarity determining regions (CDRs). CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. Framework regions (FRs) are positioned between the CDRs. These regions provide the structure of the TCR variable region.

The TCR of the present invention comprises sufficient of the variable domains thereof to be able to interact with its peptide/MHC complex. Such interaction can be measured using a Biacore™ instrument, for example. Suitably the TCR may interact with HLA-DR15, suitably DRB1*1501.

The repertoire of TCR variable regions is generated by combinatorial joining of variable (V), joining (J) and diversity (D) genes; and by N region diversification (nucleotides inserted by the enzyme deoxynucleotidyl-transferase).

α chains are formed from recombination events between the V and J segments. β chains are formed from recombination events involving the V, D and J segments.

The human TCRα locus, which also includes the TORO locus, is located on chromosome 14 (14q11.2). The TCRβ locus is located on chromosome 7 (7q34). The variable region of the TCRα chain is formed by recombination between one of 46 different Vα (variable) segments and one of 58 Jα (joining) segments (Koop et al.; 1994; Genomics; 19: 478-493 incorporated herein by reference). The variable region of a TCRβ chain is formed from recombination between 54 Vβ, 14 Jβ and 2 Dβ (diversity) segments (Rowen et al.; 1996; Science; 272:1755-1762 incorporated herein by reference).

The V and J (and D as appropriate) gene segments for each TCR chain locus have been identified and the germline sequence of each gene is known and annotated (for example see Scaviner & Lefranc; 2000; Exp Clin Immunogenet; 17:83-96 and Folch & Lefranc; 2000; Exp Clin Immunogenet; 17:42-54, incorporated herein by reference). FR1, CDR1, FR2, CDR2, FR3 and CDR3 of the α chain of natural TCRs are encoded by the Vα gene. FR1, CDR1, FR2, CDR2 and FR3 of the β chain of natural TCRs are encoded by the Vβ gene.

As the germline sequence of each variable gene is known in the art (see Scaviner & Lefranc; as above and Folch & Lefranc; supra) the Vα and/or Vβ of a particular TCR can be sequenced and the germline V segment which is utilised in the TCR can be identified (see, for example, Hodges et al.; 2003; J Clin Pathol; 56:1-11, Zhou et al.; 2006; Laboratory Investigation; 86; 314-321, incorporated herein by reference).

The present invention provides an engineered Treg comprising an engineered T cell receptor.

The invention provides an engineered Treg comprising a TCR which is capable of specifically binding to a peptide which comprises at least 90% identity to MBP 82-102 (SEQ ID NO: 12) or a fragment thereof when the peptide is presented by a major histocompatibility complex (MHC) molecule.

In one aspect, the TCR comprises an α chain and a β chain, wherein the α chain and the β chain each comprises three complementarity determining regions (CDRs) and the sequence of each CDR3 is as follows:

```
        CDR3α
                                    (SEQ ID NO: 1)
        ATDTTSGTYKYI

CDR3β
                                    (SEQ ID NO: 2)
        SARDLTSGANNEQF
``` or a variant of those sequences having up to three amino acid changes.

In one aspect, the α chain of the TCR comprises three CDRs having the following amino acid sequences:

```
        CDR1α
                                    (SEQ ID NO: 3)
        TSINN

CDR2α
                                    (SEQ ID NO: 4)
        IRSNERE

CDR3α
                                    (SEQ ID NO: 1)
        ATDTTSGTYKYI
``` or variants of those sequences having up to three amino
acid changes;
and wherein the β chain of the TCR comprises three
CDRs having the following amino acid sequences:

```
CDR1β
                            (SEQ ID NO: 5)
DFQATT

CDR2β
                            (SEQ ID NO: 6)
SNEGSKA

CDR3β
                            (SEQ ID NO: 2)
SARDLTSGANNEQF
``` or variants of those sequences having up to three amino
acid changes.

Suitably the amino acid change in a CDR is a conservative
substitution, insertion or deletion. Preferably the amino acid
change is a conservative substitution.

In one aspect, the variable region of the α chain of the
TCR comprises an amino acid sequence having at least 80%
sequence identity to SEQ ID NO:7, and the variable region
of the β chain of the TCR comprises an amino acid sequence
having at least 80% sequence identity to SEQ ID NO: 8,
wherein the sequence identity does not include the CDR
sequences. Suitably the CDR sequences are as disclosed
herein.

Suitably, the variable region of the α chain of the TCR
comprises an amino acid sequence having at least 80%,
85%, 90%, 95% or 97% sequence identity to SEQ ID NO:
7, and the variable region of the β chain of the TCR
comprises an amino acid sequence having at least 80%,
85%, 90%, 95%, or 97% sequence identity to SEQ ID NO:
8.

Suitably, the variable region of the α chain of the TCR
comprises an amino acid sequence may have at least 85%
sequence identity to SEQ ID NO: 7, and the variable region
of the β chain of the TCR comprises an amino acid sequence
having at least 85% sequence identity to SEQ ID NO: 8,
wherein the sequence identity does not include the CDR
sequences. Suitably, the variable region of the α chain of the
TCR comprises an amino acid sequence may have at least
90% sequence identity to SEQ ID NO: 7, and the variable
region of the β chain of the TCR comprises an amino acid
sequence having at least 90% sequence identity to SEQ ID
NO: 8, wherein the sequence identity does not include the
CDR sequences. Suitably, the variable region of the α chain
of the TCR comprises an amino acid sequence may have at
least 95% sequence identity to SEQ ID NO: 7 and the
variable region of the β chain of the TCR comprises an
amino acid sequence having at least 95% sequence identity
to SEQ ID NO: 8, wherein the sequence identity does not
include the CDR sequences. Suitably, the variable region of
the α chain of the TCR comprises an amino acid sequence
may have at least 97% sequence identity to SEQ ID NO: 7
and the variable region of the β chain of the TCR comprises
an amino acid sequence having at least 97% sequence
identity to SEQ ID NO: 8, wherein the sequence identity
does not include the CDR sequences. Suitably, the variable
region of the α chain of the TCR comprises an amino acid
sequence set forth in SEQ ID NO: 7 and the variable region
of the β chain of the TCR comprises an amino acid sequence
set forth in SEQ ID NO: 8, wherein the sequence identity
does not include the CDR sequences.

In other words, the TCR may comprise the α chain and β
chain CDRs as defined herein, and at least 80%, 85%, 90%,
95% or 97% sequence identity across the remaining
sequence of SEQ ID NO: 7 and/or SEQ ID NO: 8.

In another aspect, the variable region of the α chain of the
TCR comprises an amino acid sequence having at least 80%
sequence identity to SEQ ID NO: 7; and the variable region
of the β chain of the TCR comprises an amino acid sequence
having at least 80% sequence identity to SEQ ID NO: 8.

Suitably, the variable region of the α chain of the TCR
comprises an amino acid sequence having at least 85%
sequence identity to SEQ ID NO: 7; and the variable region
of the β chain of the TCR comprises an amino acid sequence
having at least 85% sequence identity to SEQ ID NO: 8.
Suitably, the variable region of the α chain of the TCR
comprises an amino acid sequence having at least 90%
sequence identity to SEQ ID NO: 7; and the variable region
of the β chain of the TCR comprises an amino acid sequence
having at least 90% sequence identity to SEQ ID NO: 8.
Suitably, the variable region of the α chain of the TCR
comprises an amino acid sequence having at least 95%
sequence identity to SEQ ID NO: 7 and the variable region
of the β chain of the TCR comprises an amino acid sequence
having at least 95% sequence identity to SEQ ID NO: 8.
Suitably, the variable region of the α chain of the TCR
comprises an amino acid sequence having at least 97%
sequence identity to SEQ ID NO: 7; and the variable region
of the β chain of the TCR comprises an amino acid sequence
having at least 97% sequence identity to SEQ ID NO: 8.

```
Illustrative TCR α chain variable
region
                            (SEQ ID NO: 7)
SQQGEEDPQALSIQEGENATMNCSYKTSINNLQWY

RQNSGRGLVHLILIRSNEREKHSGRLRVTLDTSKK

SSSLLITASRAADTASYFCATDTTSGTYKYIFGTG

TRLKVLAN

Illustrative TCR β chain variable
region
                            (SEQ ID NO: 8)
GAVVSQHPSWWICKSGTSVKIECRSLDFQATTMFW

YRQFPKQSLMLMATSNEGSKATYEQGVEKDKFLIN

HASLTLSTLTVTSAHPEDSSFYICSARDLTSGANN

EQFFGPGTRLTVL
```

In one aspect, the α chain of the TCR comprises an amino
acid sequence having at least 80% sequence identity to SEQ
ID NO: 9; and the β chain of the TCR comprises an amino
acid sequence having at least 80% sequence identity to SEQ
ID NO: 10.

```
Illustrative TCR α chain
                            (SEQ ID NO: 9)
SQQGEEDPQALSIQEGENATMNCSYKTSINNLQWY

RQNSGRGLVHLILIRSNEREKHSGRLRVTLDTSKK

SSSLLITASRAADTASYFCATDTTSGTYKYIFGTG

TRLKVLANIQNPDPAVYQLRDSKSSDKSVCLFTDF

DSQTNVSQSKDSDVYITDKTVLDMRSMDFKSNSAV

AWSNKSDFACANAFNNSHPEDTFFPSPESSCDVKL
```

-continued

VEKSFETDTNLNFQNLSVIGFRILLLKVAGFNLLM

TLRLWSS

Illustrative TCR β chain
(SEQ ID NO: 10)
GAVVSQHPSWWICKSGTSVKIECRSLDFQATTMFW

YRQFPKQSLMLMATSNEGSKATYEQGVEKDKFLIN

HASLTLSTLTVTSAHPEDSSFYICSARDLTSGANN

EQFFGPGTRLTVLEDLKNVFPPEVAVFEPSEAEIS

HTQKATLVCLATGFYPDHVELSWWVNGKEVHSGVS

TDPQPLKEQPALNDSRYCLSSRLRVSATFWQNPRN

HFRCQVQFYGLSENDEWTQDRAKPVTQIVSAEAWG

RADCGFTSESYQQGVLSATILYEILLGKATLYAV

LVSALVLMAMVKRKDSRG

Suitably, the β chain of the TCR comprises a human constant region amino acid sequence which comprises a cysteine residue at position 22 of constant region (underlined) as shown in SEQ ID NO: 10.

Suitably, the α chain of the TCR comprises an amino acid sequence having at least 85% sequence identity to SEQ ID NO: 9; and the β chain of the TCR comprises an amino acid sequence having at least 85% sequence identity to SEQ ID NO: 10. Suitably, the α chain of the TCR comprises an amino acid sequence having at least 90% sequence identity to SEQ ID NO: 9; and the β chain of the TCR comprises an amino acid sequence having at least 90% sequence identity to SEQ ID NO: 10. Suitably, the α chain of the TCR comprises an amino acid sequence having at least 95% sequence identity to SEQ ID NO: 9; and the β chain of the TCR comprises an amino acid sequence having at least 95% sequence identity to SEQ ID NO: 10.

Suitably, the α chain of the TCR comprises an amino acid sequence having at least 97% sequence identity to SEQ ID NO: 9; and the β chain of the TCR comprises an amino acid sequence having at least 97% sequence identity to SEQ ID NO: 10.

In another aspect, the constant region domains of the α chain and β chain of the TCR each comprise an additional cysteine residue, enabling the formation of an extra disulphide bond between the α chain and the β chain.

Suitably, residue 48 in the constant alpha chain is converted from a threonine to a cysteine and residue 57 of the constant beta chain is converted from a serine to a cysteine for the formation of the additional disulphide bond.

Suitably, the TCR is codon optimised.

Suitably, the TCR is codon optimised for expression in a mouse.

In one aspect the constant domains employed in the TCR are murine sequences.

Suitably the constant regions have been murinised. For example, both the constant-alpha and the constant-beta domains have been murinised.

In another aspect, the TCR is codon optimised for expression in a human. Suitably, the constant domains employed in the TCR are human sequences.

In one aspect the TCR may comprise, for example, human variable regions and murine constant regions.

The present TCR may comprise one or more amino acid residues as defined herein which is not encoded by the germline Vα or Vβ gene. In other words, the TCR may comprise part of an α chain and/or β chain which comprises an altered amino acid residue at one or more of the positions described herein, compared to the corresponding α chain and/or β chain as encoded by the unaltered germline Vα or Vβ gene.

The amino acid residues identified herein as framework (FR) or complementarity-determining regions (CDRs) are identified according to the International ImMunoGeneTics information system' (IMGT). This system is well known in the art (Lefrance et al.; 2003; Dev Comp Immunol; 27: 55-77) and is based on the high conservation of the structure of the variable region. The numbering takes into account and combines the definition of the FR and CDRs, structural data from X-ray diffraction studies and the characterization of the hypervariable loops.

The delimitations of the FR and CDR regions are defined within the IMGT numbering system. The FR1 region comprises positions 1-26 (25-26 amino acids, depending on the V-GENE group or subgroup) with 1st-CYS at position 23. The FR2 region comprises positions 39-55 (16-17 amino acids) with a conserved TRP at position 41. The FR3 region comprises positions 66-104 (36-39 amino acids, depending on the VGENE group or subgroup) with a conserved hydrophobic amino acid at position 89 and the 2nd-CYS at position 104. Residue 1 of the IGMT numbering system is the first residue in FR1. Residue 104 of the IGMT numbering system is the last residue in FR3.

Methods suitable for generating a TCR according to the present invention are known in the art.

For example mutagenesis may be performed to alter specific nucleotides in a nucleic acid sequence encoding the TCR. Such mutagenesis will alter the amino acid sequence of the TCR so that it comprises one or more of the amino acid residues as described herein.

An example of a mutagenesis method is the Quikchange method (Papworth et al.; 1996; Strategies; 9(3); 3-4). This method involves the use of a pair of complementary mutagenic primers to amplify a template nucleic acid sequence in a thermocycling reaction using a high-fidelity non-strand-displacing DNA polymerase, such as pfu polymerase.

The terms "one or more" or "at least one" as used herein may include one, two, three, four, five, six, seven, eight, nine, ten, eleven, twelve, thirteen, fourteen, fifteen, sixteen, seventeen, eighteen, nineteen, twenty or more amino acid residues as described herein.

The term "two or more" as used herein may include two, three, four, five, six, seven, eight, nine, ten, eleven, twelve, thirteen, fourteen, fifteen, sixteen, seventeen, eighteen, nineteen, twenty or more amino acid residues as described herein.

Conservative Substitution

Suitably, the amino acid residues present at a given position in the present invention may be defined as a residue which is biochemically similar to the amino acids recited for the given SEQ ID NOs.

Amino acids with similar biochemical properties may be defined as amino acids which can be substituted via a conservative substitution.

Conservative amino acid substitutions may be made on the basis of similarity in polarity, charge, solubility, hydrophobicity, hydrophilicity, and/or the amphipathic nature of the residues as long as high expression of the TCR is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to Table 3 below. Amino acids in the same block in the second column and preferably in the same line in the third column may be substituted for each other:

TABLE 3

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

The present invention also encompasses homologous substitution (substitution and replacement are both used herein to mean the interchange of an existing amino acid residue, with an alternative residue) i.e. like-for-like substitution such as basic for basic, acidic for acidic, polar for polar etc.

Unless otherwise explicitly stated herein by way of reference to a specific, individual amino acid, amino acids may be substituted using conservative substitutions as recited below.

An aliphatic, non-polar amino acid may be a glycine, alanine, proline, isoleucine, leucine or valine residue.

An aliphatic, polar uncharged amino may be a cysteine, serine, threonine, methionine, asparagine or glutamine residue.

An aliphatic, polar charged amino acid may be an aspartic acid, glutamic acid, lysine or arginine residue.

An aromatic amino acid may be a histidine, phenylalanine, tryptophan or tyrosine residue.

Suitably, a conservative substitution may be made between amino acids in the same line in Table 3.

Sequences

The present invention further provides a nucleotide sequence encoding a TCR α chain and/or β chain described herein. In one aspect, a nucleotide sequence encoding a TCR described herein may be introduced into a cell.

Suitably, the nucleotide sequence encoding the TCR α chain variable regions may comprise SEQ ID NO: 14 or a sequence having at least 80% sequence identity to SEQ ID NO: 14. Suitably, the nucleotide sequence may have at least 85%, 90%, 95%, or 99% identity to SEQ ID NO: 14.

```
                                      SEQ ID NO: 14
AGCCAGCAGGGCGAAGAGGATCCCCAGGCTCTGTC

TATTCAAGAGGGCGAGAACGCCACCATGAACTGCA

GCTACAAGACCAGCATCAACAACCTGCAGTGGTAC

AGACAGAACAGCGGCAGAGGACTGGTGCACCTGAT

CCTGATCAGAAGCAACGAGAGAGAGAAGCACTCCG

GCAGACTGAGAGTGACCCTGGACACCAGCAAGAAG

TCCAGCAGCCTGCTGATCACAGCCAGCAGAGCCGC

CGATACCGCCAGCTACTTTTGTGCCACCGATACCA
```

```
CCTCCGGCACCTACAAGTACATCTTCGGCACCGGC

ACCAGACTGAAGGTGCTGGCCAAC
```

Suitably, the nucleotide sequence encoding the TCR β chain variable regions may comprise SEQ ID NO: 15 or a sequence having at least 80% sequence identity to SEQ ID NO: 15. Suitably, the nucleotide sequence may have at least 85%, 90%, 95%, or 99% identity to SEQ ID NO: 15.

```
                                      SEQ ID NO: 15
GGAGCTGTGGTGTCTCAGCACCCCTCTTGGGTCAT

CTGCAAGAGCGGCACCAGCGTGAAGATCGAGTGCA

GAAGCCTGGACTTCCAGGCCACCACCATGTTTTGG

TACAGGCAGTTCCCCAAGCAGAGCCTGATGCTGAT

GGCCACCTCTAACGAGGGCAGCAAGGCCACATATG

AGCAGGGCGTCGAGAAGGACAAGTTCCTGATCAAC

CACGCCAGCCTGACACTGAGCACCCTGACAGTGAC

AAGCGCCCATCCTGAGGACAGCAGCTTCTACATCT

GCAGCGCCAGGGATCTGACAAGCGGCGCCAACAAC

GAGCAGTTCTTTGGCCCTGGCACCAGGCTGACAGT

GCTC
```

Suitably, the nucleotide sequence encoding the TCR α chain may comprise SEQ ID NO: 16 or a sequence having at least 80% sequence identity to SEQ ID NO: 16. Suitably, the nucleotide sequence may have at least 85%, 90%, 95%, or 99% identity to SEQ ID NO: 16.

```
                                      SEQ ID NO: 16
AGCCAGCAGGGCGAAGAGGATCCCCAGGCTCTGTC

TATTCAAGAGGGCGAGAACGCCACCATGAACTGCA

GCTACAAGACCAGCATCAACAACCTGCAGTGGTAC

AGACAGAACAGCGGCAGAGGACTGGTGCACCTGAT

CCTGATCAGAAGCAACGAGAGAGAGAAGCACTCCG

GCAGACTGAGAGTGACCCTGGACACCAGCAAGAAG

TCCAGCAGCCTGCTGATCACAGCCAGCAGAGCCGC

CGATACCGCCAGCTACTTTTGTGCCACCGATACCA

CCTCCGGCACCTACAAGTACATCTTCGGCACCGGC

ACCAGACTGAAGGTGCTGGCCAACATTCAGAACCC

CGATCCTGCCGTGTACCAGCTGAGAGACAGCAAGA

GCAGCGACAAGAGCGTGTGCCTGTTCACCGACTTC

GACAGCCAGACCAACGTGTCCCAGAGCAAGGACTC

CGATGTGTATATCACCGACAAGACCGTGCTGGACA

TGCGGAGCATGGACTTCAAGAGCAACAGCGCCGTG

GCCTGGTCCAACAAGAGCGATTTCGCCTGCGCCAA

CGCCTTCAACAACAGCATTATCCCCGAGGACACAT

TCTTCCCAAGTCCTGAGAGCAGCTGCGACGTGAAG
```

-continued

CTGGTGGAAAAGAGCTTCGAGACAGACACCAACCT

GAACTTCCAGAACCTGAGCGTGATCGGCTTCAGAA

TCCTGCTGCTGAAGGTGGCCGGCTTCAACCTGCTG

ATGACCCTGAGACTTTGGAGCAGC

Suitably, the nucleotide sequence encoding the TCR β chain may comprise SEQ ID NO: 17 or a sequence having at least 80% sequence identity to SEQ ID NO: 17. Suitably, the nucleotide sequence may have at least 85%, 90%, 95%, or 99% identity to SEQ ID NO: 17.

SEQ ID NO: 17

GGAGCTGTGGTGTCTCAGCACCCCTCTTGGGTCAT

CTGCAAGAGCGGCACCAGCGTGAAGATCGAGTGCA

GAAGCCTGGACTTCCAGGCCACCACCATGTTTTGG

TACAGGCAGTTCCCCAAGCAGAGCCTGATGCTGAT

GGCCACCTCTAACGAGGGCAGCAAGGCCACATATG

AGCAGGGCGTCGAGAAGGACAAGTTCCTGATCAAC

CACGCCAGCCTGACACTGAGCACCCTGACAGTGAC

AAGCGCCCATCCTGAGGACAGCAGCTTCTACATCT

GCAGCGCCAGGGATCTGACAAGCGGCGCCAACAAC

GAGCAGTTCTTTGGCCCTGGCACCAGGCTGACAGT

GCTCGAGGACCTGAAGAACGTGTTCCCACCTGAGG

TGGCCGTGTTCGAGCCTTCTGAGGCCGAGATCTGT

CACACCCAGAAAGCCACACTCGTGTGTCTGGCCAC

CGGCTTCTACCCCGATCACGTGGAACTGTCTTGGT

GGGTCAACGGCAAAGAGGTGCACAGCGGCGTCAGC

ACAGATCCCCAGCCACTGAAAGAACAGCCCGCTCT

GAACGACAGCCGGTACTGTCTGTCTAGCCGGCTGA

GAGTGTCCGCCACCTTCTGGCAGAACCCCAGAAAC

CACTTCAGATGCCAGGTGCAGTTCTACGGCCTGAG

CGAGAACGATGAGTGGACCCAGGATAGAGCCAAGC

CTGTGACACAGATCGTGTCTGCCGAAGCCTGGGGC

AGAGCCGATTGTGGCTTTACCAGCGAGAGCTACCA

GCAAGGCGTGCTGTCTGCCACCATCCTGTACGAGA

TCCTGCTGGGCAAAGCCACTCTGTACGCCGTGCTG

GTTTCTGCCCTGGTCCTGATGGCTATGGTCAAGCG

GAAGGACTCTAGAGGC

As used herein, the term "introduced" refers to methods for inserting foreign DNA into a cell. As used herein the term introduced includes both transduction and transfection methods. Transfection is the process of introducing nucleic acids into a cell by non-viral methods. Transduction is the process of introducing foreign DNA into a cell via a viral vector.

As used herein, the terms "polynucleotide" and "nucleic acid" are intended to be synonymous with each other. The nucleic acid sequence may be any suitable type of nucleotide sequence, such as a synthetic RNA/DNA sequence, a cDNA sequence or a partial genomic DNA sequence.

The term "polypeptide" as used herein is used in the normal sense to mean a series of residues, typically L-amino acids, connected one to the other typically by peptide bonds between the α-amino and carboxyl groups of adjacent amino acids. The term is synonymous with "protein".

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The polynucleotide may be in isolated or recombinant form. It may be incorporated into a vector and the vector may be incorporated into a host cell. Such vectors and suitable hosts form yet further aspects of the present invention.

The polynucleotide may be double or single stranded, and may be RNA or DNA.

The polynucleotide may be codon optimised. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. Suitably the polynucleotide may be codon optimised for expression in a murine model of disease. Suitably, the polynucleotide may be codon optimised for expression in a human subject.

Many viruses, including HIV and other lentiviruses, use a large number of rare codons and by changing these to correspond to commonly used mammalian codons, increased expression of the packaging components in mammalian producer cells can be achieved. Codon usage tables are known in the art for mammalian cells, as well as for a variety of other organisms.

Codon optimisation may also involve the removal of mRNA instability motifs and cryptic splice sites.

The polynucleotide may comprise a nucleic acid sequence which enables both a nucleic acid sequence encoding an α chain and a nucleic acid sequence a β chain to be expressed from the same mRNA transcript.

For example, the polynucleotide may comprise an internal ribosome entry site (IRES) between the nucleic acid sequences which encode the α chain and the β chain. An IRES is a nucleotide sequence that allows for translation initiation in the middle of a mRNA sequence.

The polynucleotide may comprise a nucleic acid sequence encoding an α chain and a nucleic acid sequence a β chain linked by an internal self-cleaving sequence.

The internal self-cleaving sequence may be any sequence which enables the polypeptide comprising the α chain and the polypeptide comprising the β chain to become separated.

The cleavage site may be self-cleaving, such that when the polypeptide is produced, it is immediately cleaved into individual peptides without the need for any external cleavage activity.

The term "cleavage" is used herein for convenience, but the cleavage site may cause the peptides to separate into individual entities by a mechanism other than classical cleavage. For example, for the Foot-and-Mouth disease virus (FMDV) 2A self-cleaving peptide, various models have been proposed for to account for the "cleavage" activity: proteolysis by a host-cell proteinase, autoproteolysis or a translational effect (Donnelly et al (2001) J. Gen. Virol. 82:1027-1041 incorporated herein by reference). The exact mechanism of such "cleavage" is not important for the purposes of the present invention, as long as the cleavage site, when positioned between nucleic acid sequences which encode proteins, causes the proteins to be expressed as separate entities.

The self-cleaving peptide may be a 2A self-cleaving peptide from an aphtho- or a cardiovirus.

A variant can be considered in terms of similarity (i.e. amino acid residues having similar chemical properties/ functions), preferably a variant is expressed in terms of sequence identity.

Sequence comparisons can be conducted by eye, or more usually, with the aid of readily available sequence comparison programs. These publicly and commercially available computer programs can calculate sequence identity between two or more sequences.

Sequence identity may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % sequence identity therefore firstly requires the production of an optimal alignment, taking into consideration gap penalties. A suitable computer program for carrying out such an alignment is the GCG Wisconsin Bestfit package (University of Wisconsin, U.S.A; Devereux et al., 1984, Nucleic Acids Research 12:387 incorporated herein by reference). Examples of other software than can perform sequence comparisons include, but are not limited to, the BLAST package (see Ausubel et al., 1999 ibid—Chapter 18), FASTA (Atschul et al., 1990, J. Mol. Biol., 403-410 incorporated herein by reference) and the GENEWORKS suite of comparison tools. Both BLAST and FASTA are available for offline and online searching (see Ausubel et al., 1999 ibid, pages 7-58 to 7-60 incorporated herein by reference). However it is preferred to use the GCG Bestfit program.

In one embodiment, the sequence identity is determined across the entirety of the sequence. In one embodiment, the sequence identity is determined across the entirety of the candidate sequence being compared to a sequence recited herein.

Although the final sequence identity can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % sequence identity. The software typically does this as part of the sequence comparison and generates a numerical result.

The term "variant" according to the present invention includes any substitution of, variation of, modification of, replacement of, deletion of or addition of one (or more) amino acids from or to the sequence providing the resultant amino acid sequence retains substantially the same activity as the unmodified sequence. For example, conservative amino acid substitutions may be made. As used herein, a variant polypeptide is taken to include a polypeptide comprising an amino acid sequence which is at least 70, 80, 85, 90, 95, 98 or 99% identical to a sequence shown herein.

In one aspect, the variant maintains the function of the parent sequence.

FOXP3

In one aspect, a cell according to the invention comprises a nucleotide sequence which encodes a FOXP3 protein that has also been introduced to the cell.

In one aspect, the cell, engineered Treg or pharmaceutical composition of the present invention may comprise an engineered nucleic acid sequence which encodes a FOXP3 protein, in other words the engineered nucleic acid sequence is not part of the endogenous genome of the cell.

FOXP3 is a member of the FOX protein family of transcription factors and functions as a master regulator of the regulatory pathway in the development and function of regulatory T cells.

Suitably, the FOXP3 polypeptide is from a human e.g. the UniProtKB accession: Q9BZS1:

```
                                    (SEQ ID NO: 18)
MPNPRPGKPSAPSLALGPSPGASPSWRAAPKASDL

LGARGPGGTFQGRDLRGGAHASSSSLNPMPPSQLQ

LPTLPLVMVAPSGARLGPLPHLQALLQDRPHFMHQ

LSTVDAHARTPVLQVHPLESPAMISLTPPTTATGV

FSLKARPGLPPGINVASLEWVSREPALLCTFPNPS

APRKDSTLSAVPQSSYPLLANGVCKWPGCEKVFEE

PEDFLKHCQADHLLDEKGRAQCLLQREMVQSLEQQ

LVLEKEKLSAMQAHLAGKMALTKASSVASSDKGSC

CIVAAGSQGPVPAWSGPREAPDSLFAVRRHLWGSH

GNSTFPEFLHNMDYFKFHNMRPPFTYATLIRWAIL

EAPEKQRTLNEIYHWFTRMFAFFRNHPATWKNAIR

HNLSLHKCFVRVESEKGAVWTVDELEFRKKRSQRP

SRCSNPTPGP
```

Suitably, the FOXP3 polypeptide comprises an amino acid sequence set forth in SEQ ID NO: 18, or a fragment thereof. Suitably the FOXP3 polypeptide comprises an amino acid sequence which is at least 80% identical to SEQ ID NO: 18 or a fragment thereof. Suitably, the polypeptide comprises an amino acid sequence which is 85, 90, 95, 98 or 99% identical to SEQ ID NO: 18 or a fragment thereof. Suitably the fragment retains FOXP3 activity. Suitably the fragment is able to bind to FOXP3 targets and act as a transcription factor.

Suitably, the FOXP3 polypeptide may be a natural variant of SEQ ID NO: 18. Suitably, the FOXP3 polypeptide is an isoform of SEQ ID NO: 18. For example, the FOXP3 polypeptide may comprise a deletion of amino acid positions 72-106 relative to SEQ ID NO: 18. Alternatively, the FOXP3 polypeptide may comprise a deletion of amino acid positions 246-272 relative to SEQ ID NO: 18.

Suitably, the FOXP3 polypeptide comprises the amino acid sequence set forth in SEQ ID NO: 19:

```
                                    (SEQ ID NO: 19)
MPNPRPGKPSAPSLALGPSPGASPSWRAAPKASDL

LGARGPGGTFQGRDLRGGAHASSSSLNPMPPSQLQ

LPTLPLVMVAPSGARLGPLPHLQALLQDRPHFMHQ

LSTVDAHARTPVLQVHPLESPAMISLTPPTTATGV

FSLKARPGLPPGINVASLEVWSREPALLCTFPNPS

APRKDSTLSAVPQSSYPLLANGVCKWPGCEKVFEE

PEDFLKHCQADHLLDEKGRAQCLLQREMVQSLEQV

EELSAMQAHLAGKMALTKASSVASSDKGSCCIVAA

GSQGPVVPAWSGPREAPDSLFAVRRHLWGSHGNST
```

```
-continued
FPEFLHNMDYFKFHNMRPPFTYATLIRWAILEAPE

KQRTLNEIYHWFTRMFAFFRNHPATWKNAIRHNLS

LHKCFVRVESEKGAVWTVDELEFRKKRSQRPSRCS

NPTPGPEGRGSLLTCGDVEEN.
```

Suitably, the FOXP3 polypeptide comprises an amino acid sequence set forth in SEQ ID NO: 19, or a fragment thereof. Suitably the FOXP3 polypeptide comprises an amino acid sequence which is at least 80% identical to SEQ ID NO: 19 or a fragment thereof. Suitably, the polypeptide comprises an amino acid sequence which is 85, 90, 95, 98 or 99% identical to SEQ ID NO: 19 or a fragment thereof. Suitably the fragment retains FOXP3 activity. Suitably the fragment is able to bind to FOXP3 targets and act as a transcription factor.

Suitably, the FOXP3 polypeptide may be a natural variant of SEQ ID NO: 19. Suitably, the FOXP3 polypeptide is an isoform of SEQ ID NO: 19. For example, the FOXP3 polypeptide may comprise a deletion of amino acid positions 72-106 relative to SEQ ID NO: 9. Alternatively, the FOXP3 polypeptide may comprise a deletion of amino acid positions 246-272 relative to SEQ ID NO: 19.

Suitably, the FOXP3 polypeptide is encoded by the polynucleotide sequence set forth in SEQ ID NO: 20:

```
                                    (SEQ ID NO: 20)
ATGCCCAACCCCAGGCCTGGCAAGCCCTCGGCCCC

TTCCTTGGCCCTTGGCCCATCCCCAGGAGCCTCGC

CCAGCTGGAGGGCTGCACCCAAAGCCTCAGACCTG

CTGGGGGCCCGGGGCCCAGGGGGAACCTTCCAGGG

CCGAGATCTTCGAGGCGGGGCCCATGCCTCCTCTT

CTTCCTTGAACCCCATGCCACCATCGCAGCTGCAG

CTGCCCACACTGCCCCTAGTCATGGTGGCACCCTC

CGGGGCACGGCTGGGCCCCTTGCCCCACTTACAGG

CACTCCTCCAGGACAGGCCACATTTCATGCACCAG

CTCTCAACGGTGGATGCCCACGCCCGGACCCCTGT

GCTGCAGGTGCACCCCCTGGAGAGCCCAGCCATGA

TCAGCCTCACACCACCCACCACCGCCACTGGGGTC

TTCTCCCTCAAGGCCCGGCCTGGCCTCCCACCTGG

GATCAACGTGGCCAGCCTGGAATGGGTGTCCAGGG

AGCCGGCACTGCTCTGCACCTTCCCAAATCCCAGT

GCACCCAGGAAGGACAGCACCCTTTCGGCTGTGCC

CCAGAGCTCCTACCCACTGCTGGCAAATGGTGTCT

GCAAGTGGCCCGGATGTGAGAAGGTCTTCGAAGAG

CCAGAGGACTTCCTCAAGCACTGCCAGGCGGACCA

TCTTCTGGATGAGAAGGGCAGGGCACAATGTCTCC

TCCAGAGAGATGGTACAGTCTCTGGAGCAGCAG

CTGGTGCTGGAGAAGGAGAAGCTGAGTGCCATGCA

GGCCCACCTGGCTGGGAAAATGGCACTGACCAAGG
```

-continued

```
CTTCATCTGTGGCATCATCCGACAAGGGCTCCTGC

TGCATCGTAGCTGCTGGCAGCCAAGGCCCTGTCGT

CCCAGCCTGGTCTGGCCCCCGGGAGGCCCCTGACA

GCCTGTTTGCTGTCCGGAGGCACCTGTGGGGTAGC

CATGGAAACAGCACATTCCCAGAGTTCCTCCACAA

CATGGACTACTTCAAGTTCCACAACATGCGACCCC

CTTTCACCTACGCCACGCTCATCCGCTGGGCCATC

CTGGAGGCTCCAGAGAAGCAGCGGACACTCAATGA

GATCTACCACTGGTTCACACGCATGTTTGCCTTCT

TCAGAAACCATCCTGCCACCTGGAAGAACGCCATC

CGCCACAACCTGAGTCTGCACAAGTGCTTTGTGCG

GGTGGAGAGCGAGAAGGGGGCTGTGTGGACCGTGG

ATGAGCTGGAGTTCCGCAAGAAACGGAGCCAGAGG

CCCAGCAGGTGTTCCAACCCTACACCTGGCCCCTG

A
```

In some embodiments of the invention, the polynucleotide encoding the FOXP3 polypeptide or variant comprises a polynucleotide sequence which is at least 80% identical to SEQ ID NO: 20 or a functional fragment thereof. Suitably, the polynucleotide encoding the FOXP3 polypeptide or variant comprises a polynucleotide sequence which is at least 85, 90, 95, 98 or 99% identical to SEQ ID NO: 20 or a functional fragment thereof. In some embodiments of the invention, the polynucleotide encoding the FOXP3 polypeptide or variant comprises SEQ ID NO: 20 or a functional fragment thereof.

Suitably, the FOXP3 polypeptide is encoded by the nucleic acid sequence set forth in SEQ ID NO: 21:

```
                                  (SEQ ID NO: 21)
GAATTCGTCGACATGCCCAACCCCAGACCCGGCAA

GCCTTCTGCCCCTTCTCTGGCCCTGGGACCATCTC

CTGGCGCCTCCCCATCTTGGAGAGCCGCCCCTAAA

GCCAGCGATCTGCTGGGAGCTAGAGGCCCTGGCGG

CACATTCCAGGGCAGAGATCTGAGAGGCGGAGCCC

ACGCCTCTAGCAGCAGCCTGAATCCCATGCCCCCT

AGCCAGCTGCAGCTGCCTACACTGCCTCTCGTGAT

GGTGGCCCCTAGCGGAGCTAGACTGGGCCCTCTGC

CTCATCTGCAGGCTCTGCTGCAGGACCGGCCCCAC

TTTATGCACCAGCTGAGCACCGTGGACGCCCACGC

CAGAACACCTGTGCTGCAGGTGCACCCCCTGGAAA

GCCCTGCCATGATCAGCCTGACCCCTCCAACCACA

GCCACCGGCGTGTTCAGCCTGAAGGCCAGACCTGG

ACTGCCCCCTGGCATCAATGTGGCCAGCCTGGAAT

GGGTGTCCCGCGAACCTGCCCTGCTGTGCACCTTC

CCCAATCCTAGCGCCCCCAGAAAGGACAGCACACT
```

-continued

```
GTCTGCCGTGCCCCAGAGCAGCTATCCCCTGCTGG

CTAACGGCGTGTGCAAGTGGCCTGGCTGCGAGAAG

GTGTTCGAGGAACCCGAGGACTTCCTGAAGCACTG

CCAGGCCGACCATCTGCTGGACGAGAAAGGCAGAG

CCCAGTGCCTGCTGCAGCGCGAGATGGTGCAGTCC

CTGGAACAGCAGCTGGTGCTGGAAAAAGAAAAGCT

GAGCGCCATGCAGGCCCACCTGGCCGGAAAGATGG

CCCTGACAAAAGCCAGCAGCGTGGCCAGCTCCGAC

AAGGGCAGCTGTTGTATCGTGGCCGCTGGCAGCCA

GGGACCTGTGGTGCCTGCTTGGAGCGGACCTAGAG

AGGCCCCCGATAGCCTGTTTGCCGTGCGGAGACAC

CTGTGGGGCAGCCACGGCAACTCTACCTTCCCCGA

GTTCCTGCACAACATGGACTACTTCAAGTTCCACA

ACATGAGGCCCCCCTTCACCTACGCCACCCTGATC

AGATGGGCCATTCTGGAAGCCCCCGAGAAGCAGCG

GACCCTGAACGAGATCTACCACTGGTTTACCCGGA

TGTTCGCCTTCTTCCGGAACCACCCCGCCACCTGG

AAGAACGCCATCCGGCACAATCTGAGCCTGCACAA

GTGCTTCGTGCGGGTGGAAAGCGAGAAGGGCGCCG

TGTGGACAGTGGACGAGCTGGAATTTCGGAAGAAG

CGGTCCCAGAGGCCCAGCCGGTGTAGCAATCCTAC

ACCTGGCCCTGAGGGCAGAGGAAGTCTGCTAACAT

GCGGTGACGTCGAGGAGAATCC.
```

Suitably, the FOXP3 polypeptide is encoded by the nucleic acid sequence set forth in SEQ ID NO: 21, or a fragment thereof. Suitably the FOXP3 polypeptide is encoded by a nucleic acid sequence which is at least 80% identical to SEQ ID NO: 21 or a fragment thereof. Suitably, the FOXP3 polypeptide is encoded by the nucleic acid sequence which is 85, 90, 95, 98 or 99% identical to SEQ ID NO: 21 or a fragment thereof. Suitably the fragment retains FOXP3 activity. Suitably the polypeptide encoded by the fragment is able to bind to FOXP3 targets and act as a transcription factor.

The nucleic acid encoding the TCR and/or FOXP3 may comprise a leader sequence upstream of the initiation codon. This sequence may regulate translation of a transcript. By way of example, suitable leader sequences for use in the present invention are:

```
                                  (SEQ ID NO: 22)
METLLGVSLVILWLQLARVN
and (SEQ ID NO: 23)
MLLLLLLLGPGISLLLPGSLAGSGL.
```

In a further aspect the present invention provides a kit of nucleic acid sequences comprising: a first nucleic acid sequence which encodes a TCR as defined herein and a second nucleic acid which encodes FOXP3.

Vector

The present invention also provides a vector comprising a nucleotide sequence encoding a TCR as described herein. Suitably, the vector may additionally comprise a nucleotide sequence encoding a forkhead box P3 (FOXP3) polypeptide. In one aspect, there is provided a kit of vectors which comprises one or more nucleic acid sequence(s) of the invention such as a nucleic acid encoding a TCR as defined herein and a nucleic acid encoding FOXP3.

The term "vector" includes an expression vector, i.e., a construct enabling expression of TCR i.e. an α chain and/or β chain according to the present invention. Suitably the expression vector additionally enables expression of a FOXP3 polypeptide. In some embodiments, the vector is a cloning vector.

Where the vector comprises a polynucleotide encoding a TCR in addition to a polynucleotide encoding FOXP3; the vector may have the orientation of: 5' FOXP3-TCR 3'. Accordingly the polynucleotide encoding a FOXP3 may be 5' to the polynucleotide encoding TCR.

Suitably, the polynucleotide encoding FOXP3 may be separated from the polynucleotide encoding a TCR by a nucleic acid sequence which enables both the nucleic acid sequence encoding FOXP3 and the nucleic acid sequence encoding the TCR to be expressed from the same mRNA transcript.

For example, the polynucleotide may comprise an internal ribosome entry site (IRES) between the nucleic acid sequences which encode (i) FOXP3 and (ii) the TCR. An IRES is a nucleotide sequence that allows for translation initiation in the middle of a mRNA sequence.

The polynucleotide may comprise a nucleic acid sequence encoding (i) FOXP3 and (ii) the TCR linked by an internal self-cleaving sequence. The polynucleotides encoding the TCR α and β chains may also be separated by an internal self-cleaving sequence.

Suitably, the vector may have the structure: 5' Strong promoter (e.g. LTR)-FoxP3-2A-TCR-3'LTR. Here, FOXP3 expression is directly driven by the strong LTR promoter for optimal expression. TCR is preceded by a 2A sequence and expression of the TCR is thus dependent on both LTR promoter activity and 2A cleavage activity. Importantly, a configuration in which FOXP3 precedes TCR in the 5' to 3' direction ensures that TCR expression can only occur when FOXP3 has been expressed and that expression of TCR without FOXP3 does not occur. This is a particular advantage in the present context of an engineered Treg, as it reduces the risk of an engineered Treg acquiring an effector phenotype and/or reduces the risk associated with introducing the TCR into a T effector cell present in a starting population.

The cleaving sequence may be any sequence which enables the polypeptide comprising (i) FOXP3 and (ii) the TCR to become separated.

The cleavage site may be self-cleaving, such that when the polypeptide is produced, it is immediately cleaved into individual peptides without the need for any external cleavage activity.

The term "cleavage" is used herein for convenience, but the cleavage site may cause the peptides to separate into individual entities by a mechanism other than classical cleavage. For example, for the Foot-and-Mouth disease virus (FMDV) 2A self-cleaving peptide, various models have been proposed for to account for the "cleavage" activity: proteolysis by a host-cell proteinase, autoproteolysis or a translational effect (Donnelly et al (2001) J. Gen. Virol. 82:1027-1041 incorporated herein by reference). The exact mechanism of such "cleavage" is not important for the purposes of the present invention, as long as the cleavage site, when positioned between nucleic acid sequences which encode proteins, causes the proteins to be expressed as separate entities.

The self-cleaving peptide may be a 2A self-cleaving peptide from an aphtho- or a cardiovirus.

A variant can be considered in terms of similarity (i.e. amino acid residues having similar chemical properties/functions), preferably a variant is expressed in terms of sequence identity.

Sequence comparisons can be conducted by eye, or more usually, with the aid of readily available sequence comparison programs. These publicly and commercially available computer programs can calculate sequence identity between two or more sequences.

Suitably, the FOXP3 polypeptide expressed from the present vector may be positioned at the N-terminal of a self-cleaving peptide, for example a 2A self-cleaving peptide. Such a FOXP3-2A polypeptide may comprise a sequence shown as SEQ ID NO: 24 or 25; or a variant of SEQ ID NO: 24 or 25 which is at least 80% identical thereto. Suitably, the variant may be at least 85, 90, 95, 98 or 99% identical to SEQ ID NO: 24 or 25.

```
                                    SEQ ID NO: 24
MPNPRPGKPSAPSLALGPSPGASPSWRAAPKASDL

LGARGPGGTFQGRDLRGGAHASSSSLNPMPPSQLQ

LPTLPLVMVAPSGARLGPLPHLQALLQDRPHFMHQ

LSTVDAHARTPVLQVHPLESPAMISLTPPTTATGV

FSLKARPGLPPGINVASLEWVSREPALLCTFPNPS

APRKDSTLSAVPQSSYPLLANGVCKWPGCEKVFEE

PEDFLKHCQADHLLDEKGRAQCLLQREMVQSLEQQ

LVLEKEKLSAMQAHLAGKMALTKASSVASSDKGSC

CIVAAGSQGPVVPAWSGPREAPDSLFAVRRHLWGS

HGNSTFPEFLHNMDYFKFHNMRPPFTYATLIRWAI

LEAPEKQRTLNEIYHWFTRMFAFFRNHPATWKNAI

RHNLSLHKCFVRVESEKGAVWTVDELEFRKKRSQR

PSRCSNPTPGPGATNFSLLKQAGDVEENPGPS

SEQ ID NO: 25
MPNPRPGKPSAPSLALGPSPGASPSWRAAPKASDL

LGARGPGGTFQGRDLRGGAHASSSSLNPMPPSQLQ

LPTLPLVMVAPSGARLGPLPHLQALLQDRPHFMHQ

LSTVDAHARTPVLQVHPLESPAMISLTPPTTATGV

FSLKARPGLPPGINVASLEWVSREPALLCTFPNPS

APRKDSTLSAVPQSSYPLLANGVCKWPGCEKVFEE

PEDFLKHCQADHLLDEKGRAQCLLQREMVQSLEQV

EELSAMQAHLAGKMALTKASSVASSDKGSCCIVAA

GSQGPVPAWSGPREAPDSLFAVRRHLWGSHGNSTF

PEFLHNMDYFKFHNMRPPFTYATLIRWAILEAPEK

QRTLNEIYHWFTRMFAFFRNHPATWKNAIRHNLSL
```

25

```
-continued
HKCFVRVESEKGAVWTVDELEFRKKRSQRPSRCSN

PTPGPEGRGSLLTCGDVEENGATNFSLLKQAGDVE

ENPGPS
```

Suitable vectors may include, but are not limited to, plasmids, viral vectors, transposons, nucleic acid complexed with polypeptide or immobilised onto a solid phase particle.

Viral delivery systems include but are not limited to adenovirus vector, an adeno-associated viral (AAV) vector, a herpes viral vector, retroviral vector, lentiviral vector, baculoviral vector.

Retroviruses are RNA viruses with a life cycle different to that of lytic viruses. In this regard, a retrovirus is an infectious entity that replicates through a DNA intermediate. When a retrovirus infects a cell, its genome is converted to a DNA form by a reverse transcriptase enzyme. The DNA copy serves as a template for the production of new RNA genomes and virally encoded proteins necessary for the assembly of infectious viral particles.

There are many retroviruses, for example murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridiae including lentiviruses.

A detailed list of retroviruses may be found in Coffin et al ("Retroviruses" 1997 Cold Spring Harbour Laboratory Press Eds: J M Coffin, S M Hughes, H E Varmus pp 758-763) incorporated herein by reference.

Lentiviruses also belong to the retrovirus family, but they can infect both dividing and non-dividing cells (Lewis et al (1992) EMBO J. 3053-3058) incorporated herein by reference.

The vector may be capable of transferring a polynucleotide the invention to a cell, for example a host cell as defined herein. The vector should ideally be capable of sustained high-level expression in host cells, so that the α chain and/or β chain are suitably expressed in the host cell.

The vector may be a retroviral vector. The vector may be based on or derivable from the MP71 vector backbone. The vector may lack a full-length or truncated version of the Woodchuck Hepatitis Response Element (WPRE).

For efficient infection of human cells, viral particles may be packaged with amphotropic envelopes or gibbon ape leukemia virus envelopes.

Cell

The present invention further provides a cell e.g. a host cell comprising a polynucleotide or vector according to the invention.

The host cell may be any cell which can be used to express and produce a TCR.

Suitably, the cell is a T cell, such as a conventional T cell.

Suitably, the cell is a Treg cell.

In one aspect, the cell, such as a T cell or Treg, may be isolated from blood obtained from the subject. Suitably, the cell, such as a T cell or Treg, is isolated from peripheral blood mononuclear cells (PBMCs) obtained from the subject.

Suitably, the cell is a natural Treg which expresses FOXP3.

In one aspect, the cell is a stem cell.

In another aspect, the cell is a progenitor cell.

As used herein, the term "stem cell" means an undifferentiated cell which is capable of indefinitely giving rise to more stem cells of the same type, and from which other, specialised cells may arise by differentiation. Stem cells are multipotent. Stem cells may be for example, embryonic stem cells or adult stem cells.

As used herein, the term "progenitor cell" means a cell which is able to differentiate to form one or more types of cells but has limited self-renewal in vitro.

Suitably, the cell is capable of being differentiated into a T cell, such as a Treg.

Suitably, the cell has the ability to differentiate into a T cell, which expresses FOXP3 such as a Treg.

Suitably, the cell is a human cell. Suitable the cell is a human Treg.

Suitably, the cell may be an embryonic stem cell (ESC). Suitably, the cell is a haematopoietic stem cell or haematopoietic progenitor cell. Suitably, the cell is an induced pluripotent stem cell (iPSC). Suitably, the cell may be obtained from umbilical cord blood. Suitably, the cell may be obtained from adult peripheral blood.

In some aspects, hematopoietic stem and progenitor cell (HSPCs) may be obtained from umbilical cord blood. Cord blood can be harvested according to techniques known in the art (e.g., U.S. Pat. Nos. 7,147,626 and 7,131,958 which are incorporated herein by reference).

In one aspect, HSPCs may be obtained from pluripotent stem cell sources, e.g., induced pluripotent stem cells (iP-SCs) and embryonic stem cells (ESCs).

As used herein, the term "hematopoietic stem and progenitor cell" or "HSPC" refers to a cell which expresses the antigenic marker CD34 (CD34+) and populations of such cells. In particular embodiments, the term "HSPC" refers to a cell identified by the presence of the antigenic marker CD34 (CD34+) and the absence of lineage (lin) markers. The population of cells comprising CD34+ and/or Lin(−) cells includes haematopoietic stem cells and hematopoietic progenitor cells.

HSPCs can be obtained or isolated from bone marrow of adults, which includes femurs, hip, ribs, sternum, and other bones. Bone marrow aspirates containing HSPCs can be obtained or isolated directly from the hip using a needle and syringe. Other sources of HSPCs include umbilical cord blood, placental blood, mobilized peripheral blood, Wharton's jelly, placenta, fetal blood, fetal liver, or fetal spleen. In particular embodiments, harvesting a sufficient quantity of HSPCs for use in therapeutic applications may require mobilizing the stem and progenitor cells in the subject.

As used herein, the term "induced pluripotent stem cell" or "iPSC" refers to a non-pluripotent cell that has been reprogrammed to a pluripotent state. Once the cells of a subject have been reprogrammed to a pluripotent state, the cells can then be programmed to a desired cell type, such as a hematopoietic stem or progenitor cell (HSC and HPC respectively).

As used herein, the term "reprogramming" refers to a method of increasing the potency of a cell to a less differentiated state.

As used herein, the term "programming" refers to a method of decreasing the potency of a cell or differentiating the cell to a more differentiated state.

Suitably the cell is matched or is autologous to the subject. The cell may be generated ex vivo either from a patient's own peripheral blood (1st party), or in the setting of a haematopoietic stem cell transplant from donor peripheral blood (2nd party), or peripheral blood from an unconnected donor (3rd party).

Suitably the cell is autologous to the subject. Suitably, the subject is a human.

In some aspects, the cell may be derived from ex-vivo differentiation of inducible progenitor cells or embryonic progenitor cells to the immune cell. In these instances, cells are generated by introducing DNA or RNA coding for the TCR of the present invention by one of many means including transduction with a viral vector, transfection with DNA or RNA.

Suitably, the cells are generated by introducing in addition to the TCR of the invention, DNA or RNA coding for FOXP3 by one of many means including transduction with a viral vector, or transfection with DNA or RNA.

As used herein, the term "conventional T cell" or Tconv means a T lymphocyte cell which expresses an $\alpha\beta$ T cell receptor (TCR) as well as a co-receptor which may be cluster of differentiation 4) CD4 or cluster of differentiation 8 (CD8). Conventional T cells are present in the peripheral blood, lymph nodes, and tissues. FOXP3 is expressed by thymus derived Tregs and can be expressed by recently activated conventional T cells.

As used herein, the term "regulatory T cell" or Treg, means a T cell which expresses the markers CD4, CD25 and FOXP3 ($CD4^+CD25^+FOXP3^+$). Tregs may also be identified using the cell surface markers CD4 and CD25 in the absence of or in combination with low-level expression of the surface protein CD127 ($CD4^+CD25^+CD127^-$). Tregs may also express on the cell surface, high levels of CTLA-4 (cytotoxic T-lymphocyte associated molecule-4) or GITR (glucocorticoid-induced TNF receptor). Unlike conventional T cells, regulatory T cells do not produce IL-2 and are therefore anergic at baseline. Treg cells include thymus-derived, natural Treg (nTreg) cells and peripherally generated, induced Treg (iTreg) cells.

In one aspect, a Treg is $CD4^+CD25^+FOXP3^+$. T cell.

In one aspect, a Treg is a $CD4^+CD25^+CD127^-$ T cell.

In one aspect, a Treg is a $CD4^+CD25^+FOXP3^+CD127^-$ T cell.

As used herein, the term "natural T reg" means a thymus-derived Treg. Natural T regs are $CD4^+CD25^+FOXP3^+$ Helios$^+$ Neuropilin 1$^+$. Compared with iTregs, nTregs have higher expression of PD-1 (programmed cell death-1, pdcd1), neuropilin 1 (Nrp1), Helios (Ikzf2), and CD73. nTregs may be distinguished from iTregs on the basis of the expression of Helios protein or Neuropilin 1 (Nrp1) individually.

As used herein, the term "induced regulatory T cell" (iTreg) means a $CD4^+$ $CD25^+$ FOXP3$^+$ Helios$^-$ Neuropilin 1$^-$ T cell which develops from mature CD4+ conventional T cells outside of the thymus. For example, iTregs can be induced in vitro from CD4+ CD25–FOXP3– cells in the presence of IL-2 and TGF-$\beta$.

The method of the present invention may comprise introducing a first nucleotide sequence encoding the present TCR and a second nucleotide sequence encoding FOXP3 into a natural Treg (which already expresses endogenous FOXP3) as described herein. Suitably, the method of the present invention comprises introducing a vector which comprises a polynucleotide encoding the present TCR in addition to a polynucleotide encoding FOXP3; wherein the vector has the orientation of: 5' FOXP3– TCR 3'—as described herein—into a natural Treg as defined herein. Accordingly the polynucleotide encoding a FOXP3 may be 5' to the polynucleotide encoding TCR. Without wishing to be bound by theory, the present inventors have shown that exogenous FOXP3 expression in regulatory T cell (Tregs) (which already express endogenous FOXP3) enhances their regulatory function. In particular, the present inventors have determined that increasing FOXP3 expression in Tregs which already express endogenous FOXP3 (e.g. by introducing exogenous FOXP3) enhances the regulatory function of the Tregs to a greater degree than the regulatory function provided by expressing exogenous FOXP3 in conventional T cells which do not express endogenous FOXP3. Further, increasing FOXP3 expression in Tregs which already express endogenous FOXP3 enables improved retention of a Treg functional profile in vivo following administration to a subject. For example, it has been determined that natural Tregs which do not express exogenous FOXP3 may lose their Treg profile following administration to a subject—for example natural Tregs which do not express exogenous FOXP may have reduced levels of FOXP3 expression and be capable of producing pro-inflammatory, effector cytokines after a period following administration to a subject. Tregs provided by the present invention may retain FOXP3 expression and have reduced capability to produce pro-inflammatory, effector cytokines after a period following administration to a subject.

Compositions

The present invention also provides a composition comprising an engineered Treg, a vector or a cell according to the invention. Suitably the present invention provides a composition comprising an engineered Treg according to the invention. Suitably the present invention provides a composition comprising a vector according to the invention. Suitably the present invention provides a composition comprising a cell according to the invention.

In some embodiments, the composition is a pharmaceutical composition. Such pharmaceutical composition may comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as (or in addition to) the carrier, excipient or diluent, any suitable binder(s), lubricant(s), suspending agent(s), coating agent(s), solubilising agent(s) and other carrier agents.

The pharmaceutical compositions typically should be sterile and stable under the conditions of manufacture and storage. Formulations for parenteral administration include, but are not limited to, suspensions, solutions, emulsions in oily or aqueous vehicles, pastes, and implantable sustained-release or biodegradable formulations as discussed herein. Sterile injectable formulations may be prepared using a non-toxic parenterally acceptable diluent or solvent. A pharmaceutical composition for use in accordance with the present invention may include pharmaceutically acceptable dispersing agents, wetting agents, suspending agents, isotonic agents, coatings, antibacterial and antifungal agents, carriers, excipients, salts, or stabilizers which are non-toxic to the subjects at the dosages and concentrations employed. Preferably, such a composition can further comprise a pharmaceutically acceptable carrier or excipient for use in the treatment of disease that that is compatible with a given method and/or site of administration, for instance for parenteral (e.g. sub-cutaneous, intradermal, or intravenous injection) or intrathecal administration.

Wherein the pharmaceutical composition comprises a cell according to the invention, the composition may be produced using current good manufacturing practices (cGMP).

Suitably the pharmaceutical composition comprising a cell may comprise an organic solvent, such as but not limited to, methyl acetate, dimethyl sulfoxide (DMSO), N,N-dimethylformamide (DMF), dimethoxyethane (DME), and dimethylacetamide, including mixtures or combinations thereof.

Suitably the pharmaceutical composition comprising a cell is endotoxin free.

Method of Treatment

The present invention provides a method for treating and/or preventing a disease which comprises the step of administering an engineered Treg of the present invention to a subject.

The present invention provides a method for treating and/or preventing a disease which comprises the step of administering a pharmaceutical composition of the present invention to a subject.

The present invention also provides an engineered Treg of the present invention for use in treating and/or preventing a disease.

The present invention also provides a pharmaceutical composition of the present invention for use in treating and/or preventing a disease.

The invention also relates to the use of an engineered Treg, a vector or cell according to the present invention in the manufacture of a medicament for treating and/or preventing a disease.

Preferably, the present methods of treatment relate to the administration of a pharmaceutical composition of the present invention to a subject.

The term "treat/treatment/treating" refers to administering an engineered Treg, cell, vector, or pharmaceutical composition as described herein to a subject having an existing disease or condition in order to lessen, reduce or improve at least one symptom associated with the disease and/or to slow down, reduce or block the progression of the disease.

Reference to "prevention"/"preventing" (or prophylaxis) as used herein refers to delaying or preventing the onset of the symptoms of the disease. Prevention may be absolute (such that no disease occurs) or may be effective only in some individuals or for a limited amount of time.

In a preferred embodiment of the present invention, the subject of any of the methods described herein is a mammal, preferably a cat, dog, horse, donkey, sheep, pig, goat, cow, mouse, rat, rabbit or guinea pig. Preferably the subject is a human.

The administration of a pharmaceutical composition of the invention can be accomplished using any of a variety of routes that make the active ingredient bioavailable. For example, a Treg, cell, vector, or pharmaceutical composition can be administered intravenously, intrathecally, by oral and parenteral routes, intranasally, intraperitoneally, subcutaneously, transcutaneously or intramuscularly.

In one aspect, the engineered Treg according to the invention or the pharmaceutical composition according to the invention is administered intravenously.

In another aspect, the engineered Treg according to the invention or the pharmaceutical composition according to the invention is administered intrathecally.

Typically, a physician will determine the actual dosage that is most suitable for an individual subject and it will vary with the age, weight and response of the particular patient. The dosage is such that it is sufficient to reduce and/or prevent disease symptoms.

Those skilled in the art will appreciate, for example, that route of delivery (e.g., oral vs intravenous vs subcutaneous, etc) may impact dose amount and/or required dose amount may impact route of delivery. For example, where particularly high concentrations of an agent within a particular site or location are of interest, focused delivery may be desired and/or useful. Other factors to be considered when optimizing routes and/or dosing schedule for a given therapeutic regimen may include, for example, the disease being treated (e.g., type or stage, etc.), the clinical condition of a subject (e.g., age, overall health, etc.), the presence or absence of combination therapy, and other factors known to medical practitioners.

The dosage is such that it is sufficient to stabilise or improve symptoms of the disease.

The present invention also provides a method for treating and/or preventing a disease, which comprises the step of administering a pharmaceutical composition comprising a cell e.g. a T cell according to the invention to a subject.

Suitably, the present invention also provides a method for treating and/or preventing a disease, which comprises the step of administering an engineered Treg according to the invention to a subject.

The method may comprise the following steps:
(i) isolation of a cell-containing sample from a subject;
(ii) introducing a nucleic acid sequence encoding a TCR and optionally, a nucleic acid encoding a FOXP3 protein to the cells; and
(iii) administering the cells from (ii) to the subject.

Suitably the cells from (ii) may be expanded in vitro before administration to the subject.

The method may comprise the following steps:
(i) introducing a nucleic acid sequence encoding a TCR and optionally, a nucleic acid encoding a FOXP3 protein to a cell-containing sample; and
(ii) administering the cells from (i) to the subject.

Disease

The disease to be treated and/or prevented by the methods and uses of the present invention may be any disease which induces a T cell mediated immune response.

The disease may be, for example, a cancer, infectious disease or autoimmune disease.

Suitably the disease to be treated and/or prevented by the methods and uses of the present invention may be an autoimmune disease.

Without wishing to be bound by theory, the disease to be treated and/or prevented by the methods and uses of the present invention may be any disease wherein MBP is an antigen e.g. where MBP is a self-antigen.

Suitably the disease may be an autoimmune and inflammatory central nervous system disease (e.g. chronic neurodegenerative conditions).

Suitably the disease may be a chronic neurodegenerative condition such as multiple sclerosis (MS), Alzheimer's disease, Parkinson's disease, neurotropic viral infections, stroke, paraneoplastic disorders and traumatic brain injury.

In one aspect, the disease is multiple sclerosis.

Suitably, the disease is chronic progressive multiple sclerosis.

Suitably, the disease is relapsing/remitting multiple sclerosis.

In one aspect, the disease may have central nervous system (CNS) involvement of systemic autoimmune and inflammatory disease such as Behcet disease, sarcoidosis, systemic lupus erythematosus, juvenile idiopathic arthritis, scleroderma, and Sjögren syndrome.

Suitably, the disease is present in an HLA-DRB1*1501 or DRB1*1503 positive subject.

Suitably, the disease is multiple sclerosis and the subject is HLA-DRB1*1501 or DRB1*1503 positive.

Suitably, the disease is chronic progressive multiple sclerosis and the subject is HLA-DRB1*1501 or DRB1*1503 positive.

Suitably, the disease is relapsing/remitting multiple sclerosis and the subject is HLA-DRB1*1501 or DRB1*1503 positive.

Suitably, the subject is an HLA-DRB1*1501 positive subject.

Multiple Sclerosis

Multiple Sclerosis (MS) is the most common neurological disorder among young adults in Europe and in the USA. MS is characterised as a demyelinating disease and is a chronic degenerative disease of the central nervous system in which gradual destruction of myelin occurs in patches throughout the brain and/or spinal cord, interfering with neural connectivity and causing muscular weakness, loss of coordination and speech and visual disturbances.

Several types or patterns of progression of MS have been identified including, clinically isolated syndrome (CIS), relapsing-remitting MS (RRMS), primary progressive MS (PPMS) and secondary progressive MS (SPMS). For some patients, the increase or progression of disability is very gradual, and for others it can occur more quickly. In general, however, recovery from attacks become less and less complete, and symptoms tend to increase and disability grows.

Although several disease-modifying treatments (DMTs) have been approved to reduce the frequency of clinical relapses, most patients continue to clinically deteriorate under current therapy schedules. Autologous haematopoietic stem cell transplantation can have lasting beneficial effects for patients, but the procedure requires aggressive myeloablative conditioning which is associated with substantial toxicity. Neither DMTs nor stem cell transplantation can mediate antigen-specific suppression of the immunopathology of MS. Without wishing to be bound by theory, in the future, administration of one dose of engineered Treg of the present invention may provide lasting suppression of MS immunopathology in the absence of systemic side effects. This will have a significant impact on the progression of the disease in people with MS.

Suitably, the Treg, vector or pharmaceutical composition of the present invention may reduce or ameliorate one or more of the symptoms of MS, which include reduced or loss of vision, stumbling and uneven gait, slurred speech, urinary frequency and incontinence, mood changes and depression, muscle spasms and paralysis.

Method

The invention also provides a method for producing an engineered Treg which method comprises introducing into a cell in vitro or ex vivo, a polynucleotide encoding a TCR as defined herein. Suitably, the method further comprises incubating the cell under conditions permitting expression of the TCR molecule of the present invention. Optionally, the method may further comprise a step of purifying the engineered Treg cells.

Suitably, the cell is a T cell.

Suitably, the cell is a Treg cell.

Suitably, the cell is a natural Treg which expresses FOXP3.

In one aspect, the cell is a stem cell. Suitably, in the method according to the invention, a nucleic acid encoding TCR as defined herein has been introduced into the stem cell and the stem cell is then differentiated into a T cell such as a Treg which expresses FOXP3.

Suitably, the stem cell has the ability to differentiate into a T cell such as a Treg which expresses FOXP3. Suitably, the cell may be an embryonic stem cell (ESC). Suitably, the cell may be obtained from umbilical cord blood. Suitably, the cell may be obtained from adult peripheral blood. Suitably, the cell is a haematopoietic stem and progenitor cell (HSPC). Suitably, the cell is an induced pluripotent stem cell (iPSC).

In another aspect, the cell is a progenitor cell. Suitably the progenitor cell has the ability to differentiate into a T cell such as a Treg which expresses FOXP3.

In another aspect, the invention provides a method for producing an engineered Treg, which method comprises introducing into a cell in vitro or ex vivo a polynucleotide encoding a TCR as defined herein and a polynucleotide encoding a FOXP3 protein. Suitably, the cell may be a natural Treg as defined herein. Suitably the polynucleotide encoding a TCR as defined herein and the polynucleotide encoding a FOXP3 protein are provided as separate polynucleotides.

Suitably the separate polypeptides are introduced separately, sequentially or simultaneously into the cell. Wherein the polypeptides are introduced separately or sequentially, suitably the polynucleotide encoding the TCR is introduced first. Wherein the polypeptides are introduced separately or sequentially, suitably the polynucleotide encoding FOXP3 is introduced first. Suitably the polynucleotide encoding a TCR as defined herein and the polynucleotide encoding a FOXP3 protein are provided on the same polynucleotide.

In some embodiments, the method according to the invention comprises:

(a) isolating a natural Treg from a cell population; and (b) increasing FOXP3 expression in the natural Treg.

The expression "isolating the Treg from a cell population" means to separate out the Treg from a heterogeneous mixture of multiple different types of cells. Suitable the cell population is from a sample from a human subject.

Suitably, the Treg is isolated as a population of Tregs.

Suitably, the population of Tregs comprises at least 70% Tregs, such as 75%, 85%, 90% or 95% Tregs.

Suitably, the method further comprises incubating the cell under conditions causing expression of FOXP3 and the TCR molecule of the present invention. Optionally, the method may further comprise a step of purifying the engineered Treg cells.

In one aspect, the invention provides a method for producing an engineered Treg, which method comprises introducing into a cell in vitro or ex vivo a polynucleotide encoding a TCR as defined herein and a polynucleotide encoding a FOXP3 protein and differentiating the cell into a T cell, such as a Treg which expresses FOXP3. Suitably, the method further comprises incubating the cell under conditions causing expression of FOXP3 and the TCR molecule of the present invention. Optionally, the method may further comprise a step of purifying the engineered Treg cells.

Suitably, in one aspect the cell is differentiated into a T cell before FOXP3 is introduced into the cell.

Purification of the engineered Treg may be achieved by any method known in the art. Suitably, the engineered Treg may be purified using fluorescence-activated cell sorting (FACS) or immunomagnetic isolation (i.e. using antibodies attached to magnetic nanoparticles or beads) using positive and/or negative selection of cell populations.

Suitably, purification of the engineered T cell may be performed using the expression of the TCR as defined herein.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

It is noted that embodiments of the invention as described herein may be combined.

The publications discussed herein are provided solely for their disclosure prior to the filing date of the present application. Nothing herein is to be construed as an admission that such publications constitute prior art to the claims appended hereto.

Further Aspects of the Invention

In further aspects of the present invention are provided in the following numbered paragraphs (paras):

1. An engineered Treg comprising a T cell receptor (TCR), wherein the TCR comprises an α chain and a β chain,
   wherein the α chain and the β chain each comprises three complementarity determining regions (CDRs) of a TCR as show in Table 1 or Table 2
   or a variant of those sequences having up to three amino acid changes.
2. An engineered Treg according to para 1, wherein the TCR comprises a combination of an α chain and a β chain of a TCR as show in Table 1 or Table 2 or a variant having at least 80% sequence identity thereto.
3. An engineered Treg according to para 1 or 2, wherein the constant region domains of the α chain and β chain of the TCR each comprise an additional cysteine residue, enabling the formation of an extra disulphide bond between the α chain and the β chain.
4. An engineered Treg according to any preceding claim, wherein the Treg is derived from a T cell isolated from a subject.

5. A pharmaceutical composition comprising an engineered Treg according to any preceding para.
6. An engineered Treg or pharmaceutical composition according to any preceding para for use in treating a disease.
7. The use of an engineered Treg or pharmaceutical composition according to any of paras 1 to 5 in the manufacture of a medicament.
8. A method for treating or preventing a disease in a subject in need of same which comprises the step of administering an engineered Treg or pharmaceutical composition according to any of paras 1 to 5 to the subject.
9. An engineered Treg or pharmaceutical composition for use, a use or a method according to any of para 6 to 8 wherein the disease is multiple sclerosis.
10. An engineered Treg or pharmaceutical composition for use, a use or a method according to any of paras 6 to 9 wherein the subject is an HLADRB1*1501 or HLADRB1*0401 positive subject.
11. A vector which comprises a nucleic acid sequence which encodes a TCR as defined in any one of para 1 to 5 and a nucleic acid sequence which encodes FOXP3.
12. A kit of polynucleotides or vectors which comprises a first polynucleotide or vector which comprises a nucleic acid sequence which encodes a TCR as defined in any one of paras 1 to 5 and a second polynucleotide or vector which comprises a nucleic acid sequence which encodes FOXP3.
13. A method for producing an engineered Treg according to any of paras 1 to 5 which comprises the step of introducing into a cell in vitro or ex vivo a polynucleotide encoding a TCR as defined in any of paras 1 to 5.
14. A method according to para 13 wherein the method further comprises the step of introducing into the cell in vitro or ex vivo a polynucleotide encoding a FOXP3 protein.
15. A method according to para 13 or 14 wherein the cell is a T cell.
16. A method according to para 15 wherein the T cell is a natural Treg which expresses FOXP3.
17. A method according to para 16 wherein the T cell is a conventional T cell.
18. A method according to para 13 to 17 wherein the step of introducing the polynucleotide encoding a TCR and the polynucleotide encoding FOXP3 are performed sequentially, separately or simultaneously.
19. A method according to para 18 wherein the polynucleotide encoding a TCR and the polynucleotide encoding FOXP3 are introduced to the cell using the vector of para 11.

As will be apparent, the further aspects of the invention provided by the numbered paragraphs above are defined by the sequences of the TCRs disclosed in Table 1 and Table 2, in particular the sequences of the CDRs (or variants thereof) and variable regions (or variants thereof). As such, it will be apparent that further embodiments and features described herein in respect of other articles and/or characteristics—for example—general features of the TCR, features of the TCR constant region, the cell or Treg, vector, or medical uses are equally applicable to the aspect of the invention described in the numbered paragraphs above.

TABLE 1

MBP81-99 / DR15 TCRs

| TCR | Aloha chain CDRs | Beta chain CDRs | Aloha Variable | Beta Variable |
|---|---|---|---|---|
| 1. Ob-2F3 | TSINN (SEQ ID NO: 66) IRSNERE (SEQ ID NO: 67) ATDATSGTYKYI (SEQ ID NO: 68) | DFQATT (SEQ ID NO: 69) SNEGSKA (SEQ ID NO: 70) SARDLTSGSLNEQF (SEQ ID NO: 71) | SQQGEEDPQALSIQEGEN ATMNCSYKTSINNLQWYR QNSGRGLVHLILIRSNER EKHSGRLRVTLDTSKKSS SLLITASRAADTASYFCA TDATSGTYKYIFGTGTRL KVLAN (SEQ ID NO: 72) | GAWSQHPSWVICKSGTSV KIECRSLDFQATTMFWYRQ FPKQSLMLMATSNEGSKAT YEQGVEKDKFLINHASLT L STLTVTSAHPEDSSFYICS ARDLTSGSLNEQFFGPGTR LTVL (SEQ ID NO: 73) |
| 2. Ob-3D1 | TSINN (SEQ ID NO: 74) IRSNERE (SEQ ID NO: 75) ATDGNGNQFY (SEQ ID NO: 76) | SGHAT (SEQ ID NO: 77) FQNNGV (SEQ ID NO: 78) ASSIRHRTNTEAF (SEQ ID NO: 79) | SQQGEEDPQALSIQEGEN ATMNCSYKTSINNLQWYR QNSGRGLVHLILIRSNER EKHSGRLRVTLDTSKKSS SLLITASRAADTASYFCA TDGNGNQFYFGTGTSLTV IPN (SEQ ID NO: 80) | EAGVAQSPRYKIIEKRQSV AFWCNPISGHATLYWYQQI LGQGPKLLIQFQNNGWDD SQLPKDRFSAERLKGVDST LKIQPAKLEDSAVYLCASS IRHRTNTEAFFGQGTRLTV V (SEQ ID NO: 81) |
| 3. Hy-1A8 | DSASNY (SEQ ID NO: 82) IRSNVGE (SEQ ID NO: 83) AASSFGNEKLT (SEQ ID NO: 84) | SGHTA (SEQ ID NO: 85) FQGTGA (SEQ ID NO: 86) ATSALGDTQY (SEQ ID NO: 87) | GENVEQHPSTLSVQEGDS AVIKCTYSDSASNYFPWY KQELGKGPQLIIDIRSNV GEKKDQRIAVTLNKTAKH FSLHITETQPEDSAVYFC AASSFGNEKLTFGTGTRL TIIPN (SEQ ID NO: 88) | GAGVSQTPSNKVTEKGKYV ELRCDPISGHTALYWYRQS LGQGPEFLIYFQGTGAADD SGLPNDRFFAVRPEGSVST LKIQRTERGDSAVYLCATS ALGDTQYFGPGTRLTVL (SEQ ID NO: 89) |
| 4. Hy-2E11 | TSINN (SEQ ID NO: 90) IRSNERE (SEQ ID NO: 91) ATDSGGSYIPT (SEQ ID NO: 92) | SQVTM (SEQ ID NO: 93) ANQGSEA (SEQ ID NO: 94) SAWPSGQGTYGYT (SEQ ID NO: 95) | SQQGEEDPQALSIQEGEN ATMNCSYKTSINNLQWYR QNSGRGLVHLILIRSNER EKHSGRLRVTLDTSKKSS SLLITASRAADTASYFCA TDSGGSYIPTFGRGTSLI VHPY (SEQ ID NO: 96) | SAVISQKPSRDICQRGTSL TIQCQVDSQVTMIFWYRQQ PGQSLTLIATANQGSEATY ESGFVIDKFPISRPNLTFS TLTVSNMSPEDSSIYLCSA WPSGQGTYGYTFGSGTRLT VV (SEQ ID NO: 97) |

TABLE 2

MBP111-129/DR4

| TCR | Aloha chain CDRs | Beta chain CDRs | Alpha Variable | Beta Variable |
|---|---|---|---|---|
| 5. HD1-14 | VSGLRG (SEQ ID NO: 26) LYSAGEE (SEQ ID NO: 27) AVQGAGGYQKVT (SEQ ID NO: 28) | MNHNS (SEQ ID NO: 29) SASEGT (SEQ ID NO: 30) ASSEWASGYT (SEQ ID NO: 31) | EDQVTQSPEALRLQEGES SSLNCSYTVSGLRGLFWY RQDPGKGPEFLFTLYSAG EEKEKERLKATLTKKESF LHITAPKPEDSATYLCVT QGAGGYQKVTFGIGTKLQ VIPN (SEQ ID NO: 32) | NAGVTQTPKFQVLKTGQSM TLQCAQDMNHNSMYWYRQD PGMGLRLIYYSASEGTTDK GEVPNGYNVSRLNKREFSL RLESAAPSQTSVYFCASSE WASGYTFGSGTRLTW (SEQ ID NO: 33) |
| 6. MS3-1 | VSGLRG (SEQ ID NO: 34) LYSAGEE (SEQ ID NO: 35) AAYGSSNTGKLI (SEQ ID NO: 36) | GTSNPN (SEQ ID NO: 37) SVGIG (SEQ ID NO: 38) AWSAPGTAYTEAF (SEQ ID NO: 39) | EDQVTQSPEALRLQEGES SSLNCSYTVSGLRGLFWY RQDPGKGPEFLFTLYSAG EEKEKERLKATLTKKESF LHITAPKPEDSATYLCAA YGSSNTGKLIFGQGTTLQ VKPD (SEQ ID NO: 40) | SQTIHQWPATLVQPVGSPL SLECTVEGTSNPNLYWYRQ AAGRGLQLLFYSVGIGQIS SEVPQNLSASRPQDRQFIL SSKKLLLSDSGFYLCAWSA PGTAYTEAFFGQGTRLTW (SEQ ID NO: 41) |
| 7. MS3-11 | SSVPPY (SEQ ID NO: 42) YTSAATLV (SEQ ID NO: 43) AVMHNDMR (SEQ ID NO: 44) | MNHEY (SEQ ID NO: 45) SVGAGI (SEQ ID NO: 46) ASRTGTGRASTEAF (SEQ ID NO: 47) | AQSVTQLGSHVSVSEGAL VLLRCNYSSSVPPYLFWY VQYPNQGLQLLLKYTSAA TLVKGINGFEAEFKKSET SFHLTKPSAHMSDAAEYF CAVMHNDMRFGAGTRLTV KPN (SEQ ID NO: 48) | NAGVTQTPKFQVLKTGQSM TLQCAQDMNHEYMSWYRQD PGMGLRLIHYSVGAGITDQ GEVPNGYNVSRSTTEDFPL RLLSAAPSQTSVYFCASRT GTGRASTEAFFGQGTRLTV V (SEQ ID NO: 49) |

TABLE 2-continued

| | | MBP111-129/DR4 | | |
| --- | --- | --- | --- | --- |
| TCR | Alpha chain CDRs | Beta chain CDRs | Alpha Variable | Beta Variable |
| 8. MS1-4H12 | VSGLRG (SEQ ID NO: 50) LYSAGEE (SEQ ID NO: 51) AVQANNYGQNFV (SEQ ID NO: 52) | LGHNA (SEQ ID NO: 53) YSLEER (SEQ ID NO: 54) ASSQGPSGNTGELF (SEQ ID NO: 55) | EDQVTQSPEALRLQEGES SSLNCSYTVSGLRGLFWY RQDPGKGPEFLFTLYSAG EEKEKERLKATLTKKESF LHITAPKPEDSATYLCAV QANNYGQNFVFGPGTRLS VLPY (SEQ ID NO: 56) | ETGVTQTPRHLVMGMTNKK SLKCEQHLGHNAMYWYKQS AKKPLELMFVYSLEERVEN NSVPSRFSPECPNSSHLFL HLHTLQPEDSALYLCASSQ GPSGNTGELFFGEGSRLTV L (SEQ ID NO: 57) |
| 9. HD-102 | TISGTDY (SEQ ID NO: 58) GLTSN (SEQ ID NO: 59) ILRGRTSYDKVI (SEQ ID NO: 60) | MGHRA (SEQ ID NO: 61) YSYEKL (SEQ ID NO: 62) ASSQGSGGGVTGELF (SEQ ID NO: 63) | DAKTTQPNSMESNEEEPV HLPCNHSTISGTDYIHWY RQLPSQGPEYVIHGLTSN VNNRMASLAIAEDRKSST LILHRATLRDAAVYYCIL RGRTSYDKVIFGPGTSLS VIPN (SEQ ID NO: 64) | DTEVTQTPKHLVMGMTNKK SLKCEQHMGHRAMYWYKQK AKKPPELMFVYSYEKLSIN ESVPSRFSPECPNSSLLNL HLHALQPEDSALYLCASSQ GSGGGVTGELFFGEGSRLT VL (SEQ ID NO: 65) |

The invention will now be further described by way of Examples, which are meant to serve to assist one of ordinary skill in the art in carrying out the invention and are not intended in any way to limit the scope of the invention.

EXAMPLES

Example 1—Expression and Functional Studies

Figure 1:
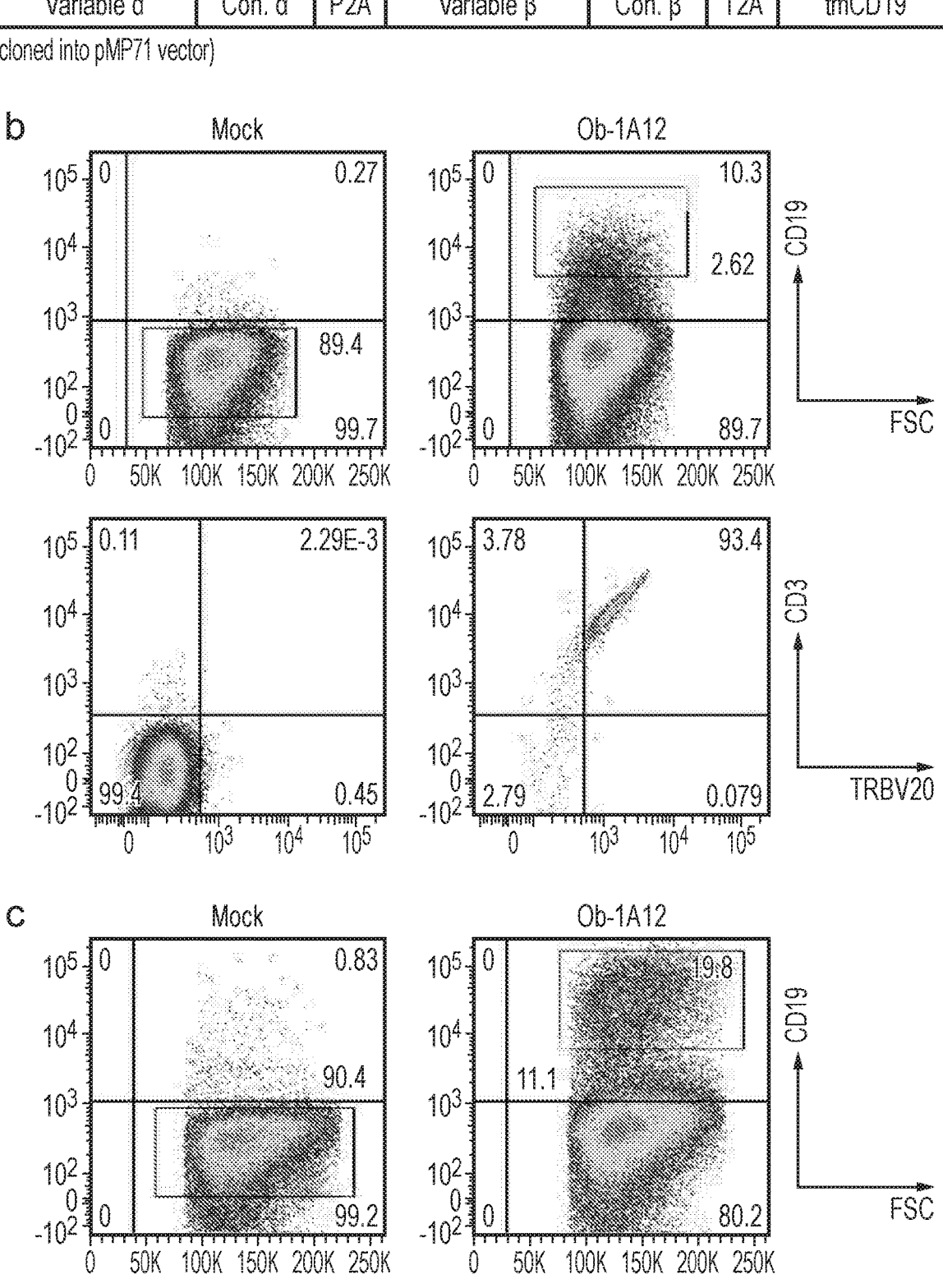
FIG. 1—Schematic representation of the retroviral vector for the Ob-1A12 TCR and Ob-1A12 TCR expression and functional studies. (a) The Ob-1A12 TCR was cloned into the retroviral pMP71 vector using the alpha chain-P2A-beta chain-T2A-truncated murine CD19 (tmCD19) configuration. Truncated murine CD19 was used as a marker of transduction efficiency. The variable and constant domains were codon optimised. (b) Representative example of 3 independent experiments showing Jurkat cells (not expressing an endogenous TCR) transduced with the Ob-1A12 retroviral construct. Top panel: CD19 expression levels. Bottom panel: CD3 expression levels and TRBV20 (IMGT nomenclature) expression levels in gated CD19$^{high}$ cells. CD3 is used as a surrogate marker for TCR cell surface expression. Cells were stained with anti-TRBV20 Abs to determine variable beta chain expression. (c) Representative example of 4 independent experiments showing MACS sorted CD4+ human T cells transduced with the Ob-1A12 TCR retroviral construct. Top panel: CD19 expression levels. Bottom panel: The percentage of CD4+ cells expressing TRBV20 in gated CD19$^{high}$ cells. Cells were stained with anti-TRBV20 Abs to determine variable beta chain expression. (d) Representative example of 4 independent experiments showing human CD4+ T cells transduced with the Ob-1A12 TCR and stimulated with APCs loaded with saturating concentrations of relevant peptide or control peptide. Shown is the frequencies of gated CD19$^{high}$ T cells that produced IL2 and/or IFNg as determined by intracellular cytokine staining 18 h after stimulation in the presence of BFA. APCs were CHO cells expressing CD80 and CD86 and HLA-DRB1*1501. (e) Comparison of antigen-specific cytokine production of CD4+ T cells transduced with Ob-1A12 and Ob-2F3 TCRs across a range of peptide concentration. Shown is the frequency of cytokine-producing cells among transduced cells (CD19high), measured by intracellular cytokine staining as described in figure c.
Figure 1:
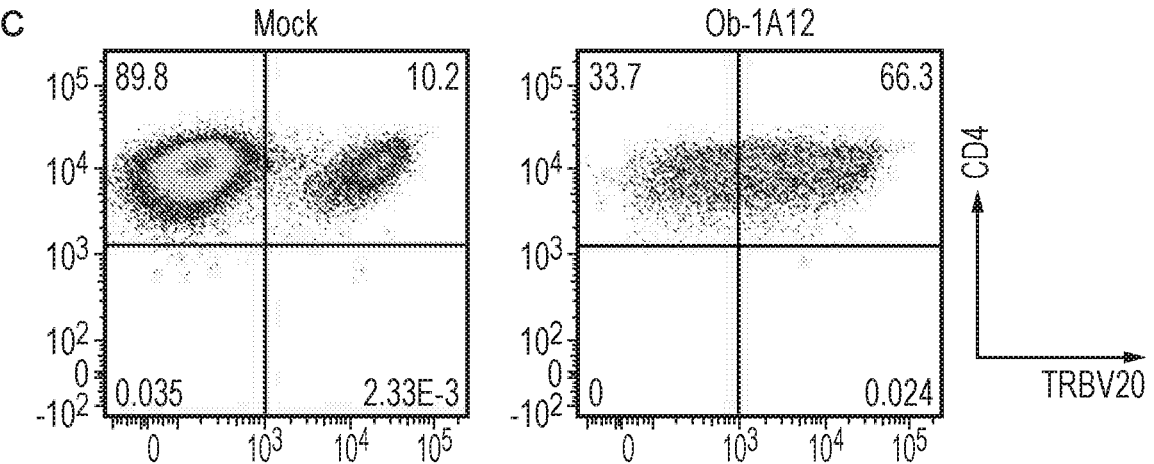
Figure 1:
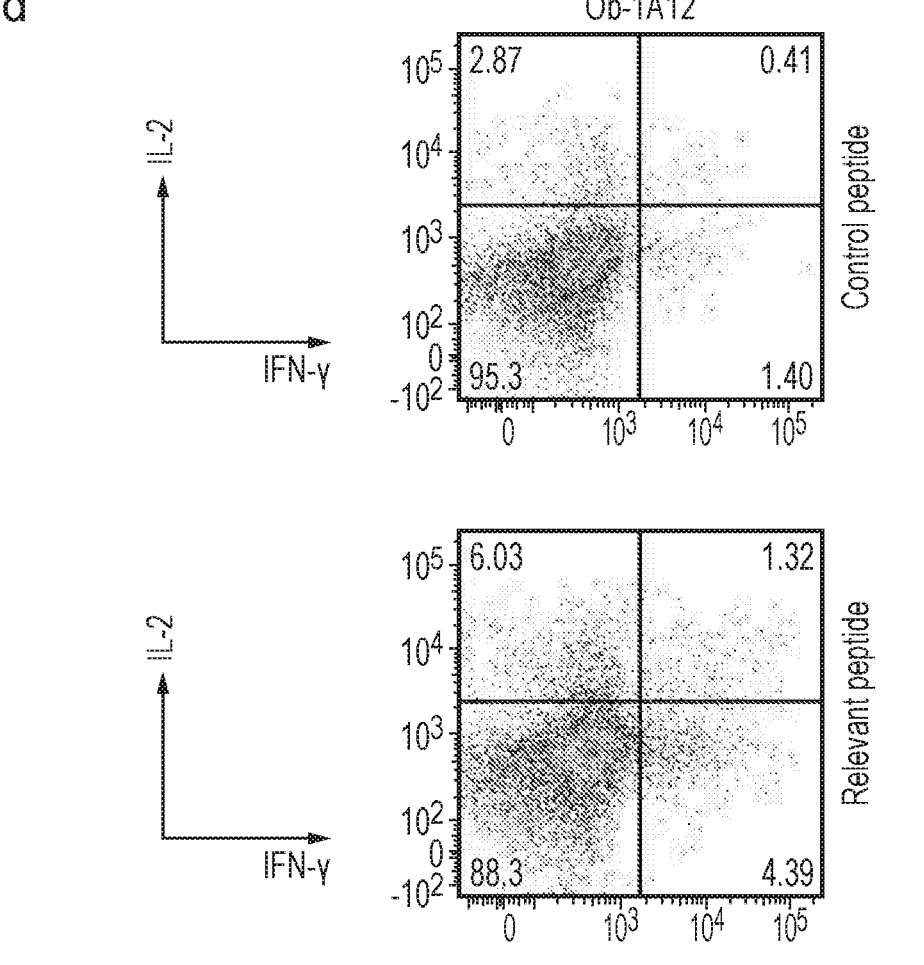
Figure 1:
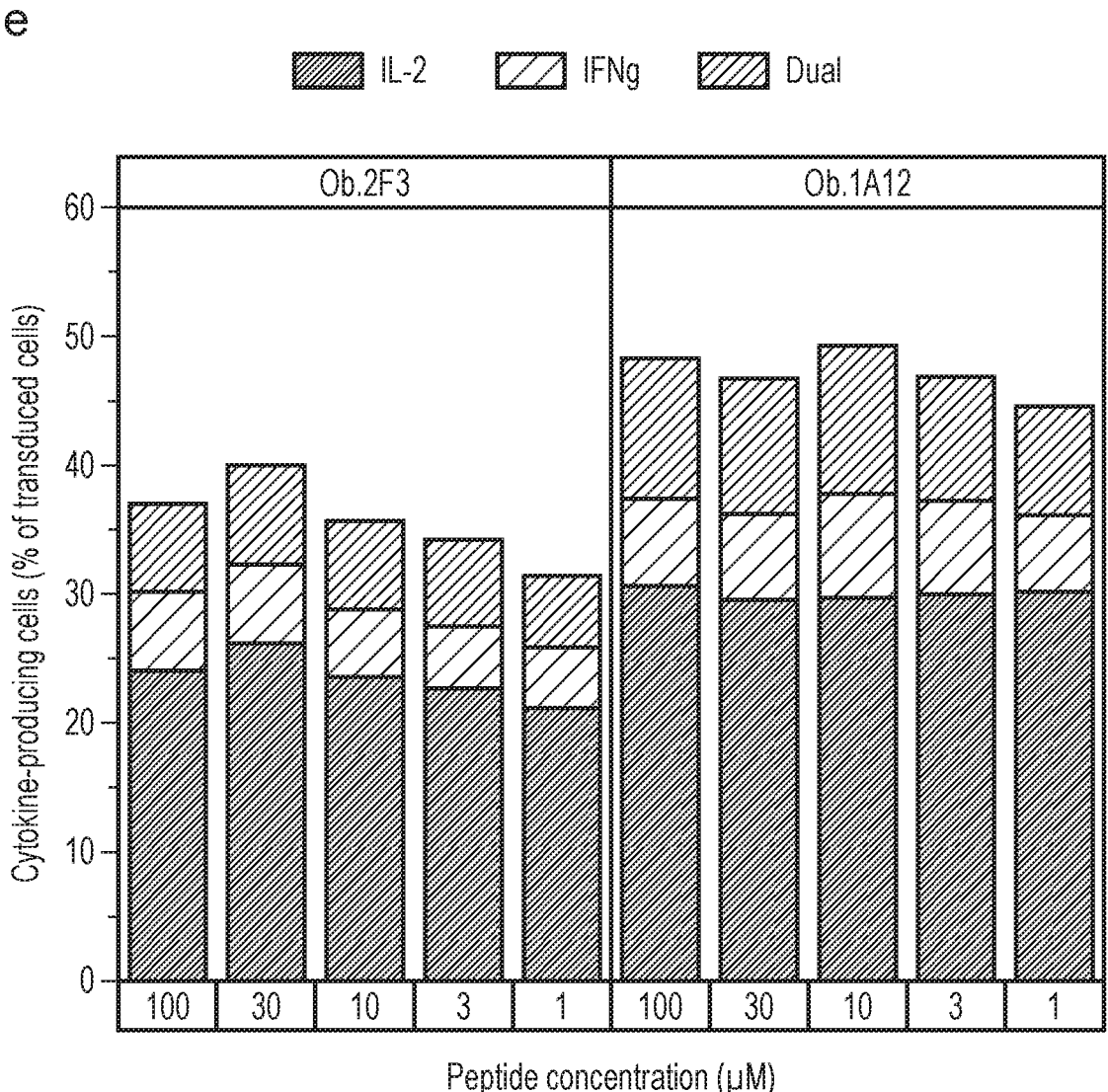

The Ob-1A12 TCR was cloned into the retroviral pMP71 vector using the alpha chain-P2A-beta chain-T2A-truncated murine CD19 (tmCD19) configuration (FIG. 1A).

The Ob-1A12 TCR was productively expressed in Jurkat cells (FIG. 1B) and CD4+ human T cells (FIG. 10).

Human CD4+ T cells transduced with Ob-1A12 and stimulated with APCs loaded with saturating concentrations of relevant peptide were capable of antigen-specific cytokine responses (FIG. 1D).

Ob-1A12 was associated with increased percentages of cytokine-produced CD4+ human T cells, particularly at low antigen concentration (FIG. 1E).

Antigen-Specific Suppression of with a Reference MBP TCR Transduced Treg

CD80+CD86+DR4+ CHO cells were loaded with peptide and irradiated before being resuspended at $0.1 \times 10^6$ cells/ml. Transduced responder T cells were stained with CFSE cell trace dye in warmed PBS at 37 degrees for 3 minutes before addition of equal volumes of warm FBS and a further 3 minute incubation.

Cells were washed in 5× volume of complete media before being counting and resuspended at $1 \times 10^6$ transduced cells/ml. The transduction efficiency of Tconv and Treg were determined by flow cytometry. Regulatory T cells are removed from culture, washed and resuspended at $1 \times 10^6$ transduced cells/ml in complete RPMI. Cells were plated 1 Treg:0.1 CHO cells: and varying ratios of Tconv. Proliferation was determined by analysing dilution of carboxyfluorescein succinimidyl ester (CFSE)-stained T cony.

Figure 4:
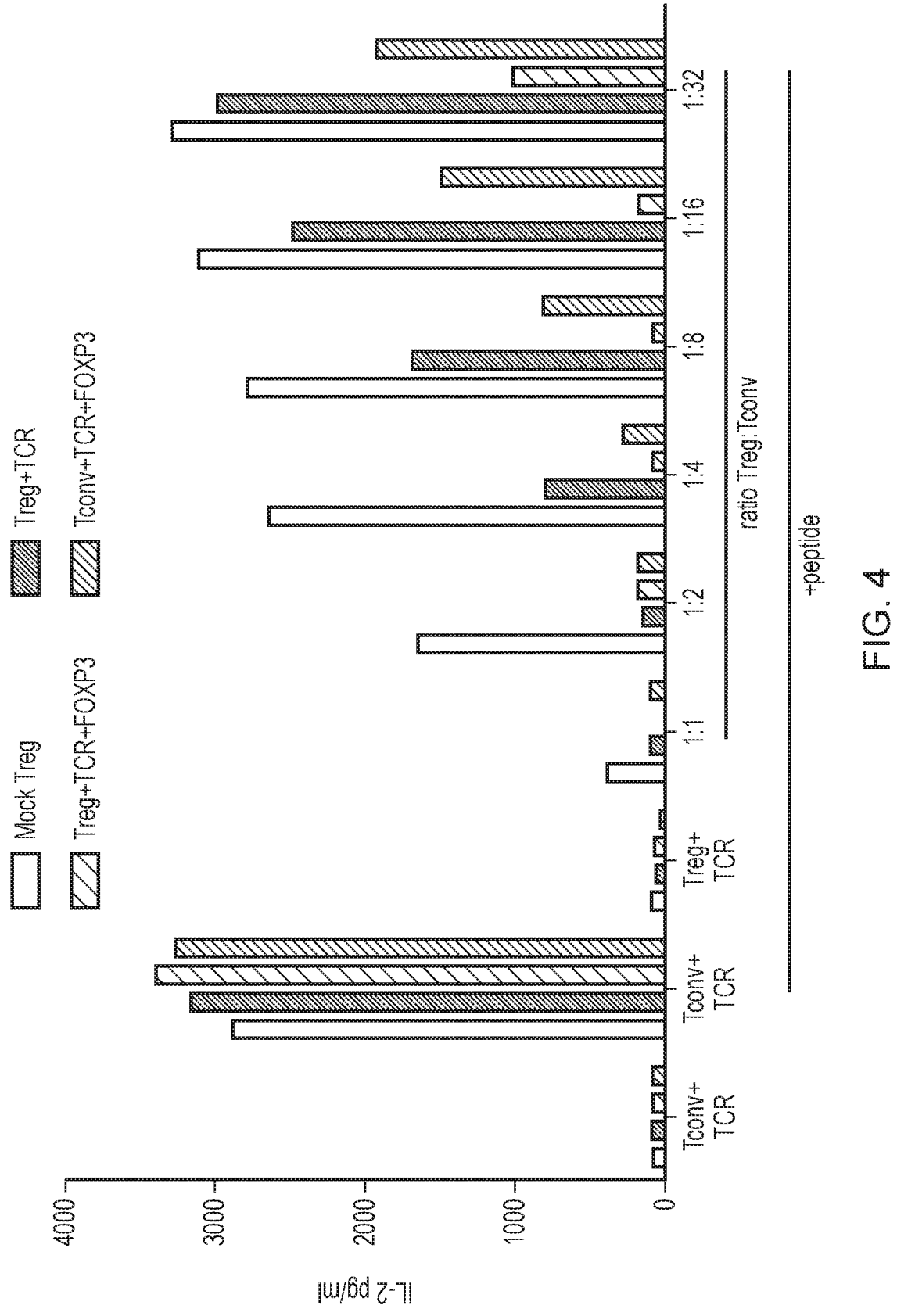
FIG. 4—TCR transduced T conv were stained with CFSE and cultured with or without peptide-pulsed irradiated APC at a ratio of 1 Tconv:0.1 APC for 4 days. Mock Treg (bar on the furthest left), reference MBP TCR-transduced Treg (second bar from the left), reference MBP TCR-FOXP3-transduced Treg (third bar from the left) and reference MBP TCR-FOXP3-transduced Tconv (fourth bar from the left in each group) were added in the indicated ratios. Supernatants were collected and assayed for IL-2 by ELISA. These data show that TCR-transduced Treg suppress T cell responses in an antigen-specific manner.
Figure 5:
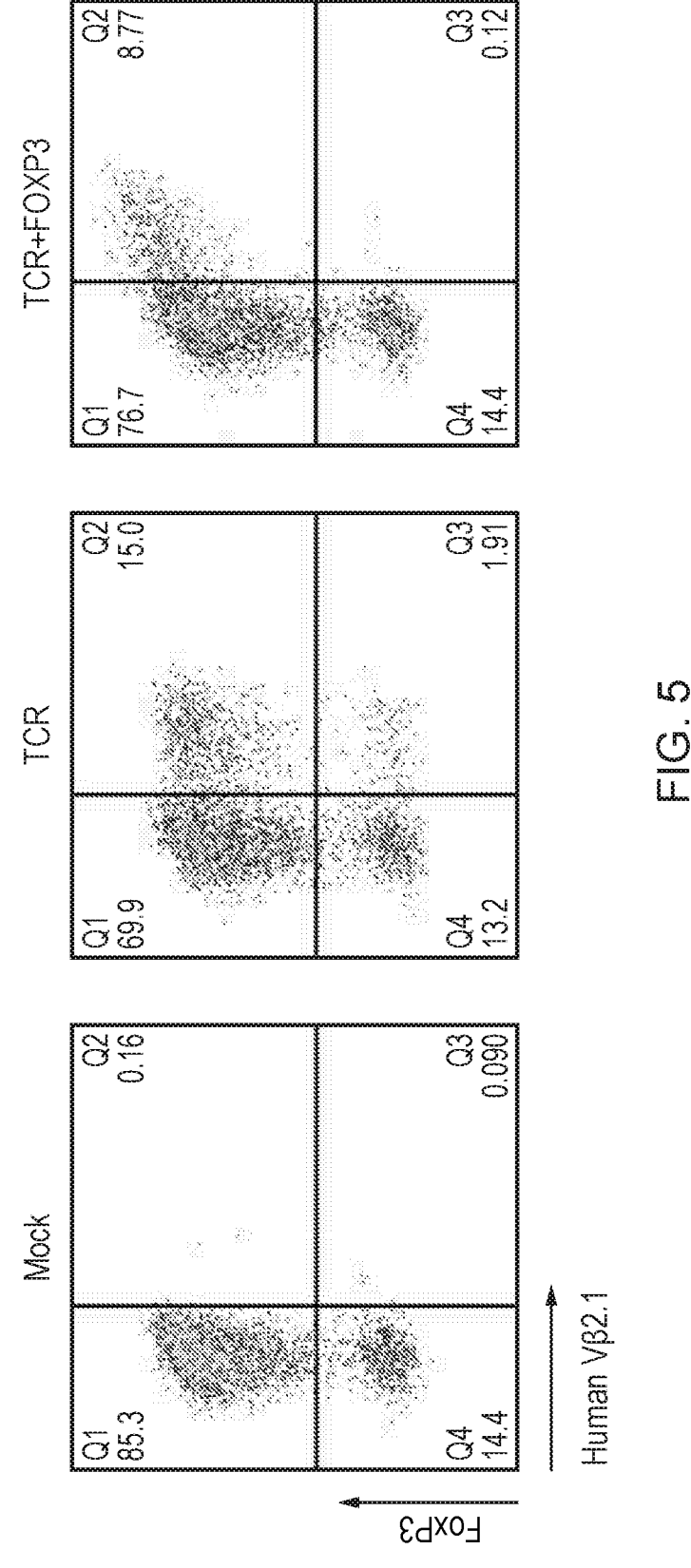
FIG. 5—TCR transduced regulatory T cells can engraft into irradiated hosts but require exogenous FOXP3 expression to prevent accumulation of TCR+FOXP3− cells.
Figure 5:
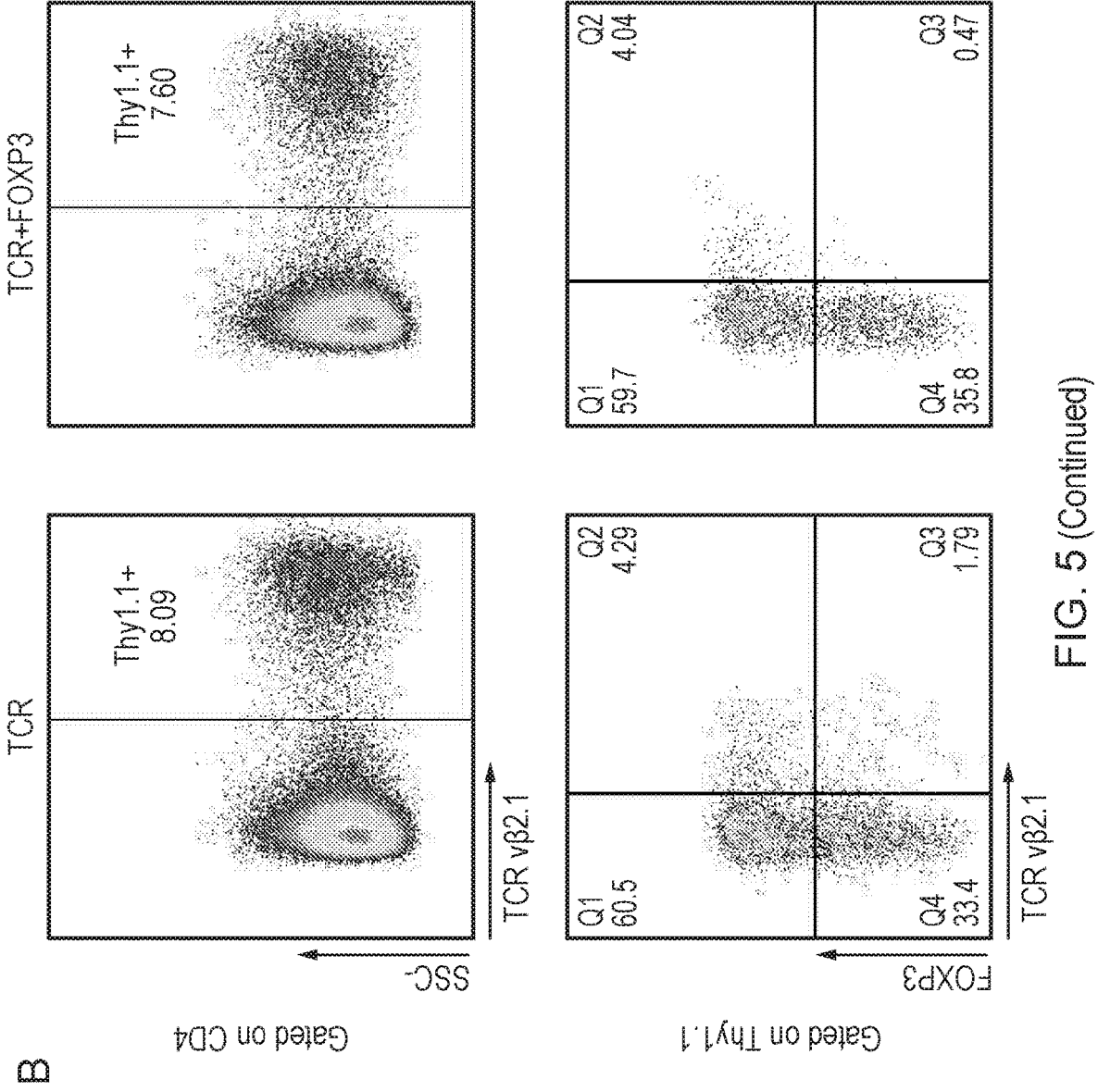

The data in FIG. 4 show that TCR-transduced Tregs suppress proliferation in an antigen-specific manner. Supernatants were collected from the culture media and were assayed for IL-2 by ELISA. The data presented in FIG. 5 show that TCR-transduced Treg suppress IL-2 production in an antigen-specific manner.

The expression cassette used in this reference experiment encoded FOXP3 and the reference MBP TCR in a 5'-3' orientation.

Example 2A—Treg Expressing Exogenous FOXP3 Engraft, Persist and Retain FoxP3, CD25 and TCR Expression Thy1.1+CD4+CD25+ or CD45.1+CD4+CD25+ Treg were isolated from lymph nodes and splenocytes of HLA-DRB*0401 transgenic mice by bead sort. CD45.1+ Treg were transduced with TCR and Thy1.1+ Treg were transduced with TCR+ murine FOXP3. 1 day after transduction TCR or TCR+FOXP3 transduced cells were injected in a 1:1 ratio into HLA-DRB*0401 transgenic hosts conditioned with 4 Gy irradiation. FACS plots show the ratio of CD45.1: Thy1.1 of injected cells and their respective FOXP3 expression.

After 7 weeks flow cytometry was used to identify engrafted cells by staining for TCR. The ratio of CD45.1: Thy1.1 within the TCR+ population was determined and the phenotype of engrafted CD45.1 (Treg transduced with TCR) or Thy1.1 (Treg transduced with TCR+FOXP3) cells was examined by staining for FOXP3 and CD25.

Thy1.1+CD4+CD25+ Treg were isolated from lymph nodes and splenocytes of HLA-DRB*0401 transgenic mice by bead sort. Treg were transduced TCR, TCR+murine FOXP3 or cultured with virus-free supernatant (mock). 1 day after transduction TCR or TCR+FOXP3 transduced cells were injected into HLA-DRB*0401 transgenic hosts conditioned with 4 Gy irradiation. 7 weeks later flow cytometry was used to determine the engraftment of transduced Treg FIG. 5, A shows the transduction efficiency determined through expression of human variable 2.1 and murine Foxp3 on dl post-transduction. FIG. 5, B shows splenocytes from mice that received Treg transduced with TCR or TCR+FOXP3 stained with Thy1.1 to identify transferred cells (top panel) and FOXP3 and TCR (bottom panel). FIG. 5, C shows cumulative data showing fold change in transduction efficiency (left panel) and fold change in absolute number of transduced cells (right panel) relative to day of injection for Treg transduced with TCR or TCR+FOXP3. FIG. 5, D shows a representative expression of FOXP3 within transduced cells 7 weeks after transfer. Graphs show cumulative of percentage FOXP3+ cells within the transduced population at week 7 (left) and the fold change in FOXP3+ cells relative to the day of injection.

Example 2B—Treg Expressing Exogenous FOXP3 Retain Treg Functionality after 7 Weeks In Vivo Whilst Tregs not Expressing Exogenous FOXP3 Acquire the Ability to Produce Effector Cytokines Splenocytes were cultured for 4 hours with CD86+HLA-DR4+CHO cells pulsed with irrelevant peptide or 10 uM MBP. Treg expressing exogenous FOXP3 retain Treg functionality after 7 weeks in vivo as demonstrated by lack of effector cytokine production, whilst Tregs not expressing exogenous FOXP3 acquire the ability to produce effector cytokines (FIG. 6).

Example 3—Expression and Functional Studies for Further TCR

Expression and functional studies were performed for the following TCRs using the methods as described for Example 1: Ob-2F3 (FIG. 7), Ob-3D1 (FIG. 8), Hy-1A8 (FIG. 9), Hy-2E11 (FIG. 10), HD1-14 (FIG. 11), MS3-1 (FIG. 12), MS3-11 (FIG. 13), MS1-4H12 (FIG. 14) and HD4-1C2 (FIG. 15).

Methods

Retroviral Transduction

Figure 2:
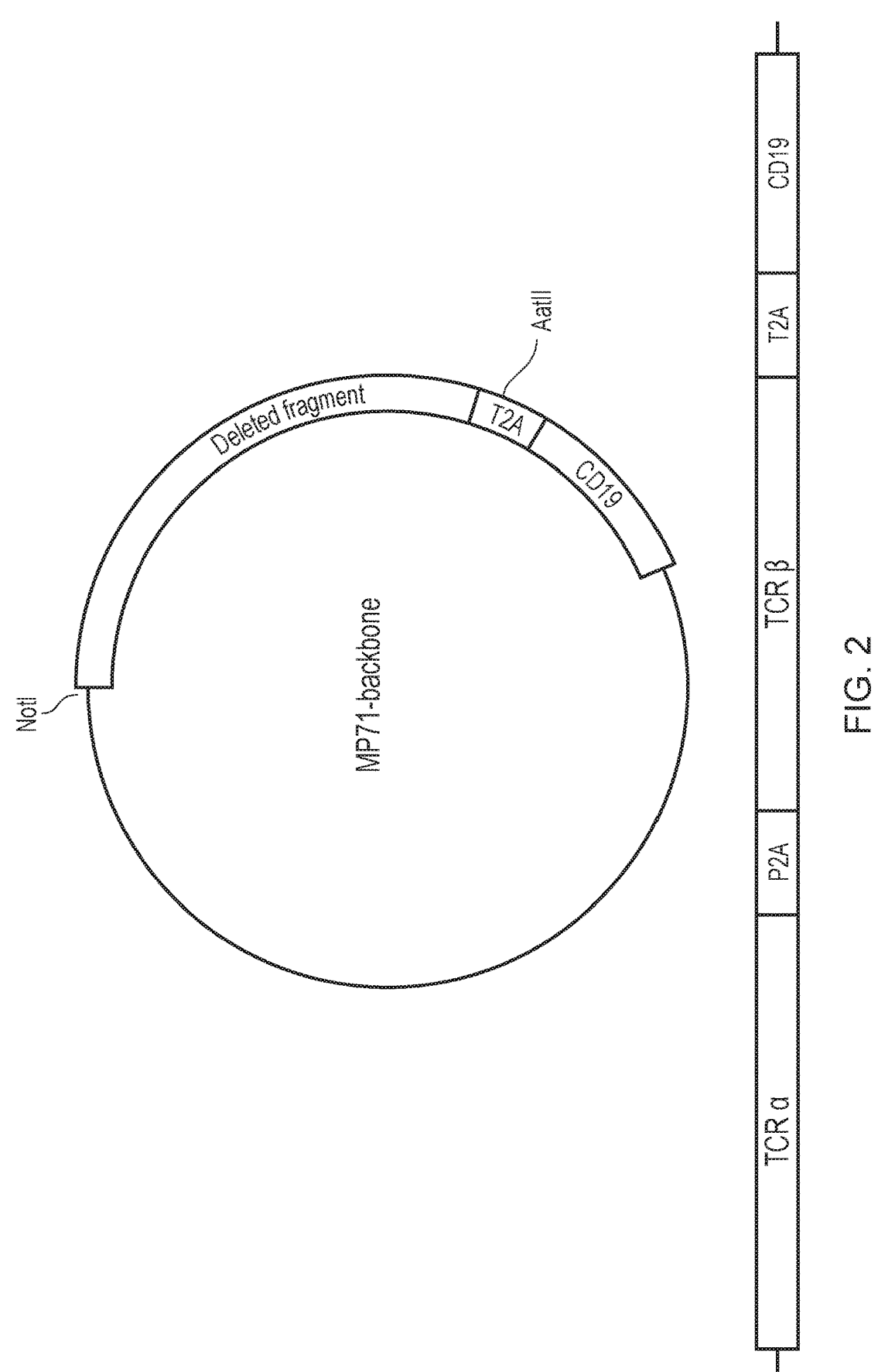
FIG. 2—Diagram showing retroviral vector and open reading frame used in Example 1
Figure 3:
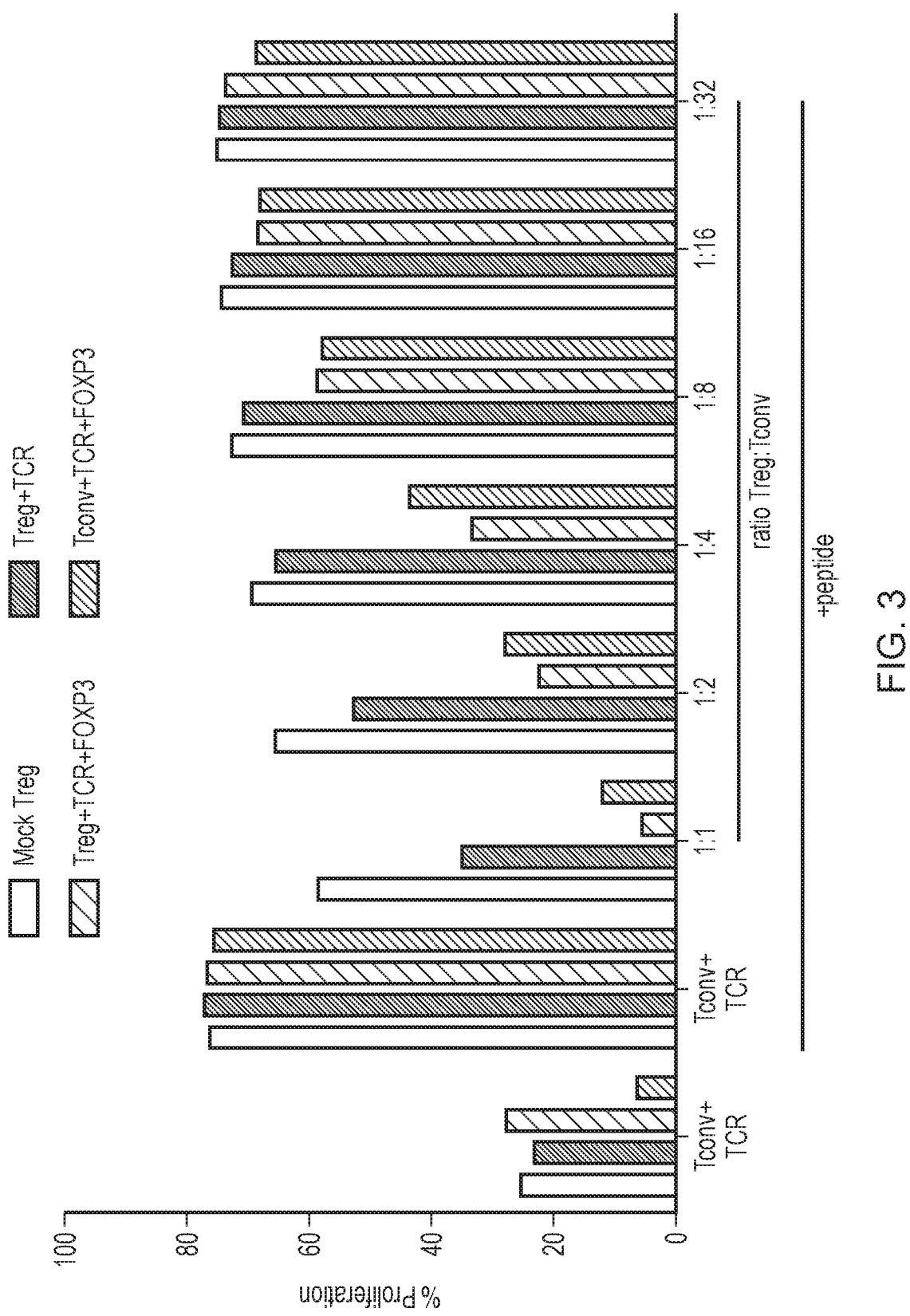
FIG. 3—TCR transduced T conv were stained with CFSE and cultured with or without peptide-pulsed irradiated APC at a ratio of 1 Tconv:0.1 APC for 4 days. Mock Treg (bar on the furthest left), reference MBP TCR-transduced Treg (second bar from the left), reference MBP TCR-FOXP3-transduced Treg (third bar from the left) and reference MBP TCR-FOXP3-transduced Tconv (fourth bar from the left in each group) were added in the indicated ratios. Proliferation was determined by analysing dilution of CFSE-stained Tconv (B). These data show that TCR-transduced Treg suppress T cell responses in an antigen-specific manner.

Phoenix Ampho cells (were transfected with the retroviral vector (as illustrated in FIG. 2) using FuGene HD reagent (Promega). Retrovirus-containing supernatant from transfected Phoenix Ampho cells was collected and used to transduce Jurkat cells or primary CD4 cells. Briefly, cells were mixed with the retroviral supernatant and transferred into a tissue-culture plate coated with Retronectin (Takara Bioscence). Transduction was done by spinfection (90 min centrifugation at 2000 rpm) after which the retroviral supernatant was replaced by fresh culture medium with cytokines when required.

TCR Expression Validation

Expression of the TCR was measured 3 days post-transduction by flow cytometry. Transduced cells were identified by the expression of the truncated murine CD19 molecule. For Jurkat cells, CD3 expression was used as a proxy for the expression of the TCR as the cells do not produce a functional TCR and therefore have no CD3 expression in their native state. CD4 T cells were isolated from frozen leukocytes from healthy donors using anti-CD4 magnetic beads (Miltenyi Biotech) and activated for 48 h with CD3/CD28 Dynabeads (Life Technologies) and IL-2 (Roche) before transduction. When applicable, TCR expression was measured in CD4 T cells using an anti-V1320 antibody.

Cytokine-Production Assay

For antigen-specific cytokine production assay, Chinese Hamster Ovary (CHO) cells expressing the relevant HLA-DR molecules together with co-stimulatory molecules CD80 or CD86 were used as antigen-presenting cells (APCs). Peptides were added to 1:1 mix of CHO-CD80:CHO-CD86 and incubated for 2 h to allow for presentation of the antigen on MHC molecules. Transduced CD4 cells and antigen-loaded APCs were combined and incubated for 18 h with Brefeldin A (BFA) before proceeding to intracellular cytokine staining. Antigen-specific response was detected by an increase in cells producing interleukin-2 and interferon-gamma above the control (cells stimulated by an irrelevant peptide).

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cellular immunology or related fields are intended to be within the scope of the following claims.

---

The invention claimed is:

1. An isolated engineered human regulatory T cell (Treg) comprising a T cell receptor (TCR) that is capable of specifically binding to a peptide comprising myelin basic protein (MBP) 82-102 (SEQ ID NO: 12) when the peptide is presented by a human leukocyte antigen D related (HLADR) B1*1501 molecule, wherein the TCR comprises an α chain and a β chain, wherein the α chain of the TCR comprises three complementarity determining regions (CDRs) having the following amino acid sequences:

```
CDR1α
                          (SEQ ID NO: 3)
TSINN

CDR2α
                          (SEQ ID NO: 4)
IRSNERE

CDR3α
                          (SEQ ID NO: 1)
ATDTTSGTYKYI;
``` and wherein the β chain of the TCR comprises three CDRs having the following amino acid sequences:

```
CDR1β
                          (SEQ ID NO: 5)
DFQATT

CDR2β
                          (SEQ ID NO: 6)
SNEGSKA

CDR3β
                          (SEQ ID NO: 2)
SARDLTSGANNEQF.
```

2. The isolated engineered human Treg according to claim 1, wherein:

(a) the variable region of the α chain of the TCR comprises an amino acid sequence having at least 80% sequence identity to SEQ ID NO:7; and (b) the variable region of the β chain of the TCR comprises an amino acid sequence having at least 80% sequence identity to SEQ ID NO: 8.

3. The isolated engineered human Treg according to claim 1, wherein the constant region domains of the α chain and β chain of the TCR each comprise an additional cysteine residue that enables the formation of an extra disulphide bond between the α chain and the β chain.

4. The isolated engineered human Treg according to claim 1, wherein:

(a) the α chain of the TCR comprises an amino acid sequence having at least 80% sequence identity to SEQ ID NO: 9; and (b) the β chain of the TCR comprises an amino acid sequence having at least 80% sequence identity to SEQ ID NO: 10.

5. The isolated engineered human Treg according to claim 1, wherein the Treg is isolated from a human subject.

6. A pharmaceutical composition comprising the engineered Treg according to claim 1.

7. An isolated vector comprising a nucleic acid sequence which encodes a TCR as defined in claim 1, and a nucleic acid sequence which encodes Forkhead box protein P3 (FOXP3).

8. A kit of polynucleotides or vectors, comprising a first polynucleotide or vector which comprises a nucleic acid sequence which encodes a TCR as defined in claim 1, and a second polynucleotide or vector which comprises a nucleic acid sequence which encodes FOXP3.

9. A method for producing an isolated engineered human Treg, comprising introducing into a CD4+CD25+ or CD4+CD25− T cell in vitro or ex vivo the vector according to claim 7.

\* \* \* \* \*